(12) United States Patent
Vera et al.

(10) Patent No.: US 10,533,156 B2
(45) Date of Patent: Jan. 14, 2020

(54) METHODS OF CELL CULTURE FOR ADOPTIVE CELL THERAPY

(71) Applicants: Wilson Wolf Manufacturing, New Brighton, MN (US); Baylor College of Medicine, Houston, TX (US)

(72) Inventors: Juan F. Vera, Bellaire, TX (US); Cliona M. Rooney, Bellaire, TX (US); Ann M. Leen, Bellaire, TX (US); John R. Wilson, New Brighton, MN (US)

(73) Assignees: Baylor College of Medicine, Houston, TX (US); Wilson Wolf Manufacturing, New Brighton, MN (US)

( * ) Notice: Subject to any disclaimer, the term of this patent is extended or adjusted under 35 U.S.C. 154(b) by 0 days.

(21) Appl. No.: 15/395,662

(22) Filed: Dec. 30, 2016

(65) Prior Publication Data
US 2017/0267973 A1  Sep. 21, 2017

Related U.S. Application Data

(60) Continuation of application No. 14/579,373, filed on Dec. 22, 2014, now Pat. No. 9,567,565, which is a division of application No. 13/475,700, filed on May 18, 2012, now Pat. No. 8,956,860, which is a contin-
(Continued)

(51) Int. Cl.
*C12N 5/0783* (2010.01)
*C12M 1/04* (2006.01)

(52) U.S. Cl.
CPC .......... *C12N 5/0638* (2013.01); *C12M 23/24* (2013.01); *C12N 2501/2302* (2013.01); *C12N 2502/11* (2013.01)

(58) Field of Classification Search
CPC ...... C12M 27/02; C12M 35/04; C12M 21/04; C12M 23/14; C12M 29/10; C12M 28/04;
(Continued)

(56) References Cited

U.S. PATENT DOCUMENTS

| 4,201,845 A | 5/1980 | Feder et al. |
| 4,649,118 A | 3/1987 | Anderson |

(Continued)

FOREIGN PATENT DOCUMENTS

| EP | 0307048 | 3/1989 |
| EP | 1978089 | 10/2008 |

(Continued)

OTHER PUBLICATIONS

Kevin J Curran et al: "Validation of Donor Derived Virus Specifi c T-Lymphocytes Genetically Modifi ed to Target the CD19 Antigen for the Treatment of Relapsed Leukemia", Molecular Therapy, vol. 19, No. Supplement 1, May 1, 2011 (May 1, 2011), pp. s90-s90, XP055451639, England.
(Continued)

*Primary Examiner* — Michael L Hobbs
(74) *Attorney, Agent, or Firm* — Patterson Thuente Pedersen, P.A.

(57) ABSTRACT

An improved method of culturing cells for cell therapy applications that includes growing desired cells in the presence of antigen-presenting cells and/or feeder cells and with medium volume to surface area ratio of up to 1 ml/cm² if the growth surface is not comprised of gas permeable material and up to 2 ml/cm² if the growth surface is comprised of gas permeable material. The desired cells are at a surface density of less than $0.5 \times 10^6$ cells/cm² at the onset of a production cycle, and the surface density of the desired cells plus the surface density of the antigen presenting cells and/or feeder cells are at least about $1.25 \times 10^5$ cells/cm².

20 Claims, 40 Drawing Sheets

Related U.S. Application Data uation-in-part of application No. 12/963,597, filed on Dec. 8, 2010, now Pat. No. 8,809,050.

(60) Provisional application No. 61/267,761, filed on Dec. 8, 2009.

(58) Field of Classification Search
CPC ...... C12M 23/34; C12M 25/02; C12M 23/08; C12N 2501/23; C12N 2501/39; C12N 2502/16; A61K 35/12; A61K 2035/124
USPC .............................................. 435/373, 297.1
See application file for complete search history.

(56) References Cited

U.S. PATENT DOCUMENTS

| | | | |
|---|---|---|---|
| 4,839,292 | A | 6/1989 | Cremonese |
| 5,248,769 | A | 9/1993 | Dorin |
| 5,585,266 | A | 12/1996 | Plitt et al. |
| 5,707,869 | A | 1/1998 | Wolf et al. |
| 5,728,581 | A | 3/1998 | Schwartz et al. |
| 5,731,160 | A | 3/1998 | Melief et al. |
| 5,962,318 | A | 10/1999 | Rooney et al. |
| 6,228,635 | B1 | 5/2001 | Armstrong et al. |
| 8,158,426 | B2 | 4/2012 | Wilson et al. |
| 8,158,427 | B2 | 4/2012 | Wilson et al. |
| 8,168,432 | B2 | 5/2012 | Wilson et al. |
| 8,809,050 | B2 | 8/2014 | Vera et al. |
| 8,956,860 | B2 | 2/2015 | Vera et al. |
| 9,255,243 | B2 | 2/2016 | Wilson et al. |
| 9,567,565 | B2 | 2/2017 | Vera et al. |
| 2003/0235908 | A1 | 12/2003 | Berenson et al. |
| 2005/0106717 | A1 | 5/2005 | Wilson et al. |
| 2005/0109717 | A1* | 5/2005 | Armstrong ............... B41K 1/58 211/39 |
| 2005/0129671 | A1 | 6/2005 | Cooper |
| 2005/0227354 | A1 | 10/2005 | Sagawa et al. |
| 2009/0042293 | A1 | 2/2009 | Hata et al. |
| 2009/0111180 | A1 | 4/2009 | Vilendrer et al. |
| 2010/0261269 | A1 | 10/2010 | June et al. |
| 2011/0129923 | A1 | 6/2011 | Wilson et al. |
| 2011/0136228 | A1 | 6/2011 | Vera et al. |
| 2011/0287542 | A1 | 11/2011 | Wilson et al. |
| 2011/0287543 | A1 | 11/2011 | Wilson et al. |
| 2016/0208216 | A1 | 7/2016 | Vera et al. |

FOREIGN PATENT DOCUMENTS

| | | |
|---|---|---|
| EP | 2119778 | 11/2009 |
| JP | 10-290689 | 4/1998 |
| JP | 10-174581 | 6/1998 |
| JP | 2007061020 | 3/2007 |
| JP | 2011187868 | 9/2011 |
| JP | 2013 512694 A | 4/2013 |
| WO | WO 03/057171 | 7/2003 |
| WO | WO 2004/106484 | 12/2004 |
| WO | WO 2005/035728 | 4/2005 |
| WO | WO 2005/047466 | 5/2005 |
| WO | WO 2005/051927 | 6/2005 |
| WO | WO 2006/026746 | 3/2006 |
| WO | WO 2006/130670 | 12/2006 |
| WO | WO 2008/023786 A1 | 2/2008 |
| WO | WO 2008/023789 | 2/2008 |
| WO | WO 2011/072088 | 6/2011 |
| WO | WO 2012/138858 | 10/2012 |
| WO | WO 2013/188427 | 12/2013 |
| WO | WO 2014/188427 A1 | 11/2014 |

OTHER PUBLICATIONS

S. Terakura et al: "Generation of CD19-chimeric antigen receptor modified CD8+ T cells derived from virus-specific central memory T cells", Blood, vol. 119, No. 1, Jan. 5, 2012 (Jan. 5, 2012), pp. 72-82, XP055247932, US ISSN: 0006-4971, DOI: 10.1182/blood-2011-07-366419.

Application and File History of U.S. Appl. No. 12/963,597, Inventors Vera et al., filed Dec. 8, 2010, issued as U.S. Pat. No. 8,809,050 on Aug. 19, 2014.

Application and File History of U.S. Appl. No. 13/475,700, Inventors Vera et al, filed May 18, 2012, issued as U.S. Pat. No. 8,956,860 on Feb. 17, 2015.

Application and File History of U.S. Appl. No. 13/493,768, inventors Wilson et al., filed Jun. 11, 2012.

International Search Report and Written Opinion for PCT/US2010/059591, Applicant Wilson Wolf Manufacturing Corporation et al., dated Aug. 22, 2011 (6 pgs).

Nakazawa et al., "Optimization of the PiggyBac Transposon System for the Sustained Genetic Modification of Human T Lymphocytes," J. Immunother., 2009, vol. 32, No. 8, pp. 826-836.

Vera et al., "Accelerated Production of Antigen-specific T Cells for Preclinical and Clinical Applications Using Gas-permeable Rapid Expansion Cultureware (G-Rex)," J. Immunother. 2009, vol. 00, No. 00, pp. 1-11.

Vera et al., "Immunotherapy of Human Cancers Using Gene Modified T Lymphocytes," Curr. Gene Ther., Oct. 2009, vol. 9, No. 5, pp. 396-408.

International Search Report for PCT Application PCT/US2013/041861, dated Aug. 23, 2013, 5 pgs.

International Search Report and Written Opinon for PCT Application PCT/US2013/045209, dated Sep. 25, 2013, 5 pgs.

Gerdemann, Ulrike, et al. "Generation of Multivirus-specific T Cells to Prevent/treat Viral Infections after Allogeneic Hematopoietic Stem Cell Transplant". Journal of Visualized Experiments, May 27, 2011, vol. 51, e. 2736 (pp. 1-6).

Office Action dated Dec. 18, 2013 from related U.S. Appl. No. 13/493,768, 10 pgs.

Extended European Search Report from related European Application No. 13192463.1-1403/2698430, dated Feb. 4, 2014, 8 pgs.

Extended European Search Report from related European Application No. 10836660.0-2510086, dated Apr. 24, 2013, 7 pgs.

Brenner, L., et al. "Rapid Generation of Antigen-Specific T Cells for Pre-Clinical and Clinical Applications Using a novel Mini Cell Bioreactor", Biology of Blood and Marrow Transplantation, vol. 15, No. 2, Feb. 1, 2009, p. 137.

Hoffmann, Petra, et al. "Large-scale in vitro expansion of polyclonal human CD4+CD5 high regulatory T cells", Blood, vol. 104, No. 3, Aug. 1, 2004, pp. 895-903.

Papanicolaou, G.A., et al. "Rapid expansion of cytomegalovirus-specific cytotoxic T lymphocytes by artificial antigen-presenting cells expressing a single HLA allele", Blood, vol. 102, No. 7, Oct. 1, 2003, pp. 2498-2505.

International Preliminary Report on Patentability from PCT Application PCT/US2013/045209, dated Dec. 24, 2014, 7 pgs.

International Preliminary Report on Patentability from PCT Application PCT/US2013/041861, dated Jan. 13, 2015, 4 pgs.

Extended European Search Report from EP Application EP 13791247.3, dated Nov. 16, 2015, 4 pgs.

Feuchtinger, Tobias et al., "Adoptive transfer of pp65-specific T cells for the treatment of chemorefractory cytomegalovirus disease or reactivation after haploidentical and matched unrelated stem cell transplantation," *Blood Journal*, vol. 116, No. 20, Nov. 18, 2010, pp. 4360-4367.

Mielke, Stephan et al., "A clinical-scale selective allodepletion approach for the treatment of HLA-mismatched and matched donor-recipient pairs using expanded T lymphocytes as antigen-presenting cells and a TH9402-based photodepletion technique," *Blood Journal*, vol. 111, No. 8, Apr. 15, 2008, pp. 4392-4402.

Vera, Juan F. et al., "Immunotherapy of Human Cancers Using Gene Modified T Lymphocytes," *Current Gene Therapy*, vol. 9, pp. 396-408.

English translation of Office Action from Chinese Application CN 201380025756.5, dated Aug. 16, 2016, 9 pgs.

Nakazawa, Yozo, et al. "PiggyBac-Mediated Cancer Immunotherapy Using EBV-specific Cytotoxic T-cells Expressing HER2-specific Chimeric Antigen Receptor", Mol. Ther. Dec. 2011; 19(12) 2133-2143. 13 pages.

(56) References Cited

OTHER PUBLICATIONS

Vera, Juan F., et al. Abstract of "Safely Improving the in Vivo Survival of Tumor Specific Cytotoxic T Lymphocytes by Co-Transfer of IL7 Receptor Alpha Chain and icaspase9", Blood 2008 112:3534, 5 pages.

Application and file history for U.S. Appl. No. 14/579,373, filed Dec. 22, 2014, inventors Vera et al., issued as U.S. Pat. No. 9,567,565 on Feb. 14, 2017.

Application and file history for U.S. Appl. No. 14/996,447, filed Jan. 15, 2016, inventors Vera et al.

Bondanza et al., "Suicide gene therapy of graft-versus-host disease induced by central memory human T lymphocytes," Blood, 2006; 107:1828-1836.

Gottleib et al., "T time for transplants," Blood, Nov. 25, 2010; 116(22): 4391-3.

Melenhorst et al., "Allogeneic virus-specific T cells with HLA alloreactivity do not produce GVHD in human subjects," Blood, Nov. 25, 2010; 116(22):4700-2.

NCT00840853, "Multi-virus CTLs Expressing CD19 Chimeric Receptors, CD19 Positive Malignancies Post SCT, Multiprat," Apr. 13, 2012, pp. 1-12.

Woolridge et al., "A Single Autoimmune T Cell Receptor Recognizes More Than a Million Different Peptides," J. Biol. Chem., 2012, 287:1168-1177.

Perucci, Katia, et al., "Transferring functional immune responses to pathogens after haploidentical hematopoietic transplantation". Blood, 2005, 106, pp. 4397-4406.

Khanna, Nina, et al., "Generation of a multipathogen-specific T-cell product for adoptive immunotherapy based on activation-dependent expression of CD154". Blood, 2011, 118(4), pp. 1121-1131.

Ramadan, G., et al, "Generation of Th1 T cell responses directed to a HLA Class II restricted epitope from the Aspergillus f16 allergen". Clinical and Experimental Immunology, 2005, 139, pp. 257-567.

Di Stasio, A., Dr., et al., "Phase I clinical trial of allodepleted T cells transduced with inducible capsase 9 suicide gene". Human Gene Therapy, 2010, vol. 21, No., 10, pp. 1363-4.

A. M. Leen et al: "Cytotoxic T lymphocyte therapy with donor T cells prevents and treats adenovirus and Epstein-Barr virus infections alter haploldentical and matched unrelated stem cell transplantation", Blood, vol. 114, No. 19, Aug. 21, 2009 (Aug. 21, 2009), pp. 4283-4292, XP-55200665, ISSN: 0006-4971, DOI: 10.1182/blood-2009-07-232454.

Vallera, Daniel A., et al., "Retroviral Immunotoxin Gene Therapy of Acute Myelogenous Leukemia in Mice Using Cytotoxic T Cells Transduced with an Inteleukin 4/Diptheria Toxin Gene". Cancer Res., 60(2000), p. 976-984.

Zohren, Fabian, et al., "Genetic Modification of Multi Leukemia Antigen-Specific Cytotoxic T Lymphocytes (CTL) to Enhance in Vivo Safety and Persistency". Blood 118(21), p. 644.

* cited by examiner

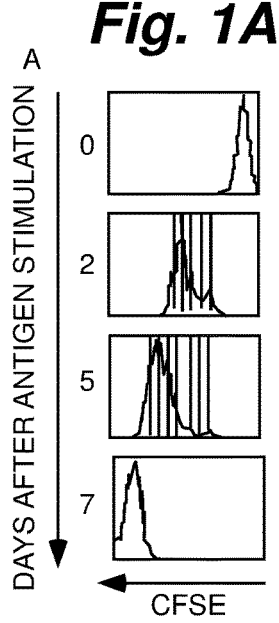
Fig. 1A
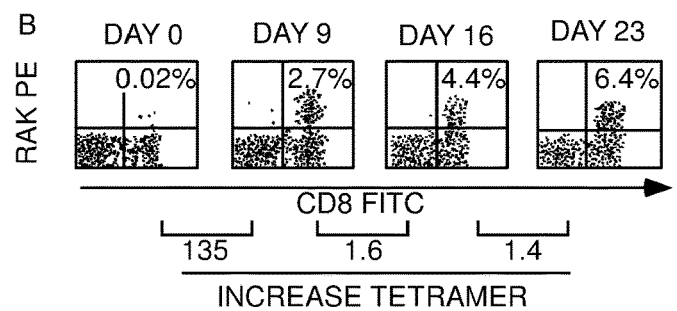
Fig. 1B
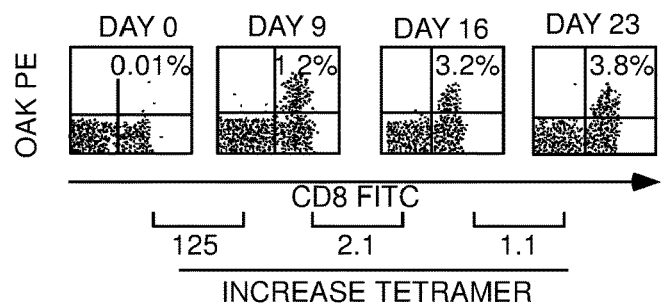
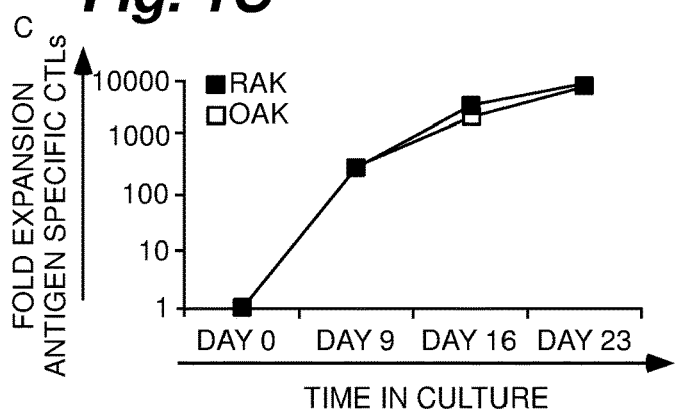
Fig. 1C

Fig. 2

| EXPECTED AND OBSERVED CTL EXPANSION | | | | | | | |
|---|---|---|---|---|---|---|---|
| CELL DOUBLING | 1 | 2 | 3 | 4 | 5 | 6 | 7 |
| EXPECTED FOLD EXPANSION | 2 | 4 | 8 | 16 | 32 | 64 | 128 |
| OBSERVED FOLD EXPANSION (DAY 0 TO 9) | | | | | | | 258 RANGE (48 TO 409) |
| OBSERVED FOLD EXPANSION (DAY 9 TO 16) | | | | | | | 5.7 RANGE (2.2 TO 10.6) |
| OBSERVED FOLD EXPANSION (DAY 16 TO 23) | | | | | | | 4.3 RANGE (4.1 TO 14.9) |

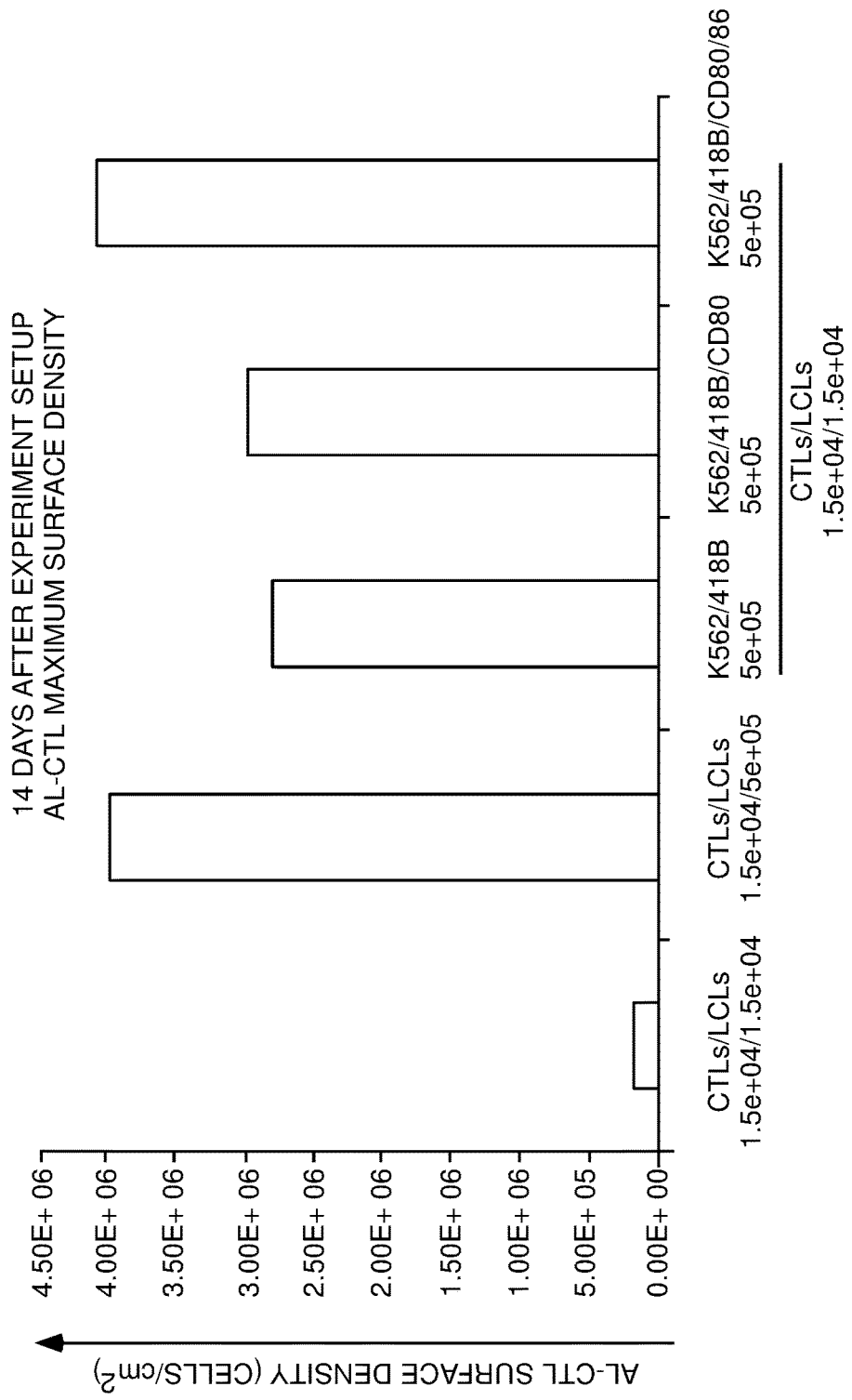

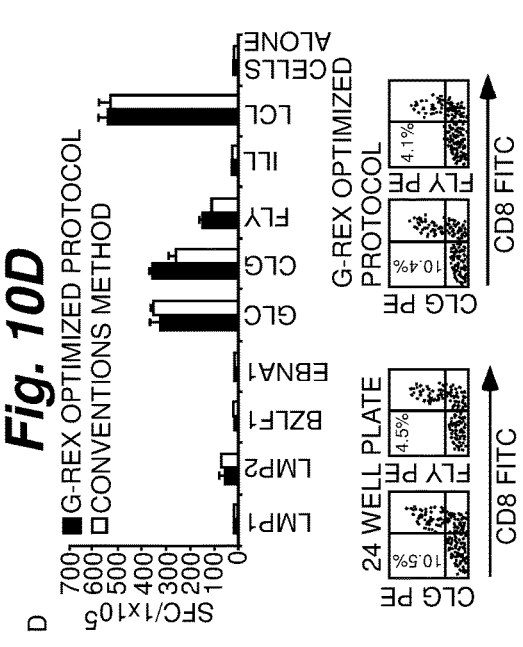
*Fig. 10A*
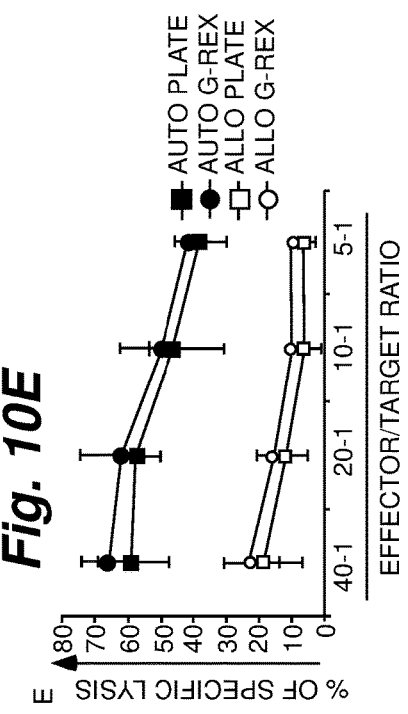
*Fig. 10D*
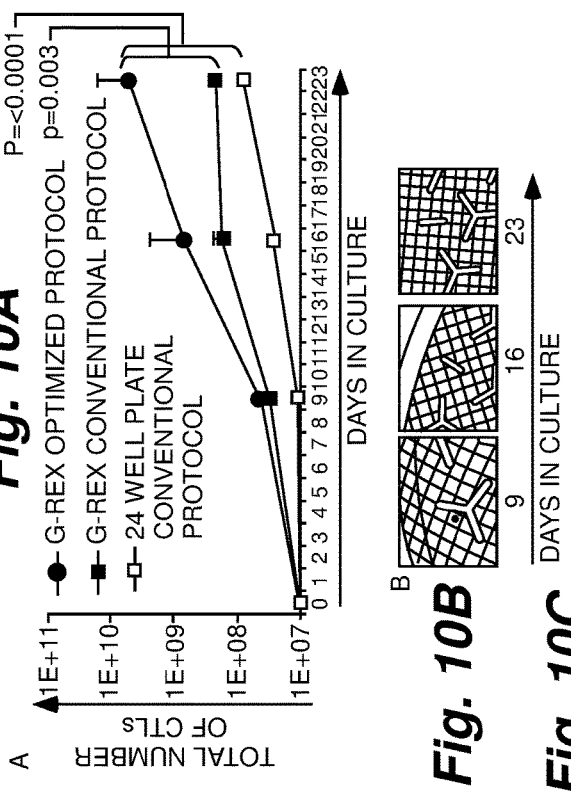
*Fig. 10B*
*Fig. 10C*
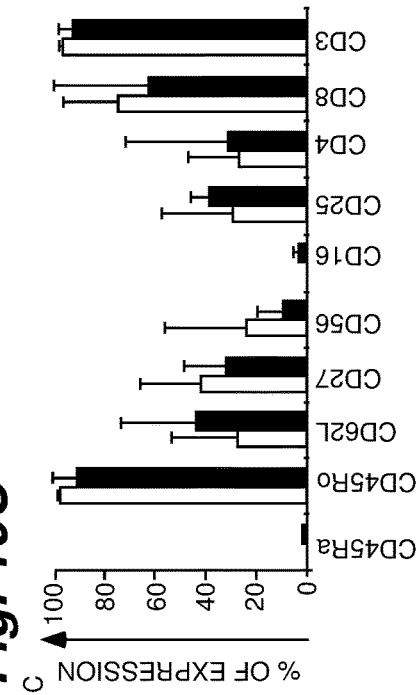
*Fig. 10E*

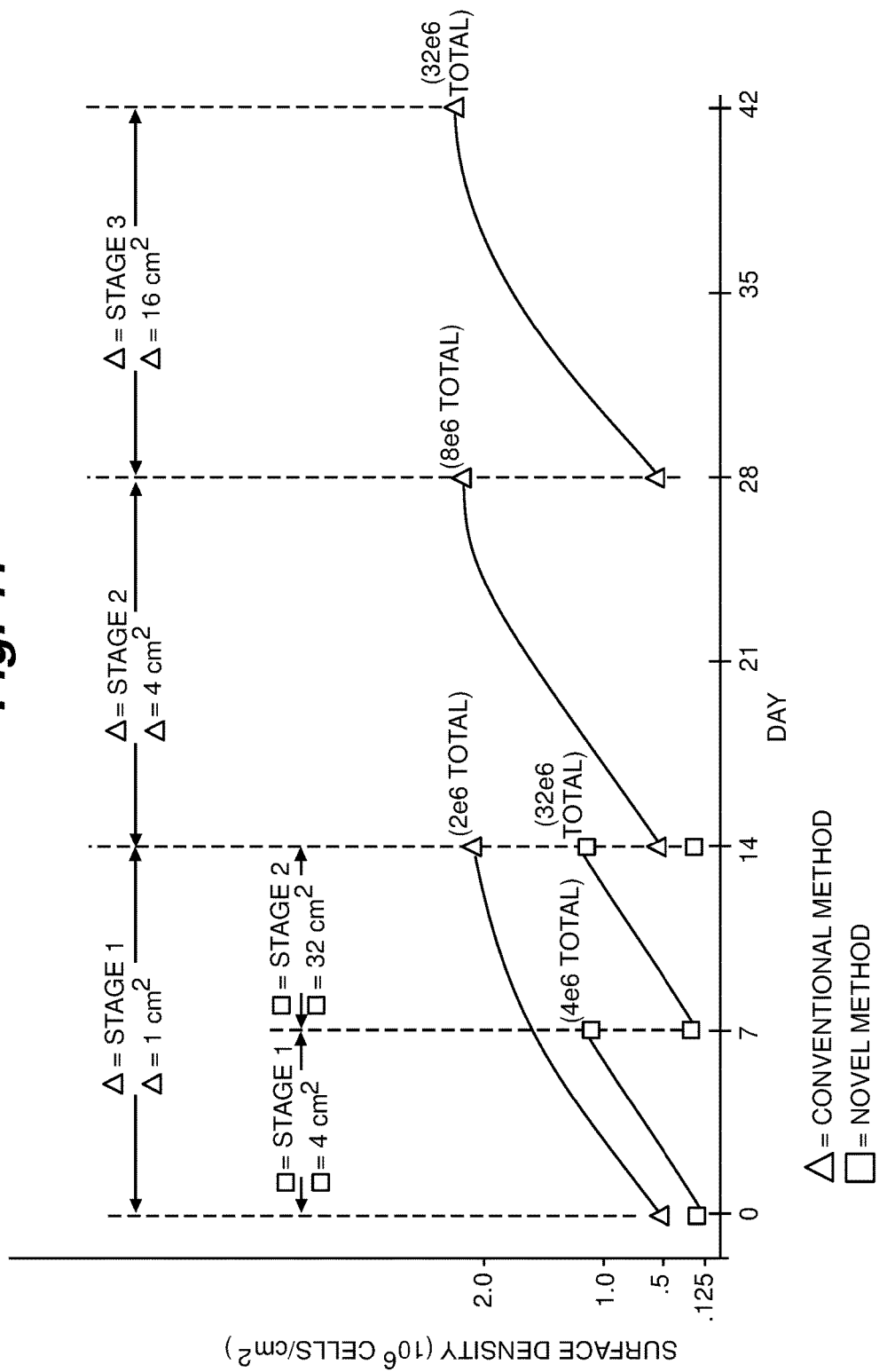

Fig. 15

| | | | CONVENTIONAL | | |
|---|---|---|---|---|---|
| CYCLE | 1 | 2 | 3 | 4 | 5 |
| DAYS PER CYCLE | 7 | 7 | 7 | 7 | 7 |
| CUMULATIVE DAYS | 7 | 14 | 21 | 28 | 35 |
| SURFACE AREA (CM$^2$) | 4 | 16 | 64 | 256 | 1024 |
| STARTING SURFACE DENSITY (CELLS/CM$^2$) | 1 | 1 | 1 | 1 | 1 |
| FINAL SURFACE DENSITY (CELLS/CM$^2$) | 2 | 2 | 2 | 2 | 2 |
| CELLS PRODUCED (x10$^6$) | 8 | 32 | 128 | 512 | 2048 |
| | | | NOVEL | | |
| CYCLE | 1 | 2 | 3 | | |
| DAYS PER CYCLE (APPROX.) | 9.5 | 9.5 | 15.0 | | |
| CUMULATIVE DAYS | 9.5 | 19.0 | 34.0 | | |
| SURFACE AREA (CM$^2$) | 8 | 625 | 46875 | | |
| STARTING SURFACE DENSITY (CELLS/CM$^2$) | 0.06 | 0.06 | 0.06 | | |
| FINAL SURFACE DENSITY (CELLS/CM$^2$) | 4.50 | 4.50 | 4.50 | | |
| CELLS PRODUCED (x10$^6$) | 38 | 2813 | 210938 | | |

Fig. 16

| | | CONVENTIONAL | | | | |
|---|---|---|---|---|---|---|
| CYCLE | 1 | 2 | 3 | 4 | 5 | |
| DAYS PER CYCLE | 7 | 7 | 7 | 7 | 7 | |
| CUMULATIVE DAYS | 7 | 14 | 21 | 28 | 35 | |
| SURFACE AREA (CM$^2$) | 4 | 16 | 64 | 256 | 1024 | |
| STARTING SURFACE DENSITY (CELLS/CM$^2$) | 1 | 1 | 1 | 1 | 1 | |
| FINAL SURFACE DENSITY (CELLS/CM$^2$) | 2 | 2 | 2 | 2 | 2 | |
| CELLS PRODUCED (×10$^6$) | 8 | 32 | 128 | 512 | 2048 | |

| | | NOVEL | | | | |
|---|---|---|---|---|---|---|
| CYCLE | 1 | 2 | 3 | | | |
| DAYS PER CYCLE (APPROX.) | 9.5 | 9.5 | 15.0 | | | |
| CUMULATIVE DAYS | 9.5 | 19.0 | 34.0 | | | |
| SURFACE AREA (CM$^2$) | 8 | 625 | 4018 | | | |
| STARTING SURFACE DENSITY (CELLS/CM$^2$) | 0.06 | 0.06 | 0.70 | | | |
| FINAL SURFACE DENSITY (CELLS/CM$^2$) | 4.50 | 4.50 | 7.50 | | | |
| CELLS PRODUCED (×10$^6$) | 38 | 2813 | 30134 | | | |

Fig. 17A

| ROW | | | DAY 0 | DAY 4 | DAY 8 | DAY 11 |
|---|---|---|---|---|---|---|
| 1 | SURFACE DENSITY ON DAY 0 (cells/cm²) | 1.00E+06 | | | | |
| 2 | SURFACE AREA OF GROWTH SURFACE (cm²) | | 100 | 100 | 100 | 100 |
| 3 | MEDIUM VOLUME (ml) | | 1000 | 1000 | 1000 | 1000 |
| 4 | RATIO OF MEDIUM VOLUME TO GROWTH SURFACE AREA (ml/cm²) | | 10 | 10 | 10 | 10 |
| 5 | MEDIA HEIGHT (cm) | | 10 | 10 | 10 | 10 |
| 6 | SURFACE DENSITY (cells/cm²) | | 1.00E+06 | 4.71E+06 | 9.79E+06 | 9.73E+06 |
| 7 | CELL DENSITY (cells/ml) | | 1.00E+05 | 4.71E+05 | 9.79E+05 | 9.73E+05 |
| 8 | GLUCOSE CONCENTRATION (mg/dl) | 240 | 240 | 112 | 56 | 0 |
| 9 | GLUCOSE CONSUMPTION IN (mg/ml) | | 0 | 128 | 184 | 240 |
| 10 | PREDICTED CELL NUMBER BY USE OF GLUCOSE | | 0.00E+00 | 6.40E+08 | 9.20E+08 | 1.20E+09 |
| 11 | VIABILITY | | 100% | 100% | 99% | 90% |
| 12 | TOTAL LIVE CELLS AS DETERMINED BY HEMOCYTOMETER COUNT | | 1.00E+08 | 4.71E+08 | 9.79E+08 | 9.73E+08 |

Fig. 17B

| ROW | | DAY 0 | DAY 0 | DAY 4 | DAY 8 | DAY 11 |
|---|---|---|---|---|---|---|
| 1 | SURFACE DENSITY ON DAY 0 (cells/cm²) | 5.00E + 05 | | | | |
| 2 | SURFACE AREA OF GROWTH SURFACE (cm²) | | 100 | 100 | 100 | 100 |
| 3 | MEDIUM VOLUME (ml) | | 1000 | 1000 | 1000 | 1000 |
| 4 | RATIO OF MEDIUM VOLUME TO GROWTH SURFACE AREA (ml/cm²) | | 10 | 10 | 10 | 10 |
| 5 | MEDIA HEIGHT (cm) | | 10 | 10 | 10 | 10 |
| 6 | SURFACE DENSITY (cells/cm²) | | 5.00E + 05 | 3.23E + 06 | 8.60E + 06 | 9.53E + 06 |
| 7 | CELL DENSITY (cells/ml) | | 5.00E + 04 | 3.23E + 05 | 8.60E + 05 | 9.53E + 05 |
| 8 | GLUCOSE CONCENTRATION (mg/dl) | 240 | 240 | 132 | 76 | 0 |
| 9 | GLUCOSE CONSUMPTION IN (mg/ml) | | 0 | 108 | 164 | 240 |
| 10 | PREDICTED CELL NUMBER BY USE OF GLUCOSE | | 0.00E + 00 | 5.40E + 08 | 8.20E + 08 | 1.20E + 09 |
| 11 | VIABILITY | | 100% | 100% | 100% | 91% |
| 12 | TOTAL LIVE CELLS AS DETERMINED BY HEMOCYTOMETER COUNT | | 5.00E + 07 | 3.23E + 08 | 8.60E + 08 | 9.53E + 08 |

Fig. 17C

| ROW | | DAY 0 | DAY 4 | DAY 8 | DAY 11 |
|---|---|---|---|---|---|
| 1 | SURFACE DENSITY ON DAY 0 (cells/cm$^2$) | 2.50E + 05 | | | |
| 2 | SURFACE AREA OF GROWTH SURFACE (cm$^2$) | 100 | 100 | 100 | 100 |
| 3 | MEDIUM VOLUME (ml) | 1000 | 1000 | 1000 | 1000 |
| 4 | RATIO OF MEDIUM VOLUME TO GROWTH SURFACE AREA (ml/cm$^2$) | 10 | 10 | 10 | 10 |
| 5 | MEDIA HEIGHT (cm) | 10 | 10 | 10 | 10 |
| 6 | SURFACE DENSITY (cells/cm$^2$) | 2.50E + 05 | 3.02E + 06 | 7.53E + 06 | 1.02E + 07 |
| 7 | CELL DENSITY (cells/ml) | 2.50E + 04 | 3.02E + 05 | 7.53E + 05 | 1.02E + 06 |
| 8 | GLUCOSE CONCENTRATION (mg/dl) | 240 | 134 | 98 | 0 |
| 9 | GLUCOSE CONSUMPTION IN (mg/ml) | 0 | 106 | 142 | 240 |
| 10 | PREDICTED CELL NUMBER BY USE OF GLUCOSE | 0.00E + 00 | 5.30E + 08 | 7.10E + 08 | 1.20E + 09 |
| 11 | VIABILITY | 100% | 100% | 100% | 94% |
| 12 | TOTAL LIVE CELLS AS DETERMINED BY HEMOCYTOMETER COUNT | 2.50E + 07 | 3.02E + 08 | 7.53E + 08 | 1.02E + 09 |

Fig. 17D

| ROW | | DAY 0 | DAY 4 | DAY 8 | DAY 11 |
|---|---|---|---|---|---|
| 1 | SURFACE DENSITY ON DAY 0 (cells/cm²) | 1.25E+05 | | | |
| 2 | SURFACE AREA OF GROWTH SURFACE (cm²) | 100 | 100 | 100 | 100 |
| 3 | MEDIUM VOLUME (ml) | 1000 | 1000 | 1000 | 1000 |
| 4 | RATIO OF MEDIUM VOLUME TO GROWTH SURFACE AREA (ml/cm²) | 10 | 10 | 10 | 10 |
| 5 | MEDIA HEIGHT (cm) | 10 | 10 | 10 | 10 |
| 6 | SURFACE DENSITY (cells/cm²) | 1.25E+05 | 2.65E+06 | 6.55E+06 | 9.88E+06 |
| 7 | CELL DENSITY (cells/ml) | 1.25E+04 | 2.65E+05 | 6.55E+05 | 9.88E+05 |
| 8 | GLUCOSE CONCENTRATION (mg/dl) | 240 | 176 | 111 | 18 |
| 9 | GLUCOSE CONSUMPTION IN (mg/ml) | 0 | 64 | 129 | 222 |
| 10 | PREDICTED CELL NUMBER BY USE OF GLUCOSE | 0.00E+00 | 3.20E+08 | 6.45E+08 | 1.11E+09 |
| 11 | VIABILITY | 100% | 100% | 100% | 98% |
| 12 | TOTAL LIVE CELLS AS DETERMINED BY HEMOCYTOMETER COUNT | 1.25E+07 | 2.65E+08 | 6.55E+08 | 9.88E+08 |

Fig. 17E

| ROW | | | DAY 0 | DAY 4 | DAY 8 | DAY 11 |
|---|---|---|---|---|---|---|
| 1 | SURFACE DENSITY ON DAY 0 (cells/cm²) | 6.25E + 04 | | | | |
| 2 | SURFACE AREA OF GROWTH SURFACE (cm²) | | 100 | 100 | 100 | 100 |
| 3 | MEDIUM VOLUME (ml) | | 1000 | 1000 | 1000 | 1000 |
| 4 | RATIO OF MEDIUM VOLUME TO GROWTH SURFACE AREA (ml/cm²) | | 10 | 10 | 10 | 10 |
| 5 | MEDIA HEIGHT (cm) | | 10 | 10 | 10 | 10 |
| 6 | SURFACE DENSITY (cells/cm²) | | 6.25E + 04 | 4.00E + 05 | 1.24E + 06 | 1.63E + 06 |
| 7 | CELL DENSITY (cells/ml) | | 6.25E + 03 | 4.00E + 04 | 1.24E + 05 | 1.63E + 05 |
| 8 | GLUCOSE CONCENTRATION (mg/dl) | 240 | 240 | 232 | 202 | 184 |
| 9 | GLUCOSE CONSUMPTION IN (mg/ml) | | 0 | 8 | 38 | 56 |
| 10 | PREDICTED CELL NUMBER BY USE OF GLUCOSE | | 0.00E + 00 | 4.00E + 07 | 1.90E + 08 | 2.80E + 08 |
| 11 | VIABILITY | | 100% | 100% | 100% | 100% |
| 12 | TOTAL LIVE CELLS AS DETERMINED BY HEMOCYTOMETER COUNT | | 6.25E + 06 | 4.00E + 07 | 1.24E + 08 | 1.63E + 08 |

Fig. 19A

| ROW | | DAY 0 | DAY 4 | DAY 8 | DAY 11 |
|---|---|---|---|---|---|
| 1 | SURFACE DENSITY ON DAY 0 (cells/cm²) | 1.25E+05 | | | |
| 2 | SURFACE AREA OF GROWTH SURFACE (cm²) | 100 | 100 | 100 | 100 |
| 3 | MEDIUM VOLUME IN ml | 1000 | 1000 | 1000 | 1000 |
| 4 | RATIO OF MEDIUM VOLUME TO GROWTH SURFACE AREA (mls/cm²) | 10 | 10 | 10 | 10 |
| 5 | MEDIA HEIGHT (cm) | 10 | 10 | 10 | 10 |
| 6 | SURFACE DENSITY (cells/cm²) | 1.25E+05 | 2.65E+05 | 6.55E+06 | 9.88E+06 |
| 7 | CELL DENSITY (cells/ml) | 1.25E+04 | 2.65E+04 | 6.55E+05 | 9.88E+05 |
| 8 | GLUCOSE CONCENTRATION (mg/dl) | 240 | 176 | 111 | 18 |
| 9 | GLUCOSE CONSUMPTION (mg/ml) | 0 | 64 | 129 | 222 |
| 10 | PREDICTED CELL NUMBER BY USE OF GLUCOSE | 0.00E+00 | 3.00E+08 | 6.19E+08 | 1.07E+09 |
| 11 | VIABILITY | 100% | 100% | 100% | 98% |
| 12 | TOTAL LIVE CELLS | 1.25E+07 | 2.65E+08 | 6.55E+08 | 9.88E+08 |
| ROW | | DAY 0 | DAY 4 | DAY 8 | DAY 11 |
| 1 | SURFACE DENSITY ON DAY 0 (cells/cm²) | 1.25E+05 | | | |
| 2 | SURFACE AREA OF GROWTH SURFACE (cm²) | 100 | 100 | 100 | 100 |
| 3 | MEDIUM VOLUME IN ml | 1000 | 1000 | 1000 | 1000 |
| 4 | RATIO OF MEDIUM VOLUME TO GROWTH SURFACE AREA (mls/cm²) | 10 | 10 | 10 | 10 |
| 5 | MEDIA HEIGHT (cm) | 10 | 10 | 10 | 10 |
| 6 | SURFACE DENSITY (cells/cm²) | 1.25E+05 | 5.13E+06 | 9.26E+06 | 1.05E+07 |
| 7 | CELL DENSITY (cells/ml) | 1.25E+04 | 5.13E+05 | 9.26E+05 | 1.05E+06 |
| 8 | GLUCOSE CONCENTRATION (mg/dl) | 475 | 374 | 287 | 256 |
| 9 | GLUCOSE CONSUMPTION (mg/ml) | 0 | 107 | 193 | 219 |
| 10 | PREDICTED CELL NUMBER BY USE OF GLUCOSE | 0.00E+00 | 5.13E+08 | 9.20E+08 | 1.00E+09 |
| 11 | VIABILITY | 100% | 100% | 100% | 98% |
| 12 | TOTAL LIVE CELLS | 1.25E+07 | 5.13E+08 | 9.26E+08 | 1.05E+09 |

Fig. 21

CMV-CTL POPULATION EXPANSION

| ROW | | DAY 0 | DAY 9 | DAY 16 |
|---|---|---|---|---|
| 1 | SURFACE DENSITY OF PBMCs AT CULTURE ONSET (cells/cm2) | 5.00E+05 | | |
| 2 | SURFACE DENSITY OF CELL COMPOSITION (cells/cm2) | 5.00E+05 | 1.32E+06 | 2.21E+08 |
| 3 | PERCENTAGE OF ANTIGEN SPECIFIC T CELLS IN THE CELL COMPOSITION (%) | 0.8 | 27.9 | 48.7 |
| 4 | ENRICHMENT OF ANTIGEN SPECIFIC T CELLS (CMV SPECIFIC T CELLS) | 0 | 34.88 | 1.75 |
| 5 | PERCENTAGE OF NON SPECIFIC T CELLS IN THE CELL COMPOSITION | 99.2 | 72.1 | 51.3 |
| 6 | TOTAL NUMBER OF CELLS IN CULTURE | 5.00E+07 | 1.32E+08 | 2.21E+10 |
| 7 | FOLD INCREASE IN CELL COMPOSITION POPULATION EXPANSION | 0 | 2.64E+00 | 442 |
| 8 | FOLD INCREASE IN CELL IN CMV SPECIFIC POPULATION | 0 | 69.7 | 69.8 |
| 9 | AREA OF GROWTH SURFACE (cm2) | 100 | 100 | 100 |
| 10 | MEDIUM VOLUME (ml) | 1000 | 1000 | 1000 |
| 11 | MEDIA HEIGHT (cm) | 10 | 10 | 10 |
| 12 | CELL DENSITY (cells/ml) | 5.00E+04 | 1.32E+05 | 2.21E+07 |
| 13 | RATIO OF MEDIUM VOLUME TO GROWTH SURFACE AREA (ml/cm2) | 10 | 10 | 10 |
| 14 | GLUCOSE CONCENTRATION | 240 | 110 | 19 |
| 15 | GLUCOSE CONSUMPTION | 0 | 130 | 221 |
| 16 | PREDICTED CELL NUMBER BY USE OF GLUCOSE | 0 | 1.30E+08 | 2.21E+08 |
| 18 | TOTAL LIVE CELLS AS DETERMINED BY HEMOCYTOMETER COUNT | 5.00E+07 | 1.32E+08 | 2.21E+08 |
| 19 | PERCENTAGE DIFFERENCE BETWEEN PREDICTED POP. AND HEMOCYTOMETER COUNTS | | 1.54% | 0.00% |

Fig. 23A

| ROW | EVALUATION A | DAY 0 | DAY 4 | DAY 8 | DAY 11 |
|---|---|---|---|---|---|
| 1 | SURFACE DENSITY ON DAY 0 (cells/cm$^2$) OF CAR T CELLS | 2.50E+05 | | | |
| 2 | SURFACE DENSITY ON DAY 0 (cells/cm$^2$) OF APC (K562-PSCA/CD80/41BB) | 5.00E+05 | 1.00E+04 | 0.00E+00 | 0.00E+00 |
| 3 | TOTAL SURFACE DENSITY ON DAY 0 (cells/cm$^2$) | 7.50E+05 | | | |
| 4 | SURFACE AREA OF GROWTH SURFACE (cm$^2$) | 100 | 100 | 100 | 100 |
| 5 | MEDIUM VOLUME (ml) | 1000 | 1000 | 1000 | 1000 |
| 6 | RATIO OF MEDIUM VOLUME TO GROWTH SURFACE AREA (ml/cm$^2$) | 10 | 10 | 10 | 10 |
| 7 | MEDIA HEIGHT (cm) | 10 | 10 | 10 | 10 |
| 8 | SURFACE DENSITY OF CAR T CELLS (cells/cm$^2$) | 2.50E+05 | 1.10E+06 | 1.80E+07 | 2.46E+07 |
| 9 | CELL DENSITY OF CAR T CELLS (cells/cm$^2$) | 2.50E+04 | 1.10E+05 | 1.80E+06 | 2.46E+06 |
| 10 | GLUCOSE CONCENTRATION (mg/dl) | 286 | 176 | 106 | 46 |
| 11 | GLUCOSE CONSUMPTION IN (mg/dl) | 0 | -176 | -106 | -46 |
| 12 | PREDICTED CELL NUMBER BY USE OF GLUCOSE | 0 | 1.10E+08 | 1.80E+09 | 2.40E+09 |
| 13 | VIABILITY | 100 | 94 | 100 | 100 |
| 14 | TOTAL LIVE CELLS AS DETERMINED BY HEMOCYTOMETER COUNT | 2.50E+07 | 1.10E+08 | 1.80E+09 | 2.46E+09 |
| 15 | TOTAL LIVE CELLS FOLD EXPANSION | 0 | 4.40E+00 | 7.20E+01 | 9.84E+01 |
| 16 | CAR EXPRESSION | 40% | 42% | 68% | 80% |
| 17 | FOLD EXPANSION OF CAR T CELLS | | | | 1.97E+02 |

Fig. 23B

| ROW | EVALUATION B | DAY 0 | DAY 4 | DAY 8 | DAY 11 |
|---|---|---|---|---|---|
| 1 | SURFACE DENSITY ON DAY 0 (cells/cm²) OF CAR T CELLS | 2.50E+05 | | | |
| 2 | SURFACE DENSITY ON DAY 0 (cells/cm²) OF APC (K562-PSCA/CD80/41BB) | NONE | | | |
| 3 | TOTAL SURFACE DENSITY ON DAY 0 (cells/cm²) | 2.50E+05 | | | |
| 4 | SURFACE AREA OF GROWTH SURFACE (cm²) | 100 | 100 | 100 | 100 |
| 5 | MEDIUM VOLUME (ml) | 1000 | 1000 | 1000 | 1000 |
| 6 | RATIO OF MEDIUM VOLUME TO GROWTH SURFACE AREA (ml/cm²) | 10 | 10 | 10 | 10 |
| 7 | MEDIA HEIGHT (cm) | 10 | 10 | 10 | 10 |
| 8 | SURFACE DENSITY OF CAR T CELLS (cells/cm²) | 2.50E+05 | 5.00E+05 | 2.80E+06 | 5.40E+06 |
| 9 | CELL DENSITY OF CAR T CELLS (cells/cm²) | 2.50E+04 | 5.00E+04 | 2.80E+05 | 5.40E+05 |
| 10 | GLUCOSE CONCENTRATION (mg/dl) | 286 | | | |
| 11 | GLUCOSE CONSUMPTION IN (mg/dl) | | | | |
| 12 | PREDICTED CELL NUMBER BY USE OF GLUCOSE | | 0 | | |
| 13 | VIABILITY | 100 | 100 | 100 | 100 |
| 14 | TOTAL LIVE CELLS AS DETERMINED BY HEMOCYTOMETER COUNT | 2.50E+07 | 5.00E+07 | 2.80E+08 | 5.40E+08 |
| 15 | TOTAL LIVE CELLS FOLD EXPANSION | | 2.00E+00 | 1.12E+01 | 2.16E+01 |
| 16 | CAR EXPRESSION | 40% | 40% | 40% | 40% |
| 17 | FOLD EXPANSION OF CAR T CELLS | | | | 2.16E+01 |

Fig. 23C

| ROW | EVALUATION C | DAY 0 | DAY 4 | DAY 8 | DAY 11 |
|---|---|---|---|---|---|
| 1 | SURFACE DENSITY ON DAY 0 (cells/cm$^2$) OF CAR T CELLS | 2.50E+05 | | | |
| 2 | SURFACE DENSITY ON DAY 0 (cells/cm$^2$) OF APC (K562-PSCA/CD80/41BB) | 5.00E+05 | 1.00E+04 | 0.00E+00 | 0.00E+00 |
| 3 | TOTAL SURFACE DENSITY ON DAY 0 (cells/cm$^2$) | 7.50E+05 | | | |
| 4 | SURFACE AREA OF GROWTH SURFACE (cm$^2$) | 100 | 100 | 100 | 100 |
| 5 | MEDIUM VOLUME (ml) | 200 | 200 | 200 | 200 |
| 6 | RATIO OF MEDIUM VOLUME TO GROWTH SURFACE AREA (ml/cm$^2$) | 2 | 2 | 2 | 2 |
| 7 | MEDIA HEIGHT (cm) | 2 | 2 | 2 | 2 |
| 8 | SURFACE DENSITY OF CAR T CELLS (cells/cm$^2$) | 2.50E+05 | 4.30E+05 | 3.80E+05 | 1.80E+05 |
| 9 | CELL DENSITY OF CAR T CELLS (cells/cm$^2$) | 2.50E+04 | 4.30E+04 | 3.80E+04 | 1.80E+04 |
| 10 | GLUCOSE CONCENTRATION (mg/dl) | 286 | 46 | 0 | 0 |
| 11 | GLUCOSE CONSUMPTION IN (mg/dl) | 0 | 240 | 286 | 286 |
| 12 | PREDICTED CELL NUMBER BY USE OF GLUCOSE | 0 | 4.80E+07 | 4.80E+08 | 4.80E+08 |
| 13 | VIABILITY | 100 | 94 | 75 | 36 |
| 14 | TOTAL LIVE CELLS AS DETERMINED BY HEMOCYTOMETER COUNT | 2.50E+07 | 4.30E+07 | 3.80E+07 | 1.80E+07 |
| 15 | TOTAL LIVE CELLS FOLD EXPANSION | 0 | 1.72E+00 | 1.52E+00 | 7.20E-01 |
| 16 | CAR EXPRESSION | 40% | 42% | 68% | 80% |
| 17 | FOLD EXPANSION OF CAR T CELLS | | | | 1.44E+00 |

DAY 0

DAY 9

| | DAY 0 | DAY 10 | |
|---|---|---|---|
| CAR-PSCA | 25 MILLION T-CELLS | CONVENTIONAL CULTUREWARE | G-REX (+50MILLIONAPCs) |
| | DONOR1 | 250 | 2460 |
| | DONOR2 | 246 | 2200 |
| | DONOR3 | 240 | 2300 |

| | DAY 0 | DAY 10 | |
|---|---|---|---|
| CAR-Muc1 | 25 MILLION T-CELLS | CONVENTIONAL CULTUREWARE | G-REX (+50MILLIONAPCs) |
| | DONOR1 | 236 | 2120 |
| | DONOR2 | 240 | 2260 |
| | DONOR3 | 225 | 1980 |

METHODS OF CELL CULTURE FOR ADOPTIVE CELL THERAPY

RELATED APPLICATION

The present application is a continuation of U.S. patent application Ser. No. 14/579,373, now U.S. Pat. No. 9,567,565, entitled "IMPROVED METHODS OF CELL CULTURE FOR ADOPTIVE CELL THERAPY", filed 5 Dec. 22, 2014, which is a divisional of U.S. patent application Ser. No. 13/475,700, now U.S. Pat. No. 8,956,860 entitled "IMPROVED METHODS OF CELL CULTURE FOR ADOPTIVE CELL THERAPY,", filed May 18, 2012, which is a continuation-in-part of U.S. patent Ser. No. 12/963,597, filed Dec. 8, 2010, now U.S. Pat. No. 8,809,050, issued Aug. 19, 2014, entitled "IMPROVED METHODS OF CELL CULTURE FOR ADOPTIVE CELL THERAPY," 10 (hereinafter the "parent case") which claims the benefit of U.S. Provisional Application No. 61/267,761, filed Dec. 8, 2009, also entitled "IMPROVED METHODS OF CELL CULTURE FOR ADOPTIVE CELL THERAPY", which are herein incorporated by reference in their entirety.

FIELD OF THE INVENTION

The present invention relates generally to methods of culturing cells, and more specifically to culturing cells for cell therapy.

BACKGROUND

Cell culture is major contributor to the cost and complexity of cell therapy. With current methods, the process of culturing the cells is time consuming and expensive. Typically, to produce a large number of cells, an in vitro culture process is undertaken that proceeds in stages. At the earliest stage, the desired cells are a relatively small population within a composition of cells that are placed into cell culture devices. In this stage, the composition of cells typically includes the source of the desired cells (such as peripheral blood mononuclear cells), feeder cells that stimulate growth of the desired cells, and/or antigen presenting. Culture devices and methods that allow the medium that cells reside in to be in a generally undisturbed state are favored since the cells remain relatively undisturbed. Such devices include standard tissue culture plates, flasks, and bags. The culture progresses in stages generally consisting of allowing the cell composition to deplete the medium of growth substrates such as glucose, removing the spent medium, replacing the spent medium with fresh medium, and repeating the process until the desired quantity of desired cells is obtained. Often, the cell composition is moved to other devices to initiate a new stage of production as the desired cell population increases and additional growth surface is needed. However, with conventional methods, the rate of population growth of the desired cells slows as the population of cells upon the growth surface increases. The end result is that it is very time consuming and complicated to produce a sizable population of desired cells.

State of the art production methods for generating T lymphocytes with antigen specificity to Epstein Barr virus (EBV-CTLs) provide an example of production complexity. The conventional method for optimal expansion of EBV-CTLs uses standard 24-well tissue culture plates, each well having 2 cm$^2$ of surface area for cells to reside upon and the medium volume restricted to 1 ml/cm$^2$ due to gas transfer requirements. The culture process begins by placing a cell composition comprised of PBMC (peripheral blood mononuclear cells) in the presence of an irradiated antigen presenting cell line, which may be a lymphoblastoid cell line (LCL), at a surface density (i.e. cells/cm$^2$ of growth surface) ratio of about 40:1 with about 1×10$^6$ PBMC/cm$^2$ and 2.5×10$^4$ irradiated antigen presenting cells/cm$^2$. That instigates the population of EBV-CTLs within the cell composition to expand in quantity. After 9 days, EBV-CTLs are selectively expanded again in the presence of irradiated antigen presenting LCL at a new surface density ratio of 4:1, with a minimum surface density of about 2.5×10$^5$ EBV-CTL/cm$^2$. Medium volume is limited to a maximum ratio of 1 ml/cm$^2$ of growth surface area to allow oxygen to reach the cells, which limits growth solutes such as glucose. As a result, the maximum surface density that can be achieved is about 2×10$^6$ EBV-CTL/cm$^2$. Thus, the maximum weekly cell expansion is about 8-fold (i.e. 2×10$^6$ EBV-CTL/cm$^2$ divided by 2.5×10$^5$ EBV-CTL/cm$^2$) or less. Continued expansion of EBV-CTLs requires weekly transfer of the EBV-CTLs to additional 24-well plates with antigenic re-stimulation, and twice weekly exchanges of medium and growth factors within each well of the 24-well plate. Because conventional methods cause the rate of EBV-CTL population expansion to slow as EBV-CTL surface density approaches the maximum amount possible per well, these manipulations must be repeated over a long production period, often as long as 4-8 weeks, to obtain a sufficient quantity of EBV-CTLs for cell infusions and quality control measures such as sterility, identity, and potency assays.

The culture of EBV-CTLs is but one example of the complex cell production processes inherent to cell therapy. A more practical way of culturing cells for cell therapy that can reduce production time and simultaneously reduce production cost and complexity is needed.

We have created novel methods that increase the population growth rate throughout production, and by so doing, reduce the complexity and time needed to produce cells.

Primary non-adherent cells such as antigen specific T cells, natural killer cells (NK), regulatory T cells (Treg), tumor infiltrating lymphocytes (TIL), marrow infiltrating lymphocytes (TIL), and islets are often the focus of production. Many production processes aim to increase the population of desired cells, often referred to as effector cells, often in co-culture conditions that rely on other cell types to stimulate growth and/or antigen specificity of the desired cells. The cells used in co-culture are often referred to as feeder cells and/or antigen presenting cells. In some cases, co-cultures transition to expansion of the desired cell population in the absence of feeder and/or antigen presenting cells such as TIL production. Production of antigen presenting cells and/or feeder cells in the absence of effector cells is also prevalent. Also, sometimes culture is intended to maintain health of a cell population as opposed to increasing the population per se, such as islet culture for treatment of diabetes. Thus, culture devices and production processes for cell culture in Adoptive Cell Therapy must deal with many possible production applications.

For Adoptive Cell Therapy to be useful on a wide scale, the cell production process needs to be greatly simplified and made less expensive. However, state of the art devices and methods for production are not capable of making that happen. A brief explanation of why that is the case follows.

Devices currently relied upon extensively in the field of Adoptive Cell Therapy are static cell culture devices, namely cell culture plates, flasks, and gas permeable bags. These static devices are intended to allow cells to reside in proximity of one another during culture in order to facilitate communication between co-cultures and/or allow non co-cultures to remain physically quiescent. The physically undisturbed state is beneficial for a variety of biological reasons as skilled artisans are well aware. Furthermore, static cell culture devices are uncomplicated and do not require constant use of ancillary equipment during their operation to perfuse medium or gas through the device, agitate the medium such as by sparging, stirring or shaking the apparatus, and/or keep cells from settling to the bottom of the device. Thus, static devices are compatible with standard laboratory and cell culture equipment such as incubators, and have minimal or no reliance on ancillary equipment. Although static devices have the described advantages, they also have inherent problems that prevent efficient and practical production of cells for Adoptive Cell Therapy.

Among the inherent problems are the limited height at which medium can reside above the growth surface, ranging from an upper limit of about 0.3 cm in plates and flasks, according to manufacturer's recommendations, to 2.0 cm in gas permeable bags. Thus, plates and flasks have a limited medium volume to growth surface area ratio of no more than 0.3 ml/cm$^2$ and gas permeable bags are constrained to no more than 2.0 ml/cm$^2$. Compounding the design limits of plates, flasks, and bags are the state of the art protocols for their use in the field of Adoptive Cell Therapy, which narrowly constrain cell density to the range of 0.5 to 2.0×10$^6$ cells/ml and which inherently rely on a surface density of at least 0.5×10$^6$ cells/cm$^2$ to initiate culture. These limits lead to a variety of problems that render cell production for Adoptive Cell Therapy impractical, including an excessive amount of devices in the process, an inordinate amount of labor to maintain cultures, a high risk of contamination, and/or long duration of time to produce cells. Bags have unique problems in that routine handling of the bag causes cells to be disturbed from their resting location and distributed into the media.

Alternative devices to the plate, flask, and bag have been introduced in co-pending U.S. Publication Nos. 2005/0106717 A1 to Wilson et al. (hereinafter referred to as Wilson '717) and 2008/0227176 A1 to Wilson (hereinafter referred to as Wilson '176), and alternative methods for culture have been introduced in the parent case which discloses a particularly powerful improvement of cell production process for the field of Adoptive Cell Therapy. Wilson '717 describes various innovative gas permeable devices that allow culture methods to be performed by scale up in the vertical direction, moving beyond the limited medium height and limited medium volume to growth surface area ratios of plates, flasks, and bags to allow more efficient use of physical space. Wilson '176 builds upon Wilson '717 by allowing even more growth area to reside in a given amount of physical space. The parent case discloses discoveries that allow more efficient co-culture of cells commonly used in the field of Adoptive Cell Therapy, including teaching away from state of the art limits relating to cell surface density in order to provide a wide range of unexpected benefits.

The present invention builds upon the parent case with new discoveries that further improve the efficiency and practicality of cell production, particularly for the field of Adoptive Cell Therapy, and builds upon Wilson '717 and Wilson '176 to enable various novel methods disclosed herein.

SUMMARY

It has been discovered that the production of cells for cell therapy can occur in a shorter time period and in a more economical manner than is currently possible by using a staged production process that allows unconventional conditions to periodically be re-established throughout the production process. The unconventional conditions include reduced surface density (i.e. cells/cm$^2$) of desired cells, novel ratios of desired cells to antigen presenting and/or feeder cells, and/or use of growth surfaces comprised of gas permeable material with increased medium volume to surface area ratios.

Embodiments of this invention relate to improved methods of culturing cells for cell therapy applications. They include methods that reduce the time, cost, and complexity needed to generate a desired number of desired cells by use of various novel methods that allow the desired cell population to maintain a higher growth rate throughout the production process relative to conventional methods.

One aspect of the present invention relies on conducting the culture process in stages and establishing conditions at the onset of one or more stages that allow the growth rate of the desired cell population to exceed what is currently possible. At least one stage of culture, and preferably nearly all, establish initial conditions that include the desired cells resting either on non-gas permeable or gas permeable growth surfaces at unconventionally low surface density and at an unconventional ratio of antigen presenting cells (and/or feeder cells) per desired cell. By using the novel embodiments of this aspect of the invention, the desired cell population can experience more doublings in a shorter period of time than allowed by conventional methods, thereby reducing the duration of production.

Another aspect of the present invention relies on conducting the culture process in stages and establishing conditions at the onset of one or more stages such that the growth rate of the desired cell population exceeds what is currently possible. At least one stage of culture, and preferably nearly all, establish conditions that include the desired cells resting on a growth surface comprised of gas permeable material at unconventionally high medium volume to growth surface area ratios. By using the novel embodiments of this aspect of the invention, the desired cell population can experience more doublings in a shorter period of time than is allowed by conventional methods, thereby reducing the duration of production.

Another aspect of the present invention relies on conducting the culture process in stages and establishing conditions of each stage such that the growth rate of the desired cell population exceeds what is currently possible. At least one stage of culture, and preferably nearly all, establish initial conditions that include the desired cells resting on growth surfaces comprised of gas permeable material at unconventionally low surface density (i.e. cells/cm$^2$) with an unconventional ratio of antigen presenting cells (and/or feeder cells) per desired cell and in the presence of unconventionally high medium volume to growth surface area ratios. By using the novel embodiments of this aspect of the invention, the desired cell population can experience more doublings in a shorter period of time than conventional methods allow, thereby reducing the duration of production.

We have discovered additional methods of cell culture that teach away from state of the art methods in the field of Adoptive Cell Therapy and build upon the disclosures of the parent case to make the process of culturing and/or preparing cells more practical and cost effective than current methodologies.

In one embodiment of the present invention using gas permeable cell culture devices to culture cells, cells are capable of initiating outgrowth when residing in a gas permeable device from a state wherein surface density (cells/cm$^2$) and cell density (cells/ml) are reduced below conventional methods.

In another embodiment of the present invention using gas permeable cell culture devices to culture cells, the need to count cells to determine how many cells are in culture at any given time can be replaced by taking a sample of solutes in the medium and using it to predict the population within the culture at any given time.

In another embodiment of the present invention using gas permeable cell culture devices to culture cells, medium volume to growth surface area is increased in order to reduce the frequency of feeding relative to state of the art methods or even eliminate the need to feed the culture altogether after culture onset.

In another embodiment of the present invention using gas permeable cell culture devices to culture cells, medium volume to growth surface area is further increased in order to allow a longer period of time at which a cell population can reside at high viability after reaching its maximum population.

In another embodiment of the present invention, gas permeable cell culture and cell recovery devices are disclosed that are capable of reducing the medium volume in a culture without cell loss, concentrating cells absent the need for centrifugation, and increasing cell density prior to removing cells from the devices.

In another embodiment of the present invention, methods of use for novel gas permeable cell culture and cell recovery devices are disclosed that are capable of reducing the medium volume in a culture without cell loss in order to minimize need to increase the number of devices in culture should an operator choose to feed the culture.

In another embodiment of the present invention using gas permeable cell culture devices to culture cells, methods of rapidly producing CAR T cells and improving killing capacity by use of APCs in culture are disclosed.

In another embodiment of the present invention using gas permeable cell culture devices to culture cells, methods of the present invention are linearly scalable in direct proportion to increase in the surface area of the growth surface.

BRIEF DESCRIPTION OF THE DRAWINGS

The invention may be more completely understood in consideration of the following detailed description of various embodiments of the invention in connection with the accompanying drawings, in which:

FIG. 1A shows the population of antigen-specific T-cells in Example 1 undergoes at least 7 cell doublings after the initial stimulation over the first 7 days.

FIG. 1B shows data demonstrating the magnitude of expansion of a T-cell population within a cell composition over time as determined by tetramer analysis for Example 1.

FIG. 1C the rate of population growth of antigen-specific T-cells diminishes over a 23 day period in Example 1.

FIG. 9 shows an illustrative example in which we experimentally demonstrated that a very low cumulative surface density of desired cells and antigen presenting cells (in this case AL-CTLs and LCLs cells combining to create a cell composition with a surface density of 30,000 cells/cm$^2$) was unable to initiate outgrowth of the AL-CTL population.

FIG. 10A presents data of Example 8 that show how two novel methods of culturing cells produce more cells over a 23 day period than a conventional method.

FIG. 10B shows a photograph of cells cultured in a test fixture in Example 8.

FIG. 10C shows that in Example 8, the two novel methods of culture and the conventional method all produce cells with the same phenotype.

FIG. 10D shows that for Example 8, a representative culture in which T-cells stimulated with EBV peptide epitopes from LMP1, LMP2, BZLF1 and EBNA1 of EBV and stained with HLA-A2-LMP2 peptide pentamers staining showed similar frequencies of peptide-specific T-cells.

FIG. 10E shows that for the novel methods and the conventional method of Example 8, cells maintained their cytolytic activity and specificity and killed autologous EBV- LCL, with low killing of the HLA mismatched EBV-LCL as evaluated by $^{51}$Cr release assays.

FIG. 11 shows a graphical representation of expansion of a desired cell population on a growth surface under the conventional scenario as compared to population expansion of the desired cell type using one aspect of the present invention.

FIG. 15 shows a comparison of each production method depicted in FIG. 14 to demonstrate the power of the novel method and why it is useful to adjust the production protocol at various stages to fully capture the efficiency.

FIG. 16 shows an example of how one could adjust the production protocol in the novel method to gain efficiency as production progresses.

FIG. 17A shows a representative spreadsheet of the experimental conditions at 1.0E+06 cells/cm$^2$ and results.

FIG. 17B shows a representative spreadsheet of the experimental conditions at 0.5E+06 cells/cm$^2$ and results.

FIG. 17C shows a representative spreadsheet of the experimental conditions at 0.25E+06 cells/cm$^2$ and results.

FIG. 17D shows a representative spreadsheet of the experimental conditions at 0.125E+06 cells/cm$^2$ and results.

FIG. 17E shows a representative spreadsheet of the experimental conditions at 0.0625E+06 cells/cm$^2$ and results.

FIG. 19A shows a representative spreadsheet of the experimental conditions and typical results for the culture of K562 cells under equivalent starting conditions except for the glucose concentration.

FIG. 21 shows a spreadsheet that summarizes conditions on day 0, day 9, and day 16 for an experiment that demonstrated the capability of using glucose depletion as a surrogate measure of cell population.

FIG. 23A shows the conditions of Evaluation A at the onset of culture and as the culture progressed.

FIG. 23B shows the conditions of Evaluation B at the onset of culture and as the culture progressed.

FIG. 23C shows the conditions of Evaluation C at the onset of culture and as the culture progressed.

DETAILED DESCRIPTION

Definitions

Figure 3A:
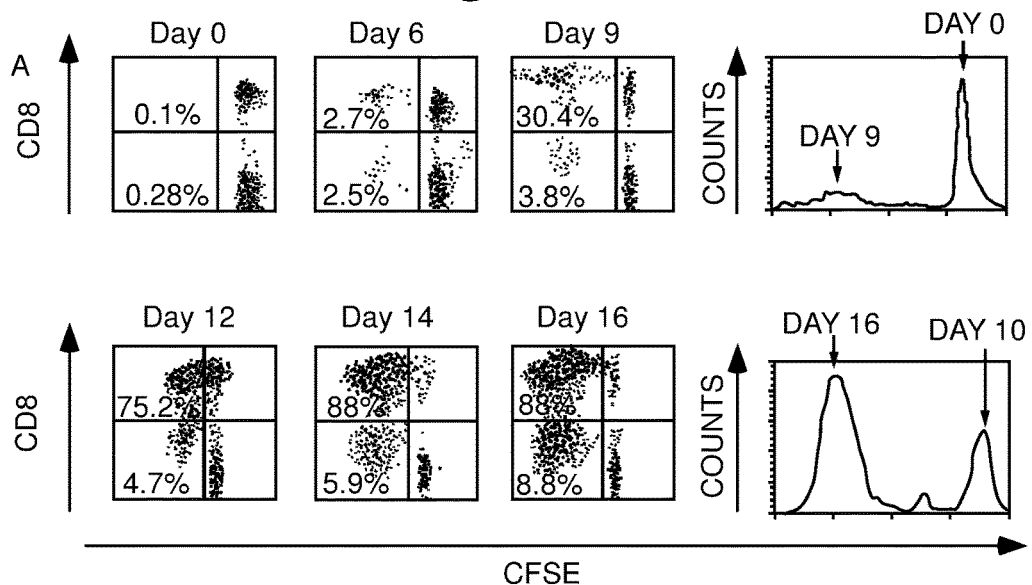
FIG. 3A shows the presence of antigen-specific T-cells following stimulations in Example 2.

Adherent cells: Cell that attach to growth surface
Antigen presenting cells (APC): Cells that act to trigger the desired cells to respond to a particular antigen.
CTL: Cytotoxic T cell
Cell density: The ratio of cells number per unit volume of medium (cells/ml)
Desired cells: The specific type of cell that that the production process aims to expand and/or recover in quantity. Generally the desired cells are non-adherent and examples include regulatory T cells (Treg), natural killer cells (NK), tumor infiltrating lymphocytes (TIL), primary T lymphocytes and a wide variety of antigen specific cells, and many others (all of which can also be genetically modified to improve their function, in-vivo persistence or safety). Cells required for clinical use can be expanded with feeder cells and/or antigen presenting cells that can include PBMC, PHA blast, OKT3 T, B blast, LCLs and K562, (natural or genetically modified to express and antigen and/or epitope as well as co-stimulatory molecules such as 41BBL, OX40, CD80, CD86, HLA, and many others) which may or may not be pulsed with peptide or other relevant antigens.

EBV: Epstein Barr Virus

EBV-CTL: A T-cell that specifically recognized EBV-infected cells or cells expressing or presenting EBV-derived peptides through its T cell surface receptor.

EBV-LCL: Epstein Barr virus transformed B lymphoblastoid cell line.

Feeder cells: Cells that act to cause the desired cells to expand in quantity. Antigen presenting cells can also act as feeder cells in some circumstances.

Growth surface: The area within a culture device upon which cells rest.

Initiating culture: Generally refers to the conditions at the onset of a culture process and/or at the onset of production cycles Medium exchange: Synonymous with feeding the cells and is generally the process by which old medium is replenished with fresh medium PBMCs: Peripheral Blood Mononuclear Cells derived from peripheral blood, which are a source of some of the desired cells and which can act as feeder cells.

Responder (R): A cell that will react to a stimulator cell.

Static cell culture: A method of culturing cells in medium that is not stirred or mixed except for occasions when the culture device is moved from location to location for routine handling and/or when cells are periodically fed with fresh medium and the like. In general, medium in static culture is typically in a quiescent state. It is not subjected to forced movement such as occurs in perfusion systems (in which medium is constantly moved through the vessel), shaker systems in which the culture device is physically shaken to move the medium, stirred systems (in which a stir bar moves within the device to agitate medium and cells), or any other mechanisms or equipment used to force medium to be moved and mixed throughout the duration of culture. Cells gravitate to growth surfaces in the devices where they reside in an undisturbed state except for periods of occasional feeding, at which point the culture is provide with fresh medium by first removing medium and then adding medium, by adding medium without removing medium, or by removing medium and cells and distributing the medium and cells to new devices and adding fresh medium to those devices. Pumps to aid the feeding process are not uncommon. For example gas permeable cell culture bags often rely on gravity or pumps to move fluid to and from them in a closed system manner. The vast majority of the culture duration is one in which cells and medium reside in a quiescent and un-agitated state. This invention is directed to static cell culture methods.

Stimulated: The effect that antigen presenting and/or feeder cells have on the desired cells.

Stimulator (S): A cell that will influence a responder cell.

Surface density: The quantity of cells per unit area of the growth surface within the device upon which the cells rest.

Suspension cells: Cell that do not need to attach to growth surface, synonymous with non-adherent cells In attempting to find novel methods to simplify the production of a desired population of cells for adoptive T cell therapy, a series of experiments were conducted that have that opened the door to more efficient culture of cells for cell therapy applications. Numerous illustrative examples and various aspects of the present invention are described to indicate how the ability to reduce production time and complexity relative to conventional methods can be achieved.

Example 1: Demonstration of Limitations of Conventional Methods

The data of this example demonstrate the limits of conventional culture methods for the production of EBV-CTL in standard 24 well tissue culture plates (i.e. 2 cm² surface area per well) using a medium volume of 2 ml per well (i.e. medium height at 1.0 cm and a medium volume to surface area ratio of 1 ml/cm²).

Stage 1 of Culture, Day 0:

The expansion of an EBV-CTL population was initiated by culturing a cell composition of PBMCs from normal donors (about $1\times10^6$ cells/ml) with antigen presenting gamma-irradiated (40 Gy) autologous EBV-LCLs at a 40:1 ratio (PBMC:LCLs) and a medium volume to growth surface ratio of 1 ml/cm² thereby establishing a cell composition surface density of about $1\times10^6$ cells/cm² in RPMI 1640 supplemented with 45% Click medium (Irvine Scientific, Santa Ana, Calif.), with 2 mM GlutaMAX-I, and 10% FBS.

Stage 2 of Culture, Day 9-16:

On day 9, EBV-CTLs were harvested from the cell composition created in Stage 1, resuspended in fresh medium at a surface density of $0.5\times10^6$ EBV-CTL/cm² and re-stimulated with irradiated autologous EBV-LCLs at a ratio 4:1 CTL:LCL (surface density $0.5\times10^6$ CTL/cm²:$1.25\times10^5$ LCL/cm²). On day 13, 1 ml of the 2 ml medium volume in each well of the 24-well plates was removed and replaced with 1 ml of fresh medium containing recombinant human IL-2 (IL-2) (50 U/mL) (Proleukin; Chiron, Emeryville, Calif.)

Stage 3 of Culture, Day 17-23:

The conditions of Stage 2 were repeated with twice weekly addition of IL-2 and the culture was terminated on day 23. Although the culture was terminated, it could have been continued with additional culture stages that mimicked that of stages 2 and 3.

Cell Lines and Tumor Cells for Use as Target Cells in Cytotoxicity Assays:

BJAB (a B cell lymphoma) and K562 (a chronic erythroid leukemia) were obtained from the American Type Culture Collection (ATCC, Rockville, Md., USA). All cells were maintained in culture with RPMI 1640 medium (GIBCO-BRL, Gaithersburg, Md.) containing 10% heat-inactivated fetal calf serum (FCS), 2 mM L-glutamine, 25 IU/mL penicillin, and 25 mg/mL streptomycin (all from BioWhittaker, Walkersville, Md.). Cells were maintained in a humidified atmosphere containing 5% $CO_2$ at 37° C.

Immunophenotyping:

Cell Surface:

Cells were stained with Phycoerythrin (PE), fluorescein isothiocyanate (FITC), periodin chlorophyll protein (PerCP) and allophycocyanin (APC)-conjugated monoclonal antibodies (MAbs) to CD3, CD4, CD8, CD56, CD16, CD62L, CD45RO, CD45RA, CD27, CD28, CD25, CD44 from Becton-Dickinson (Mountain View, Calif., USA). PE-conjugated tetramers (Baylor College of Medicine) and APC-conjugated pentamers (Proimmune Ltd, Oxford, UK), were used to quantify EBV-CTL precursor frequencies. For cell surface and pentamer staining 10,000 and 100,000 live events, respectively, were acquired on a FACSCalibur flow cytometer and the data analyzed using Cell Quest software (Becton Dickinson).

CFSE Labeling to Measure Cell Division:

To assess the doubling rate of $2\times10^7$ PBMC or EBV-specific CTLs (EBV-CTLs) were washed twice and resuspended in 850 µl 1× phosphate-buffered saline (PBS) containing 0.1% Fetal Bovine Serum (FBS) (Sigma-Aldrich). Prior to staining, an aliquot of carboxy-fluorescein diacetate, succinimidyl ester (CFSE) (10 mM in dimethyl sulfoxide) (Celltrace™ CFSE cell proliferation kit (C34554) Invitrogen) was thawed, diluted 1:1000 with 1×PBS and 150 µl of the dilution was added to the cell suspension (labeling concentration was 1 µM). Cells were incubated with CFSE for 10 minutes at room temperature. Subsequently 1 ml FBS was added to the cell suspension followed by a 10 minute incubation at 37° C. Afterwards cells were washed twice with 1×PBS, counted, and stimulated with antigen as described.

AnnexinV-7-AAD Staining:

To determine the percentage of apoptotic and necrotic cells in our cultures we performed Annexin-7-AAD staining as per manufacturers' instructions (BD Pharmingen™ #559763, San Diego, Calif.). Briefly, EBV-CTL from the 24-well plates or the G-Rex were washed with cold PBS, resuspended in 1× Binding Buffer at a concentration of $1\times10^6$ cells/ml, stained with Annexin V-PE and 7-AAD for 15 minutes at RT (25° C.) in the dark. Following the incubation the cells were analyzed immediately by flow cytometry.

Chromium Release Assay:

We evaluated the cytotoxic activity of EBV-CTLs in standard 4-hour $^{51}$Cr release assay, as previously described. As desired cells we used autologous and HLA class I and II mismatched EBV-transformed lymphoblastoid cell line (EBV-LCL) to measure MHC restricted and unrestricted killing, as well as the K562 cell line to measure natural killer activity. Chromium-labeled desired cells incubated in medium alone or in 1% Triton X-100 were used to determine spontaneous and maximum $^{51}$Cr release, respectively. The mean percentage of specific lysis of triplicate wells was calculated as follows: [(test counts−spontaneous counts)/(maximum counts−spontaneous counts)]×100.

Enzyme-Linked Immunospot (ELIspot) assay: ELIspot analysis was used to quantify the frequency and function of T cells that secreted IFNγ in response antigen stimulation. CTL lines expanded in 24 well plates or in the G-Rex were stimulated with irradiated LCL (40 Gy) or LMP1, LMP2, BZLF1 and EBNA1 pepmixes (diluted to 1 µg/ml) (JPT Technologies GmbH, Berlin, Germany), or EBV peptides HLA-A2 GLCTLVAML=GLC, HLA-A2 CLGGLLTMV=CLG, HLA-A2-FLYALALLL=FLY, and HLA-A29 ILLARLFLY=ILL (Genemed Synthesis, Inc. San Antonio, Tex.), diluted to a final concentration of 204, and CTLs alone served as a negative controls. CTLs were resuspended at $1\times10^6$/ml in ELIspot medium [(RPMI 1640 (Hyclone, Logan, Utah) supplemented with 5% Human Serum (Valley Biomedical, Inc., Winchester, Va.) and 2-mM L-glutamine (GlutaMAX-I, Invitrogen, Carlsbad, Calif.)].

Ninety-six-well filtration plates (MultiScreen, #MAHAS4510, Millipore, Bedford, Mass.) were coated with 10 µg/mL anti-IFN-γ antibody (Catcher-mAB91-DIK, Mabtech, Cincinnati, Ohio) overnight at 4° C., then washed and blocked with ELIspot medium for 1 hour at 37° C. Responder and stimulator cells were incubated on the plates for 20 hours, then the plates were washed and incubated with the secondary biotin conjugated anti-IFN-γ monoclonal antibody (Detector-mAB (7-B6-1-Biotin), Mabtech) followed by incubation with Avidin:biotinylated horseradish peroxidase complex (Vectastain Elite ABC Kit (Standard), #PK6100, Vector Laboratories, Burlingame, Calif.) and then developed with AEC substrate (Sigma, St. Louis, Mo.). Each culture condition was run in triplicate. Plates were sent for evaluation to Zellnet Consulting, New York, N.Y. Spot-forming units (SFC) and input cell numbers were plotted.

Statistical Analysis:

In vitro data are presented as mean±1 SD. Student's t test was used to determine the statistical significance of differences between samples, and P<0.05 was accepted as indicating a significant difference.

Under these culture conditions, the population of antigen-specific T-cells undergoes at least 7 cell doublings after the initial stimulation over the first 7 days, as shown in FIG. 1A. Thus we expect a weekly T-cell expansion of 128-fold (as measured by the frequency of antigen-specific T-cells times the total number of cells in the cell composition). The frequency of tetramer positive cells after the first, second, and third stimulations is shown in FIG. 1B. On day 0 the frequency of T-cells reactive against two EBV tetramers, RAK and QAK was 0.02% and 0.01%, respectively. After a single stimulation on day 0, by day 9 the frequency of tetramer-positive T-cells in the cell composition had increased from 0.02% and 0.01% to 2.7% and 1.25%, respectively. Thus, a 135-fold and 125-fold increase in the percentage of antigen-specific tetramer positive T-cells residing within the cell composition was attained as measured by RAK and QAK. Also, after a single stimulation on stage 1 of culture, day 0, a 1.1 fold increase in the surface density of cells in the cell composition (data not shown) was observed by day 9 (approximately $1.1\times10^6$ cells/cm² were present). Since the majority of cells within the PBMC composition are not specific for the stimulating antigens, little overall increase in total cell number is observed, but the fold expansion of the antigen-specific cell population within the composition was around 280 during the first stage of culture, as shown in FIG. 1C. Unfortunately, although the number of cell doublings was the same during the second and third stages of culture as measured by CSFE, this rate of antigen-specific T cell expansion was not sustained during the $2^{nd}$ or the $3^{rd}$ stages of culture, being only 5.7 in stage two and 4.3 in stage three. FIG. 2 shows a table that illustrates the discrepancy between the potential expansion and observed fold expansion of antigen-specific T-cells (n=3).

Example 1 demonstrates that the amount of time it takes to produce the desired cells is typically delayed after roughly the first week of production since the rate of population expansion of the desired cells decreases in subsequent stages of culture.

Example 2: Reducing the Amount of Time Needed to Increase the Desired Cell Population can be Achieved by Reducing the Cell Surface Density of the Desired Cell Population as the Onset of any Given Stage or Stages of Culture We hypothesized that the decreased rate of expansion of the desired cell population following the second T-cell stimulation compared to the first stimulation was due to limiting cell culture conditions that resulted in activation induced cell death (AICD). For example, referring to FIG. 3A, at the first stimulation, the EBV antigen-specific T-cell component of PBMCs represents, at most, 2% of the population and so the antigen-specific responder T-cell seeding density is less than $2\times10^4$ per cm², with the remaining PBMC acting as non-proliferating feeder cells (seen as the CFSE positive cells in FIG. 3A) that sustain optimal cellto-cell contact allowing proliferation of the antigen-specific CTLs. By contrast, at the second stimulation on day 9, the majority of T-cells are antigen-specific, and although the total cell density of the composition is about the same, the proliferating cell density is 50 to 100 fold higher. As a consequence, on re-stimulation the majority of cells proliferate and may therefore rapidly consume and exhaust their nutrients and $O_2$ supply.

To determine whether limiting culture conditions were responsible for sub-optimal T cell growth rates, we measured the expansion of activated T-cells plated at lower cell densities. Methods were as previously described in Example 1.

Figure 3B:
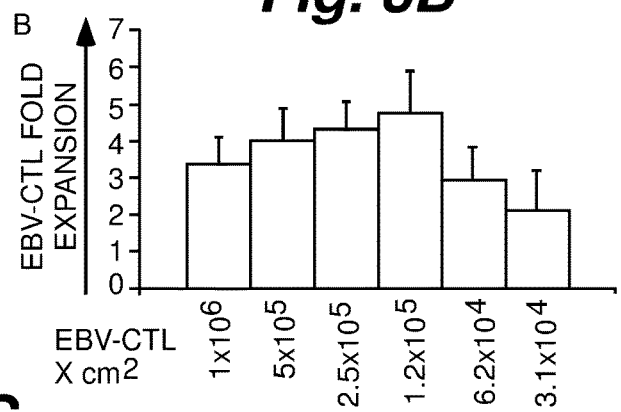
FIG. 3B shows the expansion of a population of antigen-specific T-cells as surface densities diminish from $1\times10^6$/cm$^2$ to $3.1\times10^4$/cm$^2$ while maintaining an antigen-specific T-cell to antigen presenting cell ratio of 4:1 in Example 2.
Figure 3C:
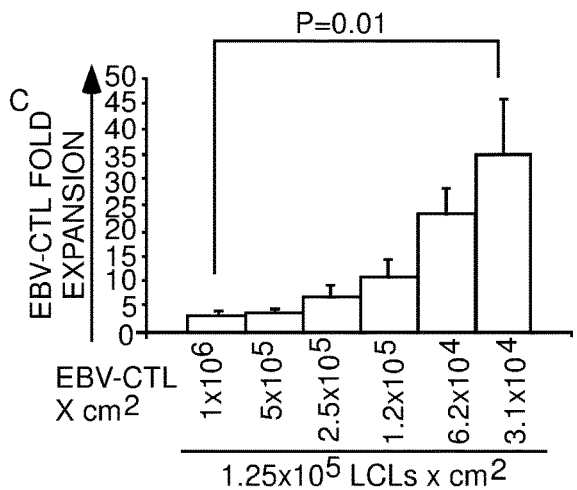
FIG. 3C shows the expansion of a population of antigen-specific T-cells as surface densities diminish from $1\times10^6$/cm$^2$ to $3.1\times10^4$/cm$^2$ while in the presence of a fixed number of antigen presenting cells in Example 2.

We seeded activated EBV-specific T-cells in wells of standard 24-well plates, each well having 2 $cm^2$ of growth surface area, at doubling dilutions to create diminishing surface densities ranging from $1 \times 10^6/cm^2$ to $3.1 \times 10^4/cm^2$ while maintaining a responder cell to stimulatory cell ratio (R:S) of 4:1 as shown in FIG. 3B. The maximum CTL expansion (4.7±1.1 fold) was achieved with a starting CTL surface density of $1.25 \times 10^5$ per $cm^2$, but further dilution decreased the rate of expansion as shown in FIG. 3B. We speculated that this limiting dilution effect was possibly due to lack of cell-to-cell contact, and therefore we cultured doubling dilutions of EBV-CTL from surface densities of $1 \times 10^6$ to $3.1 \times 10^4$ with a fixed number of feeder cells (EBV-LCL plated at a surface density of $1.25 \times 10^5/cm^2$) and assessed cell expansion over a 7 day period. We observed a dramatic increase in CTL expansion from merely 2.9±0.8 fold with EBV-CTL at a surface density of $1 \times 10^6/cm^2$ all the way to a 34.7±11 fold expansion with EBV-CTL at a surface density of $3.1 \times 10^4/cm^2$, as presented in FIG. 3C. Importantly, this modification of the culture conditions did not change the function or antigen specificity of the cells (data not shown). A population of activated antigen-specific T cells is therefore capable of greater expansion than conventional culture methods allow. Of note, the maximum surface density achieved after stimulation (1.7 to $2.5 \times 10^6/cm^2$) was the same regardless of the starting surface density.

Thus, conventional culture conditions were limiting, indicating the medium volume to growth surface area ratio needs to increase beyond the conventional 1 ml/$cm^2$ to allow the desired cell population to move beyond the surface density limits of conventional methods. Additionally, improved expansion of antigen-specific CTL to about 34-fold can be obtained by reducing the surface density of the desired cell population below conventional methods at the onset of any stage of culture. This has substantial ramifications in cell therapy, where the quantity of cells at the onset of production is often quite limited. For example, by distributing the in limited amount of desired cells onto increased surface area at lowered surface density, a greater population of desired cells can be attained in a shorter period of time as the rate of population growth increases dramatically relative to conventional surface density.

Figure 4:
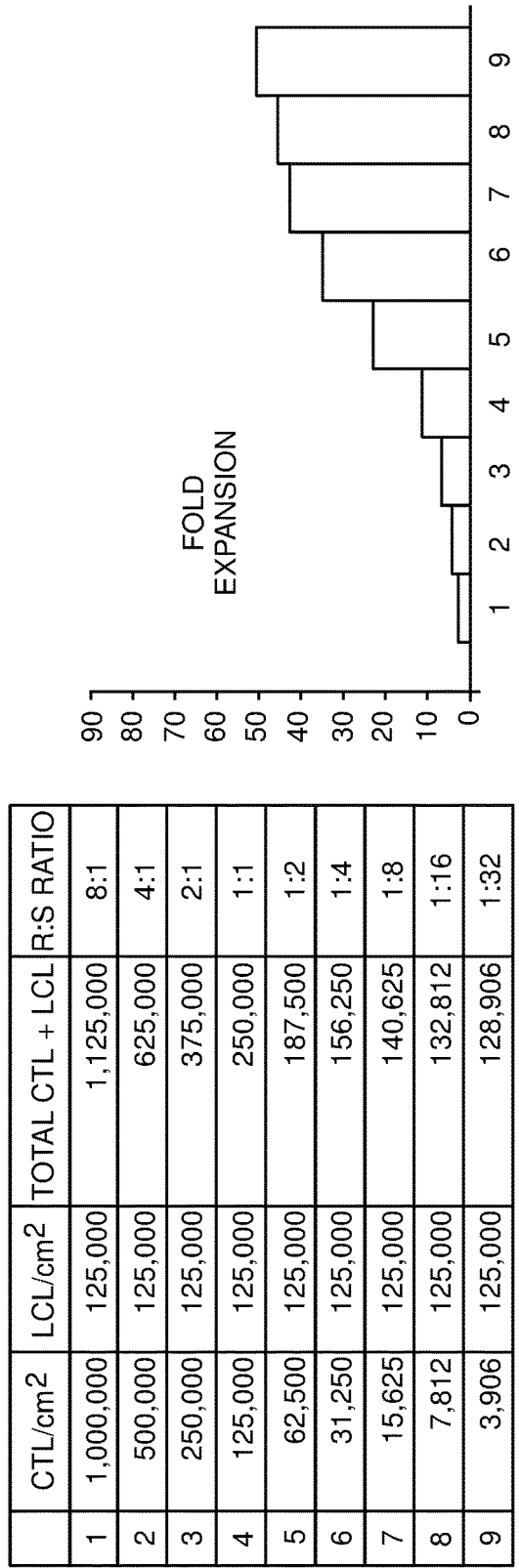
FIG. 4 shows an example of results obtained when continuing the work described in FIG. 3, which further demonstrated that when desired cells need the support of other cells, unconventionally low desired cell surface density can initiate population expansion so long as desired cells are in the presence of an adequate supply of feeder and/or antigen presenting cells.

Example 3: A Minimum Surface Density of a Cell Population that Includes the Desired Cells and/or Antigen Presenting Cells can Allow Outgrowth of a Desired Cell Population that is Seeded at Very Low Surface Density FIG. 4 shows an example of results we obtained when continuing the work described in FIG. 3, which further demonstrated that when desired cells need the support of other cells, unconventionally low desired cell surface density can initiate population expansion so long as desired cells are in the presence of an adequate supply of feeder and/or antigen presenting cells. In these experiments, we continue to demonstrate how a total cell composition with a surface density and R:S ratio of between about $1.0 \times 10^6$ desired cells/$cm^2$ at an R:S ratio of 8 to 1 and merely about 3900 desired cells/$cm^2$ at an R:S ratio of 1 to 32 could allow desired cells to be greatly expanded to over 50 fold times the starting surface density, at which point we discontinued testing.

Figure 5:
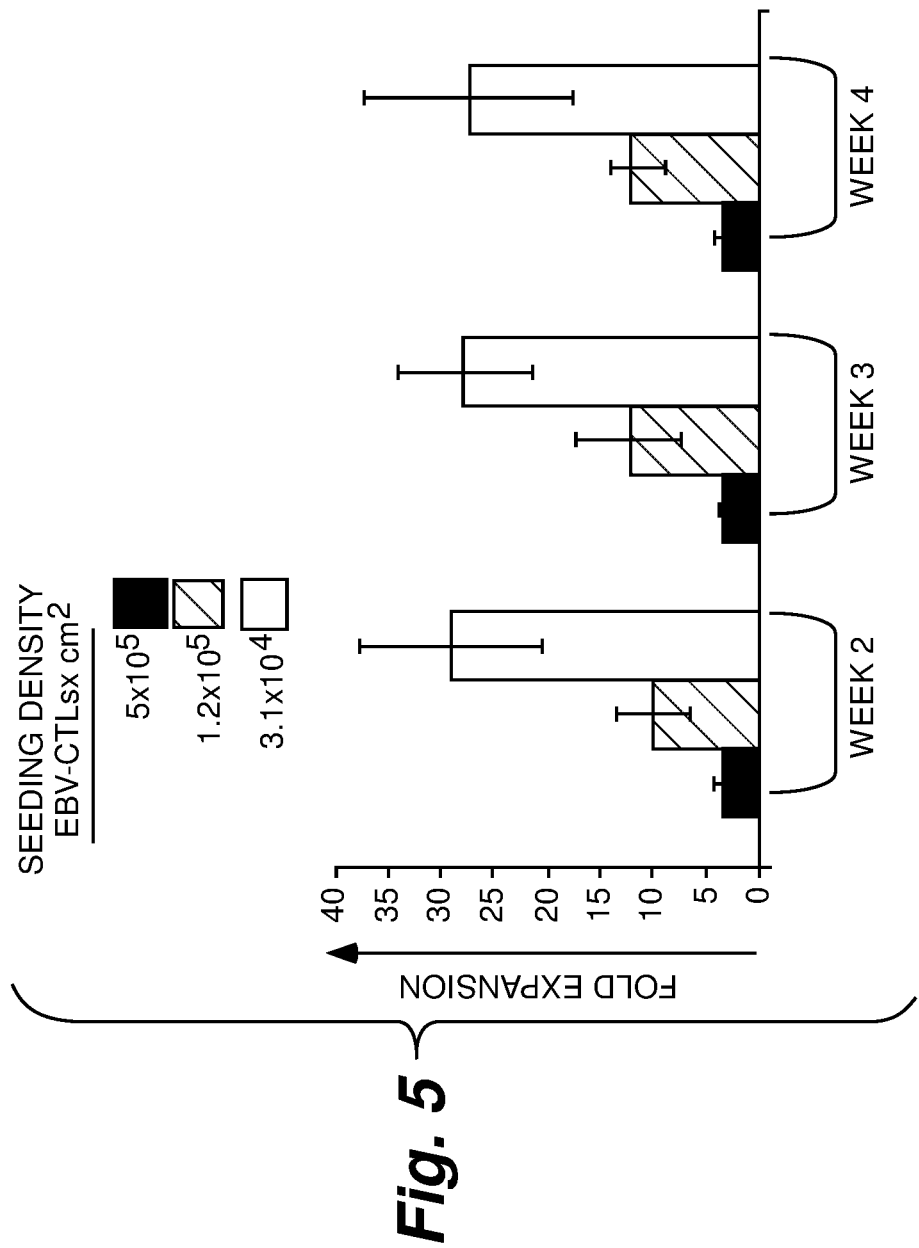
FIG. 5 shows a histogram demonstrating the ability to repeat the magnitude of the population expansion of desired cells by initiating culture at three differing cell surface densities (CTL/cm$^2$).

Example 4: The Ability to Allow a Production Process to Repeat in Stages by Initiating a Stage with an Unconventionally Low Desired Cell Surface Density, Allowing Population Expansion, Terminating the Stage and Repeating Conditions was Demonstrated to Deliver Repeatable Outcomes We continued the assessments described in Example 3 at three of the desired cell surface densities (CTL/$cm^2$) as shown in FIG. 5. Each specific seeding density was able to consistently attain the same fold expansion. The implications will be described in more detail further on as they relate to the ability to dramatically reduce the production time for a desired cell population.

Example 5: Culturing Desired Cells on a Growth Surface that is Comprised of Gas Permeable Material while Simultaneously Increasing the Medium Volume to Growth Surface Area Ratio Increases the Number of Times a Desired Cell Population can Double in a Given Stage of Culture Relative to Conventional Methods and Increases the Surface Density that is Attainable Cell lines and tumor cells, immunophenotyping, CFSE labeling, AnnexinV-7-AAD staining, chromium release assay, Enzyme-Linked Immunospot (ELIspot) assay, retrovirus production and transduction of T-lymphocytes, and statistical analysis were as described in Example 1.

Figure 6:
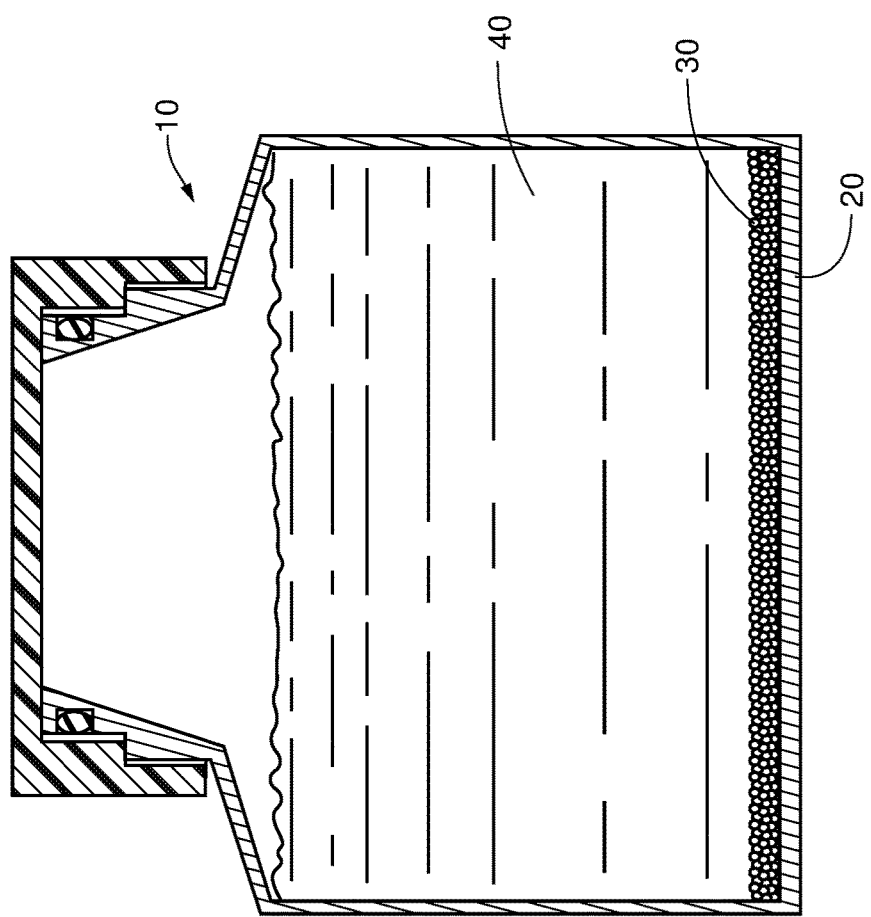
FIG. 6 shows a cross-sectional view of a gas permeable test fixture used to generate data.

Test fixtures (hereinafter generically referred to as "G-Rex") were constructed as shown in FIG. 6. Bottom 20 of each G-Rex 10 was comprised of gas permeable silicone membrane, approximately 0.005 to 0.007 inches thick. Pending U.S. Publication No. 2005/0106717 A1 to Wilson is among many other sources of information relating to the use of alternative gas permeable materials and can be used to educate skilled artisans about gas permeable culture device shapes, features, and other useful characteristics that are beneficial to many of the embodiments of this invention. In this Example 3, G-Rex (referred to as "G-Rex40") had a growth surface area of 10 $cm^2$, upon which a cell composition (shown as item 30) rested, the characteristics of the cell composition varied throughout the experiment as described within. Medium volume (shown as item 40) unless otherwise indicated was 30 mL, creating a medium volume to growth surface area ratio of 3 ml/$cm^2$.

Figure 7A:
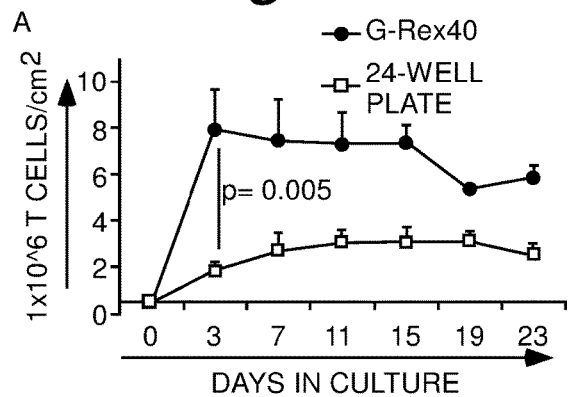
FIG. 7A shows the growth curves of antigen-specific T cells produced in accordance with the present invention in comparison to conventional methods as undertaken in Example 5.

Activated EBV-specific CTL and irradiated autologous EBV-LCLs at the conventional 4:1 ratio of CTL:LCL were cultured in G-Rex40 devices. EBV-CTLs were seeded at a surface density of $5 \times 10^5$ cells/$cm^2$ in the G-Rex40 and the rate of EBV-CTL population expansion was compared with EBV-CTL seeded at the same surface density in a standard 24-well plate with a medium volume to growth surface area of 1 ml/$cm^2$. After 3 days, as shown in FIG. 7A ($p=0.005$), the EBV-CTLs in the G-Rex40 had increased from $5 \times 10^5/cm^2$ to a median of $7.9 \times 10^6/cm^2$ (range 5.7 to $8.1 \times 10^6/cm^2$) without any medium exchange. In contrast, EBV-CTLs cultured for 3 days in conventional 24-well plates only increased from a surface density of $5\times10^5/cm^2$ to a median of $1.8\times10^6/cm^2$ (range 1.7 to $2.5\times10^6/cm^2$) by day 3. In the G-Rex40, surface density could be further increased by replenishing medium whereas cell surface density could not be increased by replenishing medium or IL2 in the 24-well plate. For example, EBV-CTL surface density further increased in the G-Rex40 to $9.5\times10^6$ cells/cm$^2$ (range $8.5\times 10^6$ to $11.0\times10^6/cm^2$) after replenishing the medium and IL-2 on day 7 (data not shown).

Figure 7B:
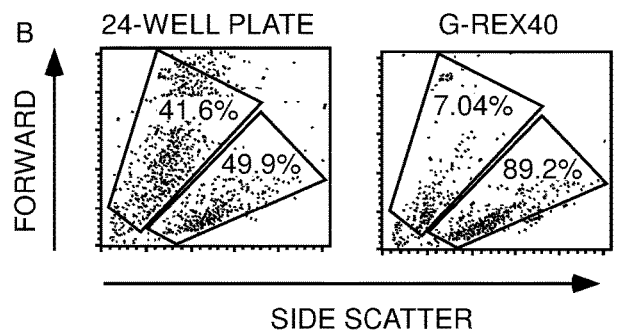
FIG. 7B shows that for Example 5, cell viability was significantly higher in antigen-specific T cells produced in accordance with the present invention in comparison to conventional methods as determined by flow cytometric forward vs. side scatter analysis.
Figure 7C:
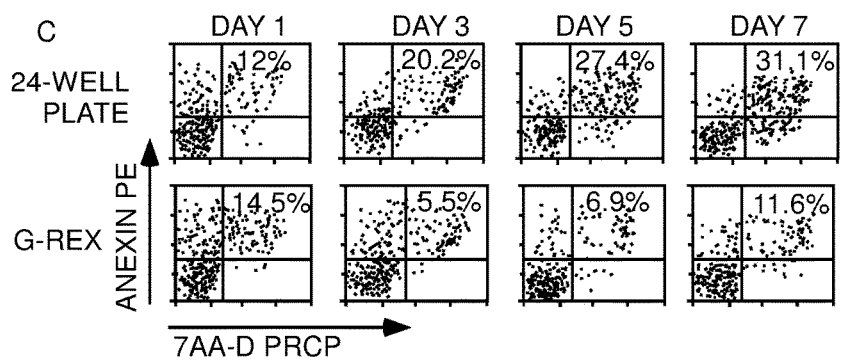
FIG. 7C shows that for Example 5, cell viability was significantly higher in antigen-specific t cells produced in accordance with the present invention in comparison to conventional methods as determined by Annexin-PI 7AAD.

To understand the mechanism behind the superior cell expansion in the G-Rex device, we assessed the viability of OKT3-stimulated peripheral blood T cells using flow cytometric forward vs. side scatter analysis on day 5 of culture. EBV-CTLs could not be assessed in this assay due to the presence of residual irradiated EBV-LCL in the cultures, which would interfere with the analysis. As shown in FIG. 7B, cell viability was significantly higher in the G-Rex40 cultures was significantly higher (89.2% viability in the G-Rex40 vs. 49.9% in the 24-well plate). We then analyzed the cultures each day for 7 days using Annexin-PI 7AAD to distinguish between live and apoptotic/necrotic cells, and observed consistently lower viability in T-cells expanded in 24 well plates compared to those in the G-Rex, as shown in FIG. 7C. These data indicate the cumulative improved survival of proliferating cells contributed to the increased cell numbers in the G-Rex devices compared to the 24-well plates.

Figure 7D:
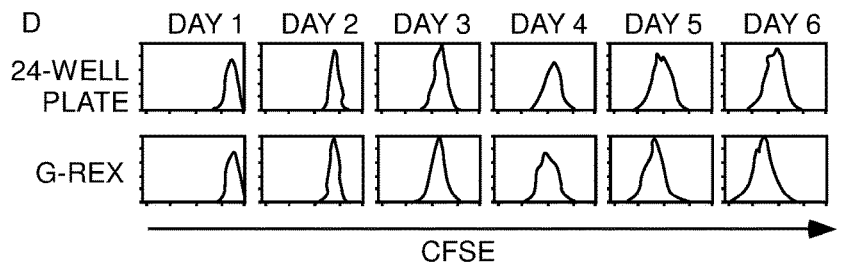
FIG. 7D showed that for Example 5, the superior growth of cells produced in the novel methods of the present invention exhibited the same cell specific growth rate as cell cultured using conventional methods as determined by daily flow cytometric analysis of CFSE labeled cells, confirming that the increased rate of cell expansion resulted from decreased cell death.

To determine if there was also a contribution from an increased number of cell divisions in the G-Rex versus the 24-well plates, T-cells were labeled with CFSE on day 0 and divided between a G-Rex40 device with a 40 ml medium volume and a 24 well plate with each well at a 2 ml medium volume. Daily flow cytometric analysis demonstrated no differences in the number of cell divisions from day 1 to day 3. From day 3 onwards, however, the population of desired cells cultured in the G-Rex40 continued to increase at a rate that exceeded the diminishing rate of the 2 ml wells, indicating that the culture conditions had become limiting as shown in FIG. 7D. Thus, the large population of desired cells in the G-Rex40 test fixtures resulted from a combination of decreased cell death and sustained proliferation relative to conventional methods.

Figure 8A:
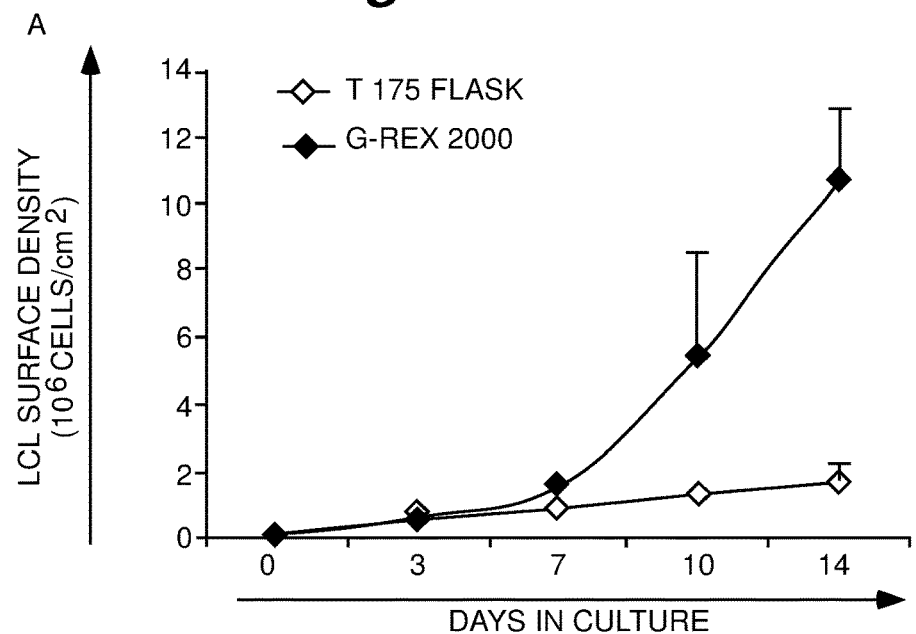
FIG. 8A shows how EVB-CTLs were able to expand beyond what was possible in conventional methods without need to exchange medium.
Figure 8B:
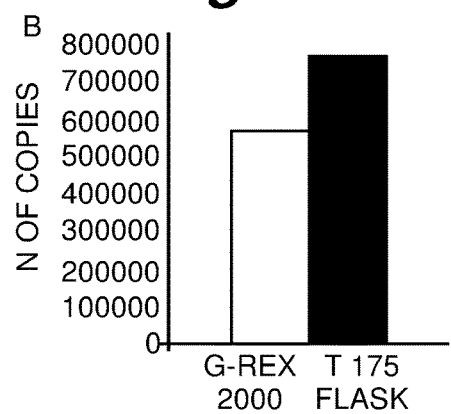
FIG. 8B shows how the culture condition of Example 6 did not modify the final cell product as evaluated by Q-PCR for EBER.
Figure 8C:
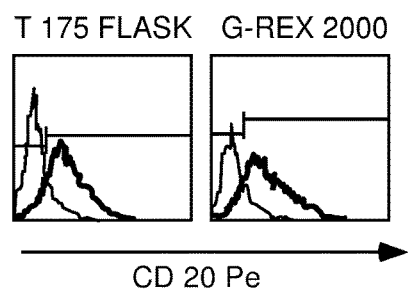
FIG. 8C shows how the culture condition of Example 6 did not modify the final cell product as evaluated by Q-PCR for B cell marker CD20.

Example 6: By Use of Unconventionally High Ratios of Medium Volume to Growth Surface Area and Use of Growth Surfaces Comprised of Gas Permeable Material, the Need to Feed Culture During Production can be Reduced while Simultaneously Obtaining Unconventionally High Desired Cell Surface Density This was demonstrated through use of G-Rex test fixtures for the initiation and expansion of EBV:LCLs. For purposes of this example, G-Rex2000 refers to device as described in FIG. 8, the exception being the bottom is comprised of a 100 cm$^2$ growth surface area and a 2000 ml medium volume capacity is available. EBV-LCLs were cultured in and expand in the G-Rex2000 without changing the cell phenotype. EBV-LCL were plated into a G-Rex2000 at a surface density of $1\times10^5$ cells/cm$^2$ along with 1000 ml of complete RPMI medium to create a medium volume to surface area ratio of 10 ml/cm$^2$. For comparison, EBV-LCL were plated into a T175 flask at a surface density of $5\times10^5$ cells/cm$^2$ along with 30 ml of complete RPMI medium to create a medium volume to surface area ratio of about 0.18 ml/cm$^2$. As presented in FIG. 8A, the EBV-LCL cultured in G-Rex2000 expanded more than those in the T175 flask without requiring any manipulation or media change. This culture condition did not modify the final cell product as evaluated by Q-PCR for EBER and B cell marker CD20 as presented in FIG. 8B and FIG. 8C.

Example 7: When Sufficient Feeder and/or Antigen Cells are not Present at the Onset of Culture, Desired Cells May not Expand. However, the Cell Composition can be Altered to Include an Additional Cell Type Acting as Feeder Cells and/or Antigen Presenting Cell to Allow Expansion FIG. 9 shows an illustrative example in which we experimentally demonstrated that a very low cumulative surface density of desired cells and antigen presenting cells (in this case AL-CTLs and LCLs cells combining to create a cell composition with a surface density of 30,000 cells/cm$^2$) was unable to initiate outgrowth of the AL-CTL population. However, this same cell composition could be made to grow by altering the composition to include another cell type acting as a feeder cell. In this case we evaluated a feeder layer of three various forms of irradiated K562 cells at a surface density of about $0.5\times10^6$ cells/cm$^2$ and in all cases the population of AL-CTL expanded from the initial cell composition depicted in the first column of the histogram to move from a surface density of just 15,000 cells/cm$^2$ to a surface density of $4.0\times10^6$ cells/cm$^2$ over 14 days. We also demonstrated, as opposed to the addition of a third cell type, increasing the population of LCLs achieved similar favorable results. The high surface density used for the LCL or K562 was arbitrarily chosen to demonstrate that a very low population of desired cells can be used to initiate growth when the cell composition includes an adequate number of feeder and/or antigen specific cells. When feeder cells are in short supply, expensive, or cumbersome to prepare, reducing their surface density to below $0.5\times10^6$ cells/cm$^2$ is recommended. In general, and as we have demonstrated, when antigen presenting cells and/or feeder cells are in the cell composition, the additive surface density of the antigen presenting cells and/or feeder cells and the desired cells should preferably be at least about $0.125\times10^6$ cells/cm$^2$ to create enough surface density in the cell composition to initiate the expansion of the desired cell population. Also, to attain the continued expansion beyond standard surface density limits, the use of growth surfaces comprised of gas permeable material was used in this example along with a medium volume to surface area ratio of 4 ml/cm$^2$.

Example 8: Reduced Desired Cell Surface Densities, Altered Responder Cell to Stimulatory Cell Ratios, Increased Medium to Growth Surface Area Ratios, and Periodic Distribution of Cells at a Low Surface Density Culture onto Growth Surfaces Comprised of Gas Permeable Material Allow More Desired Cells to be Produced in a Shorter Period of Time and Simplifies the Production Process when Compared to Other Methods To further evaluate our ability to simplify and shorten the production of desired cells, we used G-Rex test fixtures for the initiation and expansion of EBV-CTLs. For purposes of this example, G-Rex500 refers to device as described in FIG. 6, the exception being the bottom is comprised of a 100 cm$^2$ growth surface area and a 500 ml medium volume capacity is available.

For the initial stage of EBV-CTL production, we seeded PBMCs in the G-Rex40 at a surface density of $1\times10^6/cm^2$ (total=$10^7$ PBMCs distributed over 10 $cm^2$ growth surface area of the G-Rex40) and stimulated them with EBV-LCL using a 40:1 ratio of PBMC:EBV-LCL. For CTL production, this 40:1 ratio is preferable in the first stimulation to maintain the antigen-specificity of the responder T-cells. After the initial stage of culture, a second stage was initiated on day 9, wherein $1\times10^7$ responder T-cells were transferred from the G-Rex40 to a G-Rex500 test fixture. To initiate stage two of culture, 200 ml of CTL medium was placed in the G-Rex500, creating a medium volume to surface area ratio at the onset of stage two of 2 $ml/cm^2$ medium height at 2.0 cm above the growth surface area. The surface density of desired cells at the onset of stage two was $1\times10^5$ CTL/$cm^2$ with antigen presenting cells at a surface density of $5\times10^5$ LCL/$cm^2$, thereby creating a non-conventional 1:5 ratio of desired cells to antigen presenting cells. This stage two cell surface density and R:S ratio produced consistent EBV-CTL expansion in all donors screened. Four days later (day 13), IL-2 (50 U/ml—final concentration) was added directly to the culture, as was 200 ml of fresh medium, bringing medium volume to surface area ratio to 4 $ml/cm^2$. On day 16, the cells were harvested and counted. The median surface density of CTLs obtained was $6.5\times10^6$ per $cm^2$ (range $2.4\times10^6$ to $3.5\times10^7$).

Compared to conventional protocols, the use of growth surfaces comprised of gas permeable material allows increased medium volume to surface area ratios (i.e. greater than 1 $ml/cm^2$), lower cell surface densities (i.e. less than $0.5\times10^6/cm^2$), and altered ratios of responder to stimulator cells (less than 4:1) to create a decrease in production time. FIG. 10A shows the comparison of this G-Rex approach of Example 8 to the use of conventional methods of Example 1 and the G-Rex approach described in Example 5. As shown, the conventional method needed 23 days to deliver as many desired cells as could be delivered in either G-Rex method in about 10 days. After 23 days, the G-Rex approach of Example 8 was able to produce 23.7 more desired cells than the G-Rex method of Example 5 and 68.4 times more desired cells than the conventional method of Example 1. Furthermore, the desired cells continued to divide until day 27-30 without requiring additional antigen presenting cell stimulation provided the cultures were split when cell surface density was greater than $7\times10^6/cm^2$.

Although the CTLs could not be viewed clearly in the G-Rex using light microscopy, clusters of CTLs could be visualized by eye or by inverted microscope and the appearance of the cells on days 9, 16, and 23 of culture is shown in FIG. 10B. Culture in the G-Rex did not change the phenotype of the expanded cells as shown in FIG. 10C, with greater than 90% of the cell composition being CD3+ cells (96.7±1.7 vs. 92.8±5.6; G-Rex vs. 24-well), which were predominantly CD8+ (62.2%±38.3 vs. 75%±21.7). Evaluation of the activation markers CD25 and CD27, and the memory markers CD45RO, CD45RA, and CD62L, demonstrated no substantive differences between EBV-CTLs expanded under each culture condition. The antigen specificity was also unaffected by the culture conditions, as measured by ELIspot and pentamer analysis. FIG. 10D shows a representative culture in which T-cells stimulated with EBV peptide epitopes from LMP1, LMP2, BZLF1 and EBNA1 and stained with HLA-A2-LMP2 peptide pentamers staining showed similar frequencies of peptide-specific T-cells. Further, the expanded cells maintained their cytolytic activity and specificity and killed autologous EBV-LCL (62%±12 vs. 57%±8 at a 20:1 E:T ratio; G-Rex vs. 24-well plate), with low killing of the HLA mismatched EBV-LCL (15%±5 vs. 12%±7 20:1 ratio) as evaluated by $^{51}Cr$ release assays as shown in FIG. 10E.

Discussion of Various Novel Methods for Improved Cell Production for Cell Therapy:

Examples 1-8 have been presented to demonstrate to skilled artisans how the use of various conditions including reduced surface density of the desired cell population at the onset of a production cycle, reduced surface density ratios between responder cells and stimulating cells, growth surfaces comprised of gas permeable materials, and/or increased medium volume to growth surface area ratios can be used to expedite and simplify the production of cells for research and clinical application of cell therapy. Although Examples 1-8 were related to the production of antigen specific T cells, these novel culture conditions can be applied to many important suspension cell types with clinical relevance (or required for pre-clinical proof of concept murine models) including regulatory T cells (Treg), natural killer cells (NK), tumor infiltrating lymphocytes (TIL), primary T lymphocytes, a wide variety of antigen specific cells, and many others (all of which can also be genetically modified to improve their function, in-vivo persistence or safety). Cells can be expanded with feeder cells and/or antigen presenting cells that can include PBMC, PHA blast, OKT3 T, B blast, LCLs and K562, (natural or genetically modified to express and antigen and/or epitope as well as co-stimulatory molecules such as 41BBL, OX40L, CD80, CD86, HLA, and many others) which may or may not be pulsed with peptide and/or a relevant antigen.

Unconventionally Low Initial Surface Density:

One aspect of the present invention is the discovery that production time can be reduced relative to conventional methods by the use of lower desired cell surface density. In this manner, desired cells are able to have a greater numerical difference between their minimum and maximum cell surface densities than conventional methods allow. Preferably, when the rate of desired cell population growth has begun to diminish, but the quantity of desired cells is not yet sufficient to terminate production, the desired cells are re-distributed upon additional growth surfaces comprised of gas permeable material at low starting surface density once again.

To explain how our novel cell production methods that rely upon lower surface density at the onset of any given culture stage can be applied, an example is now described. FIG. 11 shows a graphical representation of expansion of a desired cell population on a growth surface under the conventional scenario as compared to population expansion of the desired cell type using one aspect of the present invention. In this novel method, the surface density of desired cells at the onset of a production stage is less than conventional surface density. In order to make the advantages of this novel method the focus, this explanation does not describe the process of initially obtaining the desired cell population. The "Day" of culture starts at "0" to allow skilled artisans to more easily determine the relative time advantages of this novel method. In this example, each production cycle of the conventional method begins at a conventional surface density of $0.5\times10^6$ desired cells/$cm^2$ while each production cycle of this example begins at a much lower and unconventional surface density of $0.125\times10^6$ desired cells/$cm^2$. Thus, 4 times more surface area (i.e. 500,000/125,000) is required in this example to initiate the culture of than the conventional methods require. In this example, the desired cells of the conventional method reaches a maximum surface density of $2\times10^6$ cells/$cm^2$ in 14 days. Thus, 1 cm² of growth area delivers 2×10⁶ cells/cm² which are then re-distributed onto 4 cm² of growth area so that production can be continued using the conventional starting density of 0.5×10⁶ cells/cm² (i.e. 4 cm² times 0.5× 10⁶ cells=2×10⁶ cells). The cycle repeats for another 14 days at which point maximum cell surface density is again reached, with each of the 4 cm² of growth surface area delivering 2.0×10⁶ cells for a total of 8.0×10⁶ cells that are then distributed onto 16 cm² of growth area and the growth cycle repeats to deliver a total of 32×10⁶ cells over 42 days.

The novel method depicted in FIG. 11, instead of using the conventional method of depositing 500,000 desired cells onto 1 cm² at the onset of production, distributes the 500,000 cells equally onto 4 cm² of growth area to create at unconventionally low starting surface density of 125,000 desired cells/cm² on Day 0. In example the novel method, as with the conventional method, has its growth rate about to diminish on Day 7. Cells in the novel method are at a surface density of 1×10⁶ cells/cm². Thus, at the time point where growth rate is about to diminish, this stage of culture has produced 4×10⁶ cells that are then re-distributed onto 32 cm² of growth area so that production in Stage 2 can be continued using the starting surface density of 0.125×10⁶ cells/cm² (i.e. 32 cm² times 0.125×10⁶ cells=4×10⁶ cells). The cycle, or stage, of production repeats for another 7 days to Day 14, at which point maximum cell surface density is again reached, with each of the 32 cm² of growth surface area containing 1.0×10⁶ desired cells to yield a total of 32×10⁶ cells in just 14 days. Note how at the end of each production cycle, as with the conventional method, the novel method delivers a multiple of the finishing surface density divided by the starting surface density. However, by lowering starting cell surface density and completing each stage of production before cells have entered a growth production time is dramatically lowered. This example that describes how, by lowering the desired cell surface density (in this case to 0.125×10⁶ cells/cm²) relative to conventional cell surface density, the same quantity of desired cells are delivered in just 33% of the time as the conventional method (14 days vs. 42 days).

Although we quantified the advantages using a starting surface density of 0.125×10⁶ cells/cm², skilled artisans should be aware that this example of the present invention demonstrates that any reduction below conventional cell surface density will reduce production duration. Furthermore, skilled artisans will recognize that in this and other novel methods presented herein, the rate of cell growth and point at which diminished cell growth occurs described is for illustrative purposes only and the actual rates will vary in each application based on a wide variety of conditions such as medium composition, cell type, and the like. Additionally, for a given application, skilled artisans will recognize that the advantage of this aspect of the present invention is the production time reduction resulting from the reduction of cell surface density below that of conventional cell surface density in any particular application, wherein the particular conventional surface density used in this illustrative example may vary from application to application.

Thus, one aspect of the methods of the present invention when there is a desire to minimize the duration of production for a given quantity of desired cells that reside within a cell composition by use of reduced cell surface density is now described. Desired cells should be deposited upon a growth surface at an unconventionally low cell surface density such that:

a. the desired cells are in the presence of antigen presenting cells and/or feeder cells and with medium volume to surface area ratio of up to 1 ml/cm² if the growth surface is not comprised of gas permeable and up to 2 ml/cm² if the growth surface is comprised of gas permeable, and b. the preferred surface density conditions at the onset of a production cycle being such that the target cell surface density is preferably less than 0.5×10⁶ cells/cm² and more preferably diminishing as described in FIG. 4, and c. the surface density of the desired cells plus the surface density of the antigen presenting cells and/or feeder cells is preferably at least about 1.25×10⁵ cells/cm².

Based on the examples above, it is advisable for one to verify that the expansion of the desired cell population does not become limited if there is an attempt to further reduce the surface density of the antigen presenting cells and/or feeder cells below 1.25×10⁵ cells/cm². We selected 1.25×10⁵ cells/cm² based on the goal of demonstrating that outgrowth of a population of desired cells at unconventionally low density can be achieved when augmented by an adequate supply of antigen presenting cells and/or feeder cells.

Use of Growth Surfaces Comprised of Gas Permeable Material and Higher Medium Volume to Growth Surface Area Ratios can Simplify and Shorten Production.

Another aspect of the present invention is the discovery that the use of growth surfaces comprised of gas permeable material and medium volume to growth surface area ratios that exceed conventional ratios, and repeated cycles of production that increase the amount of growth surface area used over time will reduce production duration.

Figure 12:
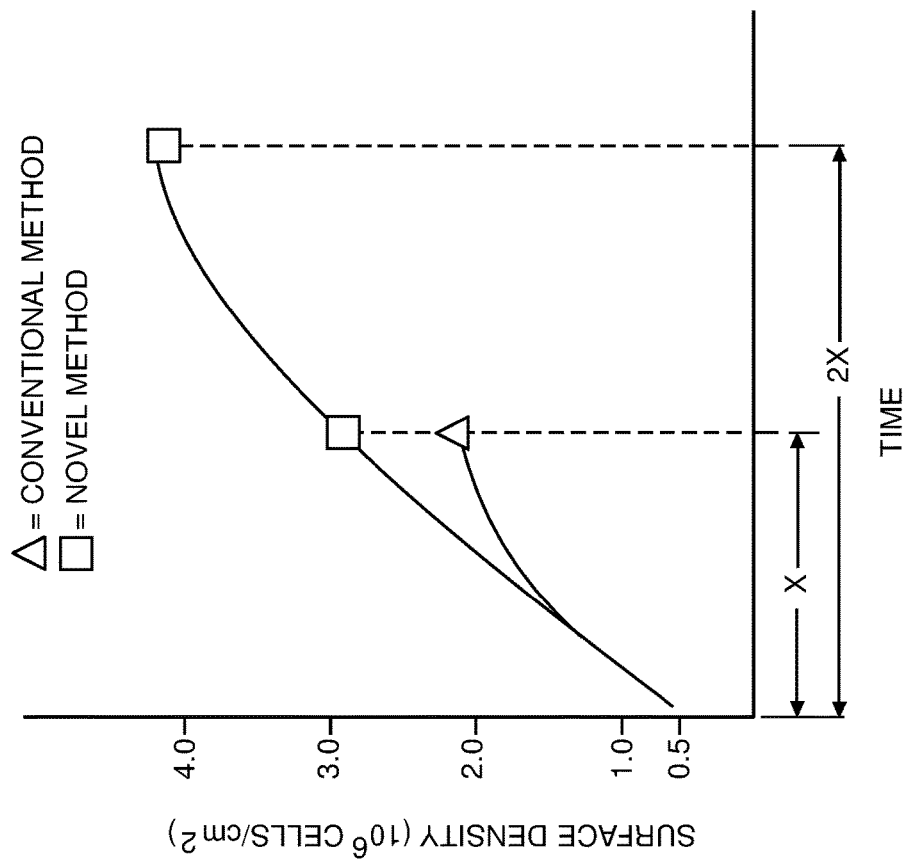
FIG. 12 shows an example of the advantages that can be obtained by utilizing a growth surface comprised of gas permeable material and an unconventionally high medium volume to growth surface area ratio beyond 1 or 2 ml/cm$^2$.

An illustrative example is now presented to show how these conditions can reduce the duration of production. FIG. 12 augments the discussion to show an example of the advantages that can be obtained by utilizing a growth surface comprised of gas permeable material and an unconventionally high medium volume to growth surface area ratio beyond 1 or 2 ml/cm². The discussion that follows is intended to demonstrate to skilled artisans how, by use of such a method, several options become available including reducing production time, reducing the amount of growth surface area used, and/or reducing labor and contamination risk. Skilled artisans will recognize that FIG. 12 and associated discussion is merely an example, and does not limit the scope of this invention.

The cell composition containing the desired cell population in this illustrative example is assumed to consume about 1 ml per "X" period of time. FIG. 12 shows two production processes, labeled "conventional method" and "novel method." At the onset of growth, each process begins with desired cells at a surface density of 0.5×10⁶/cm². However, the growth surface of in the novel method is comprised of gas permeable material and medium volume to surface area ratio is 2 ml/cm² as opposed to the conventional method of 1 ml/cm². In time period "X", the desired cell population of the conventional method has a reached a surface density plateau of 2×10⁶/cm² and is depleted of nutrients while the additional medium volume of the novel method has allowed growth to continue and desired cell surface density is 3×10⁶/cm². If the novel method continues, it reaches a surface density of 4×10⁶/cm². Thus, many beneficial options accrue. The novel method can be terminated prior to time "X" with more cells produced than the conventional method, can be terminated at time "X" with about 1.5 times more cells produced than the conventional method, or can continue until the medium is depleted of nutrients with 2 times many desired cells produced as the conventional method in twice the time but without any need to handle the device for feeding. In order for the conventional method to gather as many cells, the cells must be harvested and the process reinitiated, adding labor and possible contamination risk. Since cell therapy applications typically only are able to start with a fixed number of cells, the conventional method does not allow the option of simply increasing surface area at the onset of production.

Figure 13:
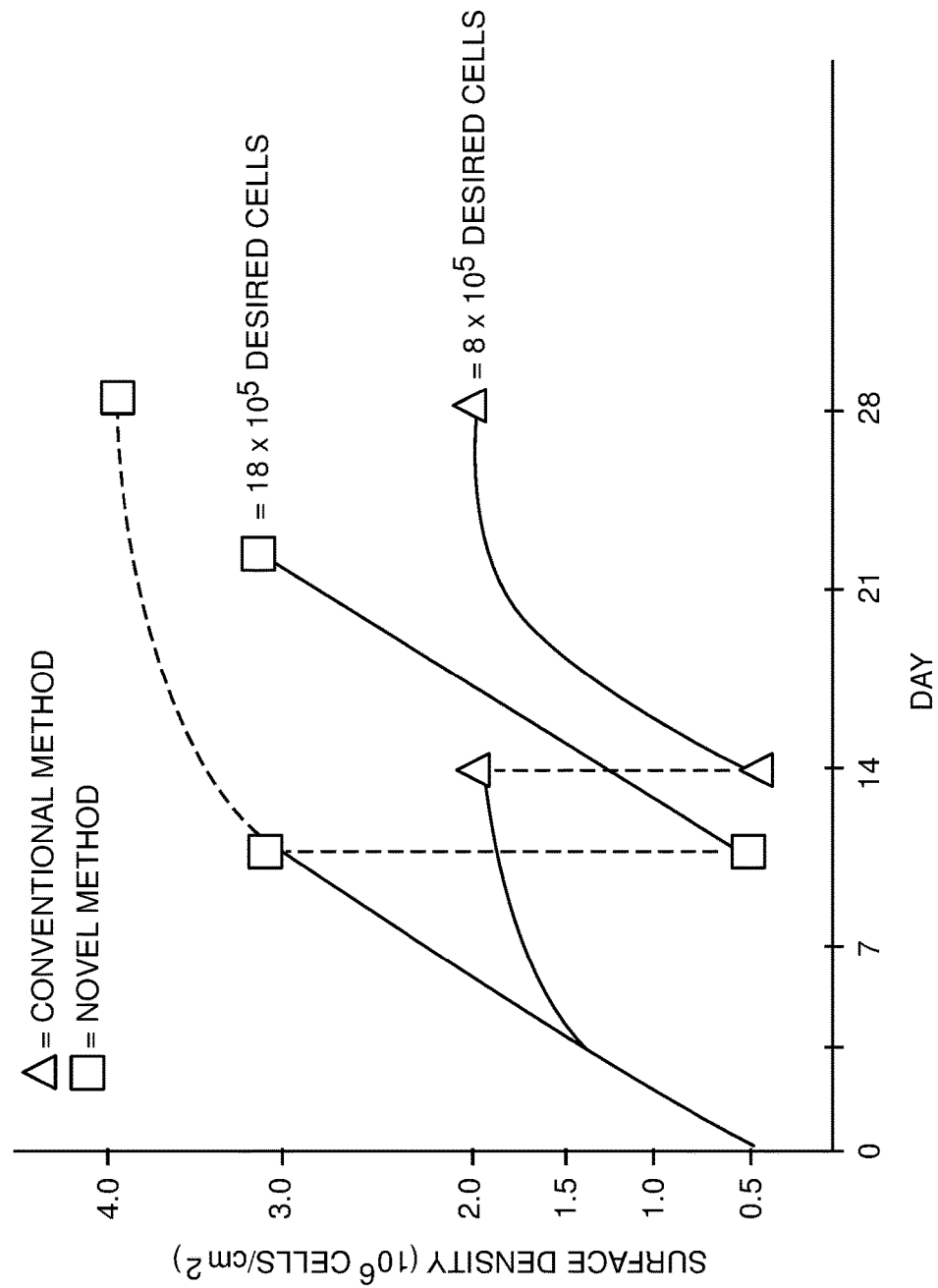
FIG. 13 shows a graphical representation of a novel method of expansion of a desired cell population on a growth surface under the conventional scenario as compared to population expansion of the desired cell type under one embodiment of the present invention in which the cell surface density at the completion of is much greater than conventional surface density.

FIG. 13 continues the example of FIG. 12 to show how more than one production cycle can be of further benefit. FIG. 13 shows a graphical representation of expansion of a desired cell population on a growth surface under the conventional method as compared to population expansion of the desired cell type under one novel method of the present invention in which the surface density of the novel method exceeds surface density of the conventional method. In order to make this embodiment the focus, this explanation does not describe the process of obtaining the desired cell population. The "Day" of culture starts at "0" to allow skilled artisans to more easily determine the relative time advantages of this aspect of the invention. In this example, both cultures are initiated using conventional desired cell surface density of $0.5 \times 10^5$ cells/cm$^2$ at "Day 0". In this illustrative example, the growth surface of the conventional method is also comprised of gas permeable material. However, the medium volume to growth surface ratio in the conventional method is 1 ml/cm$^2$ as opposed to 4 ml/cm$^2$ in the novel method. As shown in FIG. 13, the desired cell population in the conventional method begins to diminish in growth rate when it is at a surface density of about $1.5 \times 10^6$ cells/cm$^2$ in about 4 days and reaches a maximum surface density of $2 \times 10^6$ cells/cm$^2$ in 14 days. At that point the desired cell population is distributed to 4 cm$^2$ of growth area at a surface density of $0.5 \times 10^6$/cm$^2$ in fresh medium at 1.0 ml/cm$^2$ and the production cycle begins again, reaching a surface density of $2 \times 10^6$ cells/cm$^2$ in another 14 days and delivering $8 \times 10^6$ desired cells in 28 days. By comparison, the desired cell population in the novel method begins to diminish in growth rate when it is at a surface density of about $3 \times 10^6$ cells/cm$^2$ in roughly about 10 to 11 days and could reach a maximum surface density of $4 \times 10^6$ cells/cm$^2$ in 28 days. However, to accelerate production, the cycle ends when the desired cell population is still in a high rate of growth. Thus, at about 10 to 11 days the $3 \times 10^6$ cells are re-distributed to 6 cm$^2$ of growth surface area at a surface density of $0.5 \times 10^6$/cm$^2$ in fresh medium at 4.0 ml/cm$^2$ and the production cycle begins again, with the desired cell population reaching a surface density of $3 \times 10^6$ cells/cm$^2$ in roughly another 10 to 11 days and delivering $18 \times 10^6$ desired cells around 21 days. Thus, in about 75% of the time, the novel method has produced over 2 times the number of desired cells as compared to the conventional method.

We have been able to obtain cell surface density in excess of $10 \times 10^6$ cells/cm$^2$ upon growth surfaces comprised of gas permeable material, demonstrating that the use of the high surface density aspect of our invention is not limited to the density described in this example.

Thus, another example of the methods of the present invention when there is a desire to minimize the duration of production for a given quantity of desired cells that reside within a cell composition by use of reduced cell surface density is now described:

a. seeding the desired cells upon a growth surface area comprised of gas permeable material and in the presence of antigen presenting cells and/or feeder cells and with medium volume to surface area ratio of at least 2 ml/cm$^2$, and b. establishing the preferred surface density conditions at the onset of a production cycle such that the target cell surface density is within the conventional density of about $0.5 \times 10^6$ cells/cm$^2$, and c. allowing the desired cell population to expand beyond the conventional surface density of about $2 \times 10^6$ cells/cm$^2$, and d. if more of the desired cells are wanted, redistributing the desired cells to additional growth surface comprised of gas permeable material and repeating steps a-d until enough desired cells are obtained.

When using these novel methods, further benefits can be attained by combining the attributes of initiating culture using unconventionally low surface area, using novel surface density ratios of desired cells and/or feeder cells, utilizing a growth surface area comprised of gas permeable material, utilizing unconventionally high ratios of medium volume to growth surface area, and conducting production in cycles. The conditions can be varied at any cycle of production to achieve the desired outcomes, such as striking a balance between reduced production time, surface area utilization, feeding frequency, and the like.

Figure 14:
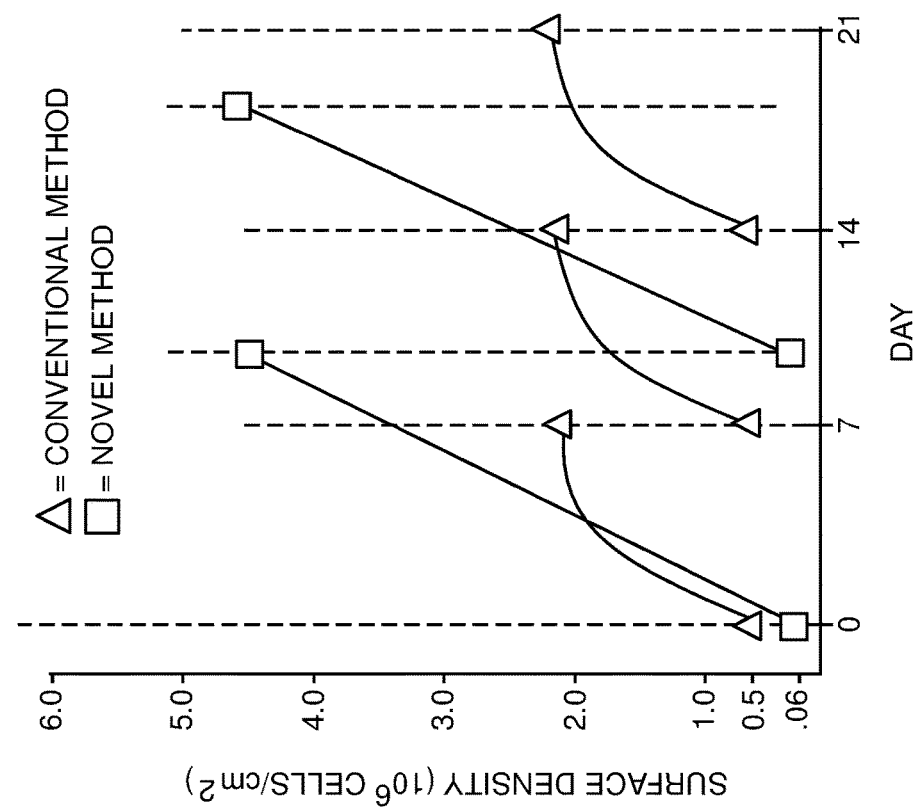
FIG. 14 shows another novel method of cell production that provides yet further advantages over conventional methods.

FIG. 14 shows another novel method in which still further advantages relative to conventional methods are obtained. As with other illustrative embodiments described herein, skilled artisans will recognize that the description herein does not limit the scope of this invention, but instead acts to describe how to attain advantages of improved production efficiency.

In this example, desired cells are doubling weekly in conventional conditions. The "Day" of culture starts at "0" to allow skilled artisans to more easily determine the relative time advantages of this embodiment. Also, issues previously described related to feeder and/or antigen presenting cell surface density ratios are not repeated to simplify this example. For illustrative purposes, assume a starting population of 500,000 desired cells with a doubling time of 7 days in conventional conditions is present on "day 0" production. The conventional method begins with a surface density of $0.5 \times 10^6$ cells/cm$^2$ and a medium volume to surface area ratio of 1 ml/cm$^2$. As shown, when the population of the desired cells reaches a surface density of $2 \times 10^6$ cells/cm$^2$ the cells are distributed onto additional surface area at a surface density of $0.5 \times 10^6$ cells/cm$^2$ and the production cycle begins anew. The novel method of this example begins with a surface density of $0.06 \times 10^6$ cells/cm$^2$, a growth surface area comprised of gas permeable material, and a medium volume to surface area ratio of 6 ml/cm$^2$. As shown, when the population is nearing the start of a growth plateau, cells are redistributed to more growth surface area. In this case, the population is determined to be reaching plateau from noting that plateau is initiated in the conventional method when cell surface density approaches 1.5 times the medium volume to surface area ratio (i.e. about $1.5 \times 10^6$ cells/ml). Thus, at a surface density of about $4.5 \times 10^6$ cells/cm$^2$ at about 9 days, cells are distributed onto 36 cm$^2$ of growth surface area and the production cycle begins anew.

FIG. 15 tabulates a comparison of each production method depicted in FIG. 14, and extends to stages to demonstrate the power of the novel method, and why it is wise to adjust the production protocol at various stages to fully capture the efficiency. Note that the novel method overpowers the conventional method after completing just the second stage of the production cycle, delivering nearly 1.37 times more cells in only about half the time with just 61% of the surface area requirement. However, note how the third stage of the production cycle creates a massive increase in cells and a corresponding increase in surface area. Thus, one should model the production cycles to anticipate how to adjust the initial cell surface density and/or final cell surface density throughout each cycle of the process to attain an optimal level of efficiency for any given process.

As an example, FIG. 16 shows an example of how one could alter variables in the novel method to gain efficiency as production progresses. For example, an increase in the starting surface density of cycle 3 from 0.06 to 0.70 cell/cm$^2$ and a change to the final surface density from 4.5 to 7.5 cells/cm$^2$ can be undertaken. Increasing the final surface density is a matter of increasing the medium volume to surface area ratio beyond the initial 6 ml/cm$^2$ to a greater number. The greater the medium volume to surface area, the longer the cycle remains in rapid growth phase (i.e. the population expansion prior to plateau). In this case we have allowed 5 extra days to complete the rapid growth phase and raised the medium volume to surface area ratio to about 8 ml/cm$^2$. So doing, in this example, allows over 3 trillion cells to be produced in 34 days with a reasonable surface area. For example, we have fabricated and tested devices with about 625 cm$^2$ of growth surface comprised of gas permeable material. This is clearly a superior approach to producing cells than the conventional method.

Thus, another preferred embodiment of the methods of the present invention when there is a desire to minimize the duration of production for a given quantity of desired cells that reside within a cell composition by use of reduced cell surface density is now described:
  a. seeding the desired cells upon a growth surface area comprised of gas permeable material and in the presence of antigen presenting cells and/or feeder cells and with medium volume to surface area ratio of at least 2 ml/cm$^2$, and
  b. establishing the preferred surface density conditions at the onset of a production cycle such that the target cell surface density is less than the conventional density, preferably at between about 0.5×10$^6$ desired cells/cm$^2$ and about 3900 desired cells/cm$^2$ and total number of desired cells and antigen presenting cells and/or feeder cells being at least about 1.25×10$^5$ cells/cm$^2$, and
  c. allowing the desired cell population to expand beyond the conventional surface density of about 2×10$^6$ cells/cm$^2$, and
  d. if more of the desired cells are wanted, redistributing the desired cells to additional growth surface comprised of gas permeable material and repeating steps a-d until enough desired cells are obtained.

The present invention provides devices and methods of cell culture that allow far superior cell production, particularly for the field of Adoptive Cell Therapy. It allows a wide variety of benefits relative to state of the art devices and methods including reducing the time needed to provide a given number of cells, greater fold expansion of a desired cell population from an initial quantity of cells, the ability to reduce and even eliminate the frequency of medium exchange, simplified methods of cytokine addition, the ability to reduce and even eliminate the need to count cells to determine their quantity, the ability to greatly reduce the amount of medium that cells need to be separated from post culture, the ability to create a more effective population of cells that are antigen specific, and the capacity to scale linearly.

Example 9: More Efficient Methods of Producing Cells within a Static Gas Permeable Culture Device by Establishing Novel Culture Conditions at the Start of the Culture Process Static cell culture experiments were conducted in which K562 cells were cultured in test devices configured with a growth surface comprised of gas permeable silicone material and with wall height that allowed 10 cm of medium to reside above the growth surface. The growth surface was held in a substantially horizontal position with a growth surface support as described more thoroughly in Wilson '717. Medium was placed in the test devices at a medium height of 10 cm beyond the growth surface, establishing a medium volume to growth area ratio of 10 ml/cm$^2$. K562 cells were also introduced into the test devices and the devices were placed into a cell culture incubator at 37 C, 5% CO2, and 95% R.H, whereby cells were allowed to gravitate to the growth surface. The medium was not perfused or subjected to forced agitation and gas was not forced to flow past the growth surface, instead making contact with the growth surface by random motion of the ambient atmosphere.

FIG. 17A, FIG. 17B, FIG. 17C, FIG. 17D, and FIG. 17E show, for illustrative purposes, a representative spreadsheet of the experimental conditions and typical results. Initial static culture conditions established surface densities ranging between 1.0E+06 to 6.25E+04 cells/cm$^2$, cell densities ranging from 1.0E+05 to 6.25E+03 cells/ml, with medium residing above the growth surface in all conditions at a constant height of 10 cm and all medium being the same formulation with glucose concentration at 240 mg/dl. The initial state of static culture was day 0 and cell counts and glucose concentration were assessed on day 4, day 8, day 11.

Figure 18:
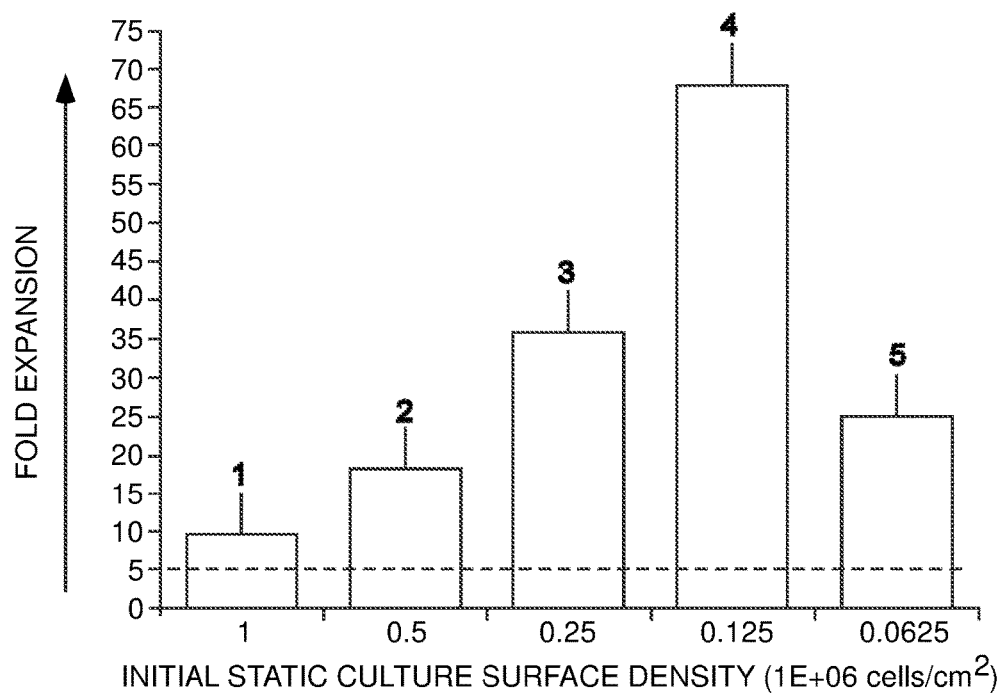
FIG. 18 compares the fold expansion of the population increase relative to the surface density of each of the experimental conditions detailed in FIG. 17A-FIG. 17E.

FIG. 18 compares the fold expansion of the population increase relative to the surface density of each of the experimental conditions detailed in FIG. 17A through FIG. 17E. Fold expansion of each condition was determined by dividing the cell surface density on day 11 by the cell surface density on day 0. In a series of evaluations where surface density is at a low limit of 5.0E+05 cells/cm$^2$ and medium height is at the upper limit of 2.0 cm, we concluded that the best fold expansion of K562 in gas permeable bags was about 4.8 fold. Thus, dotted line 6 shows typical fold expansion in state of the art K562 production methods using gas permeable bags. Each surface density condition established in our experiments created a population expansion that exceeded state of the art population expansion. Of note, the ability to increase the fold expansion of the population of cells greatly increased as conditions of initial static culture surface density decreased to 0.125E+06, and then further reductions were less advantageous although still far superior to state of the art methods.

Other observations were made that we explored further, particularly related to glucose being a potential surrogate measure of the number of cells present at any given time and the ability to perform extended culture without feeding.

Example 10: Novel Methods to Determine the Quantity Cells in a Population Residing within a Static Gas Permeable Culture Device without Need of Counting Cells We observed that glucose depletion rates were consistently indicative of the number of cells in culture despite the culture medium residing in a static state and (other than just routine handling of the device) not subjected to mechanically forced mixing such as by perfusion, shaking, or stirring prior to sampling. This finding opens the door to further simplification in the field of Adoptive Cell Therapy. For example, the act of counting cells to determine how well a culture is progressing is one of many factors that make cell production for Adoptive Cell Therapy impractical. The use of a surrogate measure in lieu of cell counts, combined with the inventive disclosures herein, brings even more simplification to cell production.

We have discovered that it is possible to use glucose concentration of the culture as a as a surrogate indicator of the population of the culture. For cultures in which cells reside upon a growth surface comprised of a given type of gas permeable material, knowing the minimum total medium volume needed for the culture to reach maximum surface density and the total reduction in glucose concentration needed for the culture to reach maximum surface density sets the stage for a surrogate prediction of the number of cells in the population of the culture. Equipped with that knowledge, one initiating culture (or a stage of culture) would determine the baseline glucose concentration of medium, the baseline volume of medium, and would keep track of the volume of medium added to the culture prior to taking a measure of glucose concentration at the time of population estimation. The estimated number of cells in the population is a function of the prorated total reduction in glucose concentration needed to reach maximum cell density multiplied by the prorated minimum medium volume needed to reach maximum surface density and multiplied by the maximum surface density possible on the growth surface.

We applied this method to cultures described throughout various disclosures of the present invention, in which the growth surface of experimental devices was comprised of dimethyl silicone, between about 0.006 to 0.0012 inches thick. A series of experiments were undertaken that determined minimum volume of medium needed to allow the cells to reach maximum surface density and the corresponding total reduction in glucose concentration. The total reduction in glucose concentration was about 250 mg/dl for a variety of cultures with various cell types including K562, LCL, and T cells. We were able to create formulaic relationships that were predictive of cell number in culture as show below, where:

A=baseline glucose concentration of medium
B=measure of glucose concentration at the time of population estimation
C=total reduction in glucose concentration needed to reach maximum surface density
D=baseline volume of medium
E=volume of medium added after baseline
F=minimum total medium volume needed to reach maximum surface density
G=maximum surface density
E=surface area of the growth surface $[(A-B)/C] \times [(D+E)/F] \times G \times E$=estimated number of cells in the culture population in the device. Note that the prorated minimum medium volume cannot exceed 100%, since additional medium will not increase surface density beyond the maximum capacity. For example, if a culture requires 10 ml to reach maximum surface density and the baseline volume of medium plus the volume of medium added exceeds 10 ml, one should use 100% as the prorated minimum medium volume.

Note that the predictive formulas require knowledge of the cell culture applications maximum cell density (and/or maximum surface density) under conditions in which cells reside on a growth surface comprised of the particular gas permeable material the artisan has selected. Experiments can be undertaken to make that determination. For example, to determine the maximum cell surface density of K562 cells upon a growth surface comprised of the gas permeable material in our experimental fixtures (dimethyl silicone as described previously), we increased medium height until surface density could increase no more. The minimum volume of medium needed to support a maximum attainable surface density of K562 at about 12.0E+06 cells/cm$^2$ was determined to be 10 ml with a corresponding total reduction in glucose concentration of 250 mg/ml.

Illustrative examples of how this information could be used to assess the number of cells in K562 culture follow. For the first example, assume medium is not added after the onset of culture and these conditions exist:
baseline medium volume=10 ml
baseline glucose concentration=475 mg/dl
glucose sample=300 mg/dl
surface area of the growth surface=100 cm$^2$
Then the calculation would proceed as follows:

$[(475 \text{ mg/dl} - 300 \text{ mg/dl})/250 \text{ mg/dl}] \times (10 \text{ ml} + 0 \text{ ml})/10 \text{ ml}] \times 12E+06 \text{ cells/cm}^2 \times 100 \text{ cm}^2 = 840 \times 10^6$ cells.

As another example, assume medium is added after the onset of culture and these conditions exist:
baseline medium volume=6 ml
baseline glucose concentration=475 mg/dl
glucose sample=300 mg/dl
surface area of the growth surface=100 cm$^2$
Then the calculation would proceed as follows:

$[((475 \text{ mg/dl} - 300 \text{ mg/dl})/250 \text{ mg/dl}) \times (6 \text{ ml} + 2 \text{ ml})/10 \text{ ml}] \times 12E+06 \text{ cells/cm}^2 \times 100 \text{ cm}^2 = 672 \times 10^6$ cells.

As yet another example, assume medium is added after the onset of culture and these conditions exist:
baseline medium volume=6 ml
baseline glucose concentration=475 mg/dl
glucose sample=300 mg/dl
surface area of the growth surface=100 cm$^2$
Then, since total medium volume added to the culture exceeds the minimum total medium volume needed to reach maximum surface density, prorated minimum medium volume goes to 100% and therefore the prorated value equals 1, and the calculation would proceed as follows:

$[1(475 \text{ mg/dl} - 300 \text{ mg/dl})/250 \text{ mg/dl}) \times (1)] \times 12E+06 \text{ cells/cm}^2 \times 100 \text{ cm}^2 = 840 \times 10^6$ cells.

Skilled artisans should be aware that by predetermining the maximum cell density in medium (cells/cm2) that the specific cell type(s) can attain when residing on the growth surface comprised of a particular type of gas permeable material, an alternative formulaic relationship can be used to estimate the number of cells in the culture. In that case, the formulaic relationship would be a function of; (the prorated total reduction in glucose concentration needed to reach maximum cell density)×(the volume in medium at the onset of culture plus the volume of medium added to the culture)× (maximum cell density). Be advised that in the event that the cumulative volume of medium exceeds that of the minimum volume of medium needed to reach maximum surface density, the minimum volume of medium should be used in place of the cumulative volume (as no extra medium volume will increase the surface density beyond its maximum).

To help understand the predictive capacity of the formulas, we included the predictions of the number of cells in culture on row 10 of each spreadsheet (normalized by growth surface area) of conditions shown in FIG. 17A through FIG. 17E. Comparison of row 10 with the counted cells of row 12 shows how the number of cells in culture at any given time can be determined with a reasonable degree of certainty by use of glucose as opposed to cell counts. In fact, cell counts may not be as accurate due to the inability to ensure the cells are mixed uniformly into the medium prior to counting. Thus, it may be more beneficial to rely on glucose measures. In a preferred embodiment, cell counts would not be taken at least for 4 days, more preferably for 5 days, more preferably for 6 days, more preferably for 7 days, more preferably for 8 days, and even more preferably not until the culture was terminated.

Figure 19B:
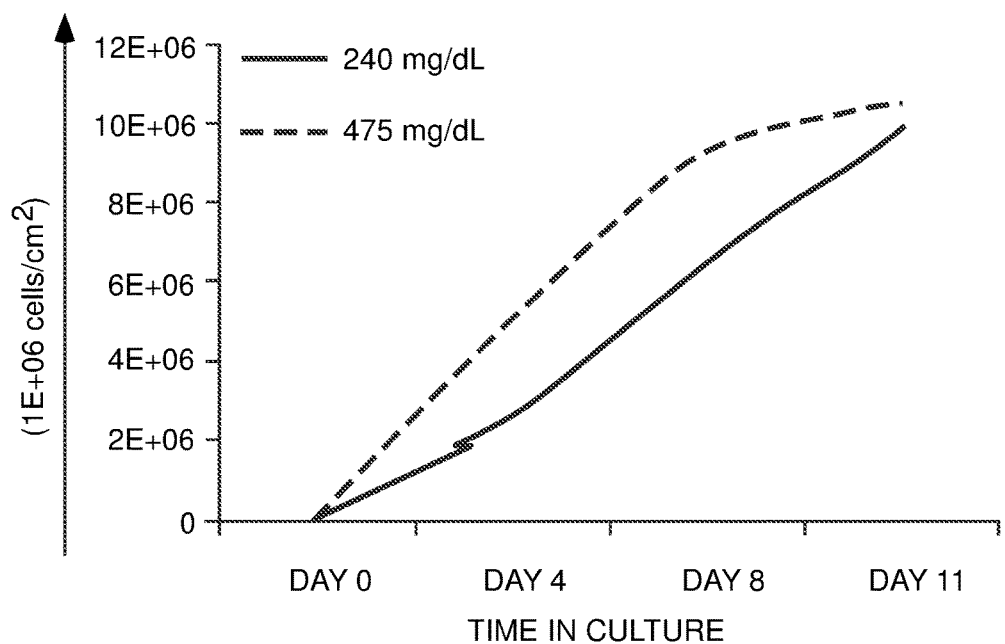
FIG. 19B shows cell population expansion under two starting glucose condition over a time period of 11 days.

More experiments were undertaken to determine if the formula dictating the relationship between glucose depletion and the number of live cells in the device was accurate when glucose concentration at the onset of cultures varied. Test fixtures were identical to those previously described. For illustrative purposes, FIG. 19A shows a representative spreadsheet of the experimental conditions and typical results for the culture of K562 cells under equivalent starting conditions except for the glucose concentration, which was 240 mg/dl vs. 475 mg/dl at the onset of culture. Results are graphically depicted in FIG. 19B, FIG. 19C, FIG. 19D, FIG. 19E, and FIG. 19F. Population growth by cell count and as predicted by glucose depletion was normalized for surface density.

Figure 19C:
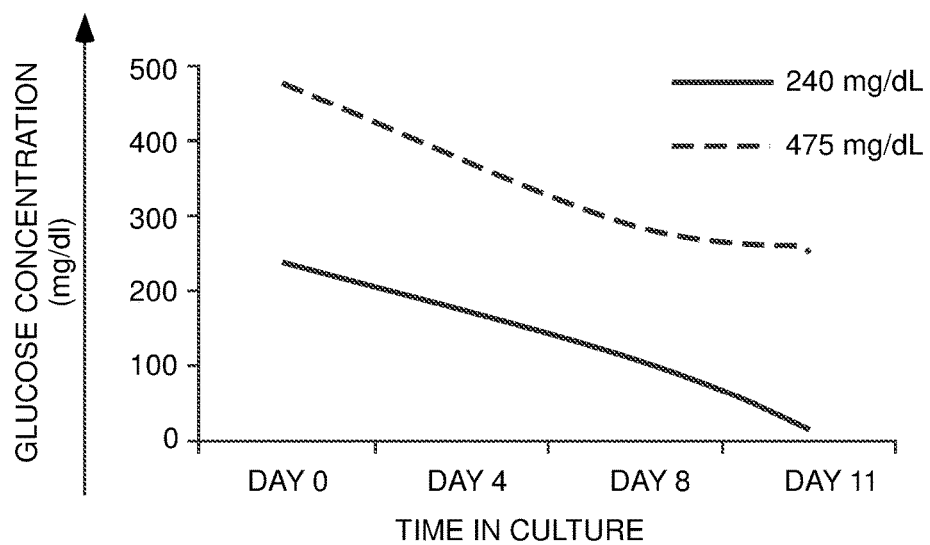
FIG. 19C shows the glucose depletion rate in each culture condition.
Figure 19D:
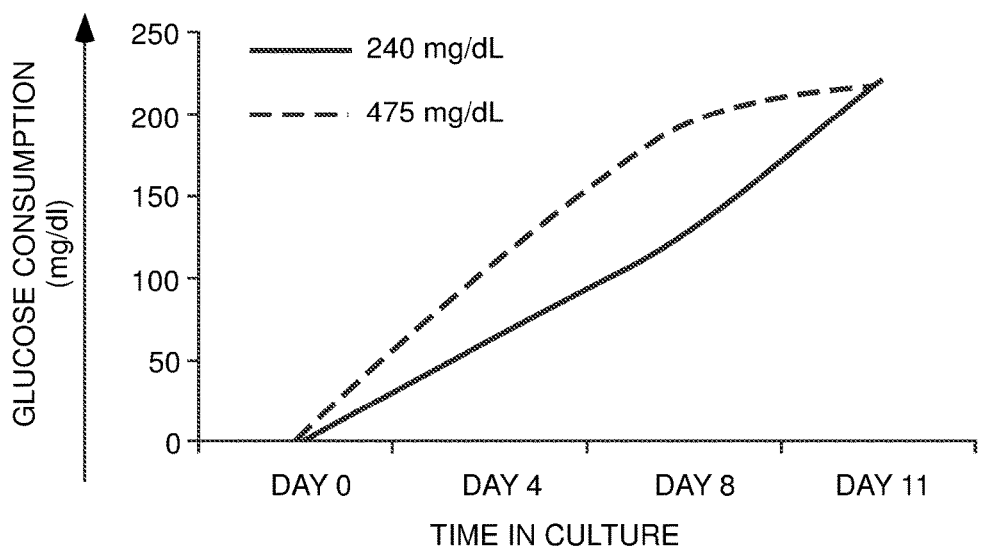
FIG. 19D shows the glucose consumption rate in each culture condition.
Figure 19E:
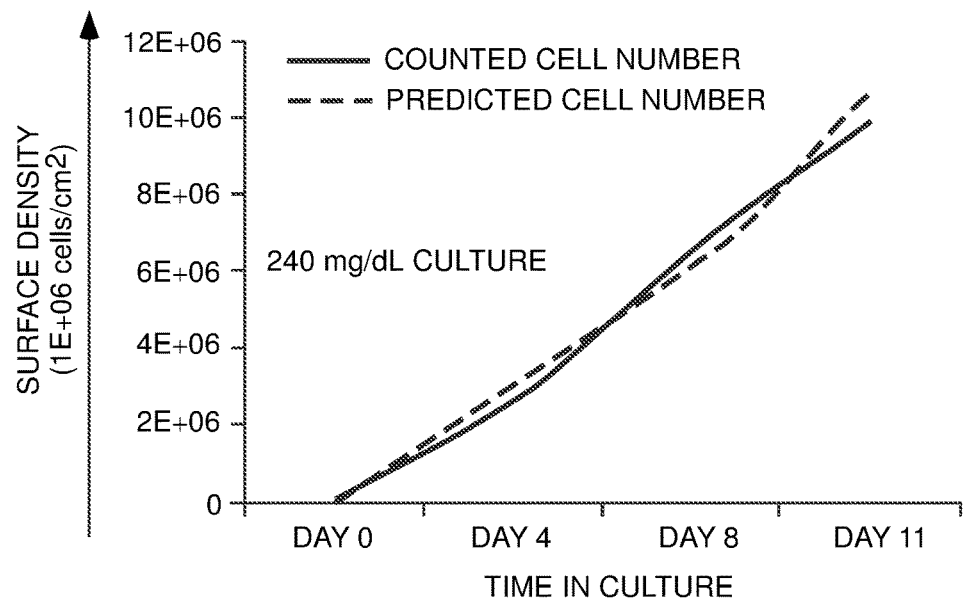
FIG. 19E shows an overlay of the predicted number of cells in a population using the formulaic calculation, versus the number of cells as determined by manual counts for the culture initiated at a glucose concentration of 240 mg/dl.
Figure 19F:
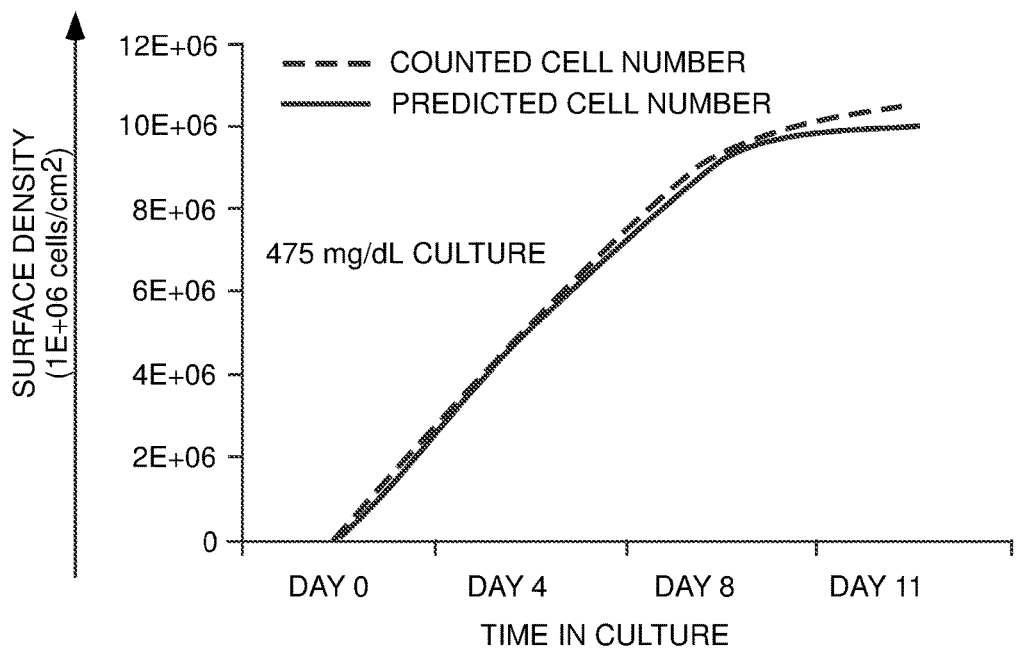
FIG. 19F shows an overlay of the predicted number of cells in a population using the formulaic calculation, versus the number of cells as determined by manual counts for the culture initiated at a glucose concentration of 240 mg/dl.

FIG. 19B shows the population expansion under each condition over a time period of 11 days. The population growth rate differed slightly, but arrived at about the same number in 11 days. FIG. 19C shows the glucose depletion rate in each culture condition. FIG. 19D shows the glucose consumption rate in each culture condition. FIG. 19E shows an overlay of the predicted value, using the formulaic calculation of cell number, versus the cell number as determined by manual counts for the culture initiated at a glucose concentration of 240 mg/dl. FIG. 19F shows an overlay of the predicted value, using the formulaic calculation of cell number, versus the cell number as determined by manual counts for the culture initiated at a glucose concentration of 475 mg/dl. Note the predictive capacity of the formulaic approach relative to the method of manual cell counts. This further demonstrates that various embodiments of the present invention can be utilized in conjunction with a method of reducing, or even eliminating, the frequency of cell counts in lieu of a surrogate measure of the concentration of solutes in the medium.

This is a particularly powerful advantage relative to cell counts when one wishes to use the gas permeable devices described in Wilson '717 or Wilson '176. Skilled artisans will recognize the challenge of getting accurate distribution of cells in such devices and the potential for miscounts due to poor cell distribution into the medium. Thus, a surrogate measure that only relies on a medium sample in lieu of actual cell counts is of great benefit in the field of Adoptive Cell Therapy.

Equipped with this knowledge, manufacturers of gas permeable devices, including those described in Wilson '717 or Wilson '176, could provide a simplified cell production process that can easily determine the number of live cells in culture within a gas permeable device, absent the need to count cells, by providing a gas permeable cell culture device including a growth surface comprised of gas permeable material and providing instructions and/or disseminating information relating to the disclosures of the present invention.

Example 11: Less Complicated Methods of Producing Cells within a Static Gas Permeable Culture Device by Establishing Novel Conditions at the Start of the Culture Process in Order to Limit Feeding Frequency in Static Cultures We undertook a series of experiments to determine the ability to reduce feeding frequency by use of the novel methods disclosed within relative to state of the art culture methods, which require feeding every two to three days.

Experiments were conducted in devices that included growth surfaces with surface areas comprised of gas permeable material and varying capacity for medium height. The following description of an experiment that compared medium volume and feeding frequency are illustrative of our findings. K562 cells and medium were introduced into the devices and they were placed into a cell culture incubator at 37 C, 5% CO2, and 95% R.H, whereby cells were allowed to gravitate to the growth surface at a surface density of 0.125E+06 cells/cm$^2$, determined to be advantageous for superior population fold expansion as previously described.

Medium resided at a height of 2.5 cm, 5.0 cm, 10.0 cm, or 15.0 cm above the growth surface, which was comprised of silicone and had a surface area of 100 cm$^2$. The growth surface was held in a substantially horizontal position with a growth surface support as described more thoroughly in Wilson '717. Thus, experimental conditions included ratios of medium volume to the surface area of growth surfaces at 2.5 ml/cm$^2$, 5.0 ml/cm$^2$, 10.0 ml/cm$^2$, and 15.0 ml/cm$^2$. Thus, initial cell density was 0.05E+06 cells/ml, 0.025E+06 cells/ml, 0.0125E+06 cells/ml, and 0.008E+06 cells/ml respectively.

No further medium was added to the 10.0 ml/cm$^2$ or 15.0 ml/cm$^2$ conditions. The original medium volume of the 2.5 ml/cm$^2$ condition was doubled by adding 2.5 ml/cm$^2$ of fresh medium on day 11, tripled on day 14 by adding another 2.5 ml/cm$^2$ of fresh medium, and quadrupled on day 17 by adding another 2.5 ml/cm$^2$ of fresh medium. The original medium volume of the 5.0 ml/cm$^2$ condition was doubled by adding 5.0 ml/cm$^2$ of fresh medium on day 11. Eventually, the 2.5 ml/cm$^2$ and 5.0 ml/cm$^2$ conditions held 10.0 ml/cm$^2$ of medium.

Figure 20:
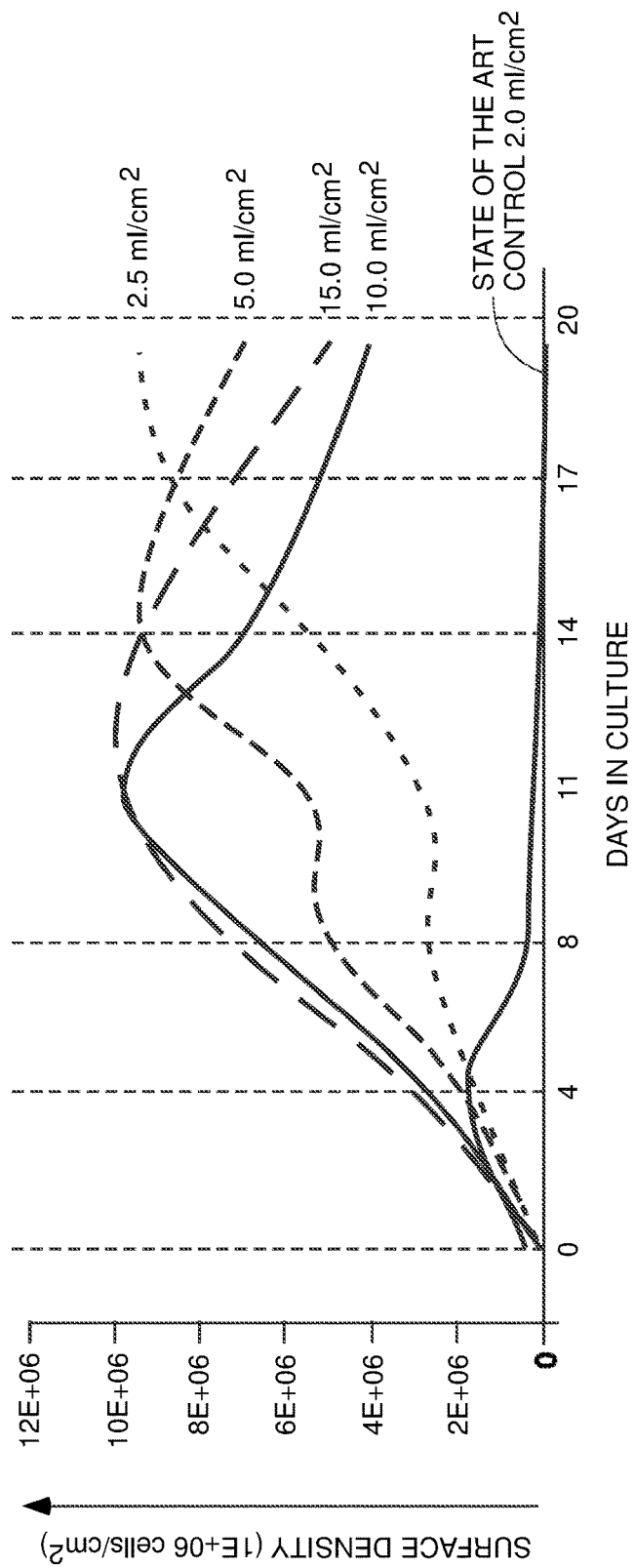
FIG. 20 shows a graphical representation of population growth, normalized for growth surface area, under various medium feeding conditions.

FIG. 20 shows a graphical representation of population growth, normalized for growth surface area, under various medium feeding conditions.

Note that all conditions eventually arrived at about the same number of live cells. However, conditions that did not rely on the addition of medium during the culture arrived at the maximum number of live cells faster than the other conditions. For example, it took 20 days for the 2.5 ml/cm$^2$ condition to arrive at maximum density while it only took 11 days for the conditions that did not receive fresh medium after the onset of culture to arrive at the same maximum number of live cells. Also, the population growth rate was far superior in the unfed conditions. Also of importance, the condition that initiated culture with medium at a height of 15.0 cm showed the capacity to maintain cells in a prolonged duration of high viability relative to the 10.0 cm condition. For example, viability was relatively high in the 15.0 cm for a period of about 4 days after the maximum cell population was attained while it diminished rapidly after about 1 to 2 days in the 10.0 cm condition. The practical benefit created here is a production process that has a longer period of time in which to recover cells. Those of ordinary skill in the art in the field of Adoptive Cell Therapy will recognize the value of this, as there are many reasons why one would derive value from a bigger window of time for cell recovery ranging from a delay in obtaining the results of quality control measures to changing conditions of the patient.

Skilled artisans will recognize that all of the experimental culture conditions exhibited superior rates of cell population expansion compared to state of the art methods for Adoptive Cell Therapy, but should be aware that it is not only beneficial to reduce surface density relative to state of the art methods at the onset of culture, it is further possible to reduce the duration needed for production of desired number of cells by increasing medium height and/or medium to growth area ratios. Skilled artisans should recognize that improvements will be obtained in terms of the rate of population expansion as less surface density and more medium height and/or a further increase in medium volume to growth surface area ratio is undertaken, and are encouraged to balance the use of medium with the needs of the application. More medium at the onset of culture can be provided if a larger window of time to harvest cells while they reside at high viability is sought. Of note, even if one were to start with a surface density at or above that of state of the art, such as at 2.0E+06 or greater, the process can be superior since embodiments of the present invention can diminish feeding frequency and reduce concerns about cell populations quickly losing viability. In general, a wide range of options have been demonstrated. For production of a population of cells with minimal feeding frequency and shortened production duration, a most preferred initial culture condition for production is a cell density of less than 0.5E+06 cells/$cm^2$ and most preferably about 0.125E+06 cells/$cm^2$, and a medium height of about 5.0 cm or more and more preferably 10.0 cm to 15.0 cm, and/or a medium volume to growth surface area of about 5.0 ml/$cm^2$ or more and more preferably 10.0 ml/$cm^2$ to 15.0 ml/$cm^2$, and/or an initial cell density about 0.025E+06 cells/ml or less and more preferably about 0.0125E+06 cells/ml to about 0.008E+06 cells/ml.

Example 12: Novel Ways to Limit Feeding Frequency of Co-Cultures Residing within a Static Gas Permeable Culture Device and Determine the Size of the Cell Population without Need of Counting Cells, Even Though a Portion of the Cells are Dying Adoptive Cell Therapy often relies on co-culture with cells that are dying because they were irradiated (such as APC's) or cells that are dying as a result of being removed from the body (such as PBMC's). A good example of a co-culture application is in the culture of CMV-CTLs (cytomegalovirus specific cytotoxic T lymphocytes) out of a population of PBMCs. Initially, the CMV-CTL population is a very small percentage relative to the total population of PBMCs. As the culture progresses, the PBMC begin to die off and CMV-CTLs begin to grow. By the end of culture, the frequency of CMV-CTL in the cell composition has increased greatly. The previously disclosed characteristics of the present invention, including those that contradict state of the art methods, such as reduced cell density, can be used to diminish feeding frequency for applications such as these.

We conducted static cell culture experiments to assess the ability of glucose measurements to predict cell populations in the presence of dying cells in co-cultures. Experimental devices included a growth surface comprised of gas permeable silicone with a surface area of 100 $cm^2$. The growth surface was comprised of silicone and held in a substantially horizontal position with a growth surface support as described more thoroughly in Wilson '717. FIG. 21 shows a spreadsheet that summarizes conditions on day 0, day 9, and day 16. PBMCs medium were introduced into the experimental devices and the devices were placed into a cell culture incubator at 37 C, 5% CO2, and 95% R.H, whereby cells were allowed to gravitate to the growth surface at a surface density of 5.0E+05 cells/$cm^2$. Medium resided at a height of 10.0 cm and cell density was at 5.0E+04. Glucose measures were taken on day 0, day 9, and day 16. Other than routine handling, the culture medium and cells were not mixed by forced mixing with the aid of mechanical equipment such as is the case with perfusion, shaking, or stirring. Row 3 shows the increase in the percentage of antigen specific T cells (CMV-CTL) increases to about 27.9% of the population of the cell composition, and Row 4 shows how the CMV-CTL fold expansion as a percentage of the total population diminished after day 9. This is because the PBMC are dying.

Row 19 demonstrates the ability of the surrogate measures of solutes in the medium to predict the number of cells in culture. Note that the predicted value is nearly identical to the assessment of cell population by counting. Thus, the ability to use a surrogate measure to quantify cell population is useful even in cell compositions in which components of the cell composition are dying.

Figure 22A:
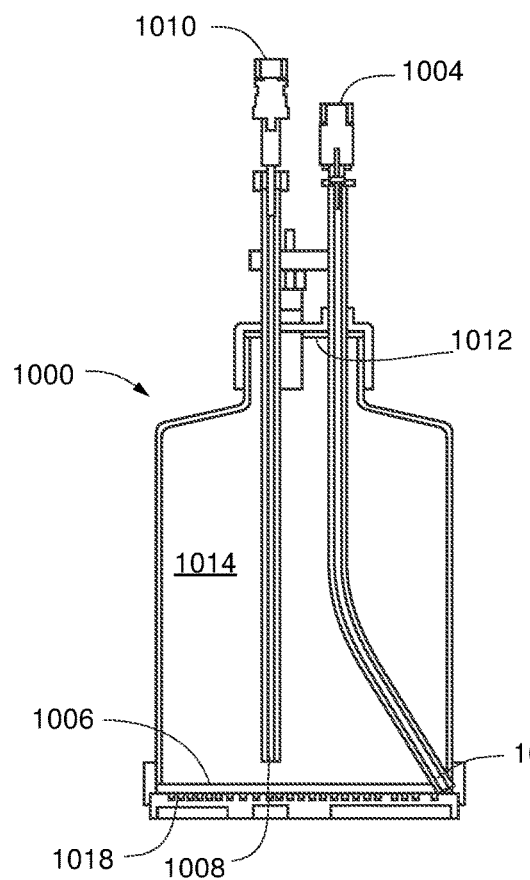
FIG. 22A shows a cross-sectional view of one example of an embodiment of a present invention of a cell culture and cell recovery device 1000 configured to perform the disclosed novel cell culture and/or novel cell recovery methods.

Example 13: Novel Static Gas Permeable Cell Culture and Cell Recovery Devices that Enable Simplified Methods of Medium Exchange and Novel Methods for Greatly Diminishing the Effort Required to Separate Cells from Medium after a Cell Production Process is Complete FIG. 22A shows a cross-sectional view of one example of an embodiment of a present invention of cell culture and cell recovery device 1000 configured to perform the disclosed novel cell culture and/or novel cell recovery methods. Cell removal opening 1002 of cell removal conduit 1004 resides in proximity of growth surface 1006. Medium removal opening 1008 of medium removal conduit 1010 resides near growth surface 1006. Growth surface 1006 is comprised of gas permeable material. There are many sources of information for skilled artisans to learn about appropriate gas permeable material including Wilson '717. Preferably, growth surface 1006 is liquid impermeable and non-porous. The distance from growth surface 1006 to upper confine 1012 of internal volume 1014 defines the volume of space where medium can reside. Although medium can reside in medium removal conduit 1010 and cell removal conduit 1004, which can extend to a height beyond upper confine 1012, maximum medium height should be considered by skilled artisans to be the farthest distance from the bottom of internal volume 1014 to upper confine 1012 for purposes of describing this embodiment. The cell culture and cell recovery device does not require a stirring mechanism or any other mechanisms to mix the cells and/or medium.

Figure 22B:
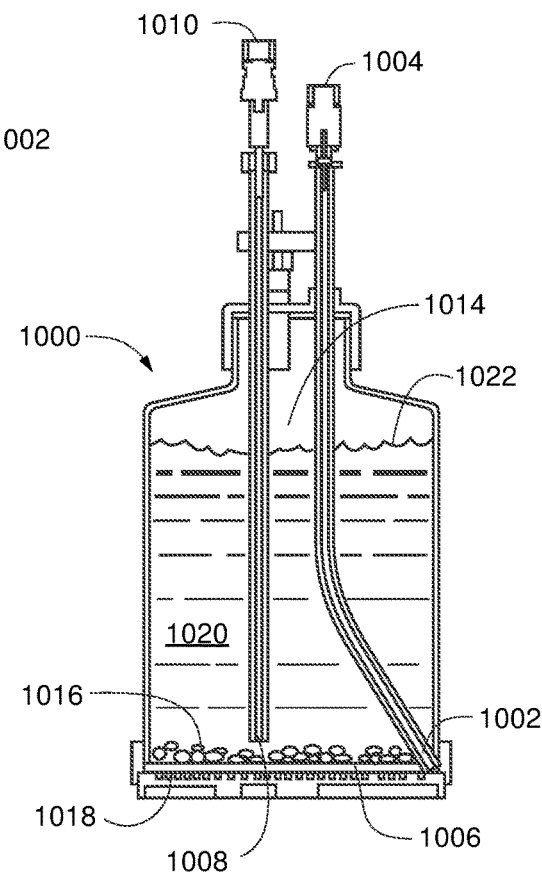
FIG. 22B shows cell culture and cell recovery device 1000 in an initial state of static culture at the onset of any given cell production stage of culture.

FIG. 22B shows cell culture and cell recovery device 1000 in an initial state of static culture at the onset of any given cell production stage of culture. Cell culture and cell recovery device 1000 resides in a position in which growth surface 1006 is in oriented in a horizontal position and cells 1016 have gravitated to growth surface 1006. In this illustrative embodiment, growth surface support 1018 is used to hold growth surface 1006 in a horizontal position while allowing ambient gas to make contact with growth surface 1006 without need of pumps or other mechanisms to force gas past growth surface 1006. Skilled artisans can refer to Wilson '717 for information about how to configure growth surface support 1018. Although medium 1020 can reside at any level within the confines of internal volume 1014, preferably the entire uppermost medium location 1022 is parallel to growth surface 1006 as shown. Cell culture and cell recovery device 1000 resides in an atmosphere suitable for cell culture and at a temperature suitable for cell culture. Ambient gas makes contact with gas permeable material of growth surface 1006 by random motion and without need of pumps or other mechanisms to force gas to or from growth surface 1006.

Medium height is determined by the distance from the lowermost medium location to the uppermost medium location, in this case the distance from growth surface 1006 to uppermost medium location 1022 at the onset of culture being the initial static culture medium height. The ratio of the number of cells 1016 having gravitated to growth surface 1006 to the volume of medium 1020 is an initial static culture cell density. The ratio of the number of cells 1016 upon growth surface 1006 to the surface area of growth surface 1006 is the initial static culture surface density. The ratio of medium 1020 volume to the surface area of growth surface 1006 is an initial static culture medium volume to growth surface area ratio. Cells reside in a state of static culture and the culture continues for a period of time. As described throughout this disclosure, the period of time may or may not include a medium replenishment step depending upon variables that include the initial static culture medium height, the initial static culture cell density, the initial static culture surface density, and/or the initial static culture medium volume to growth surface area ratio.

Figure 22C:
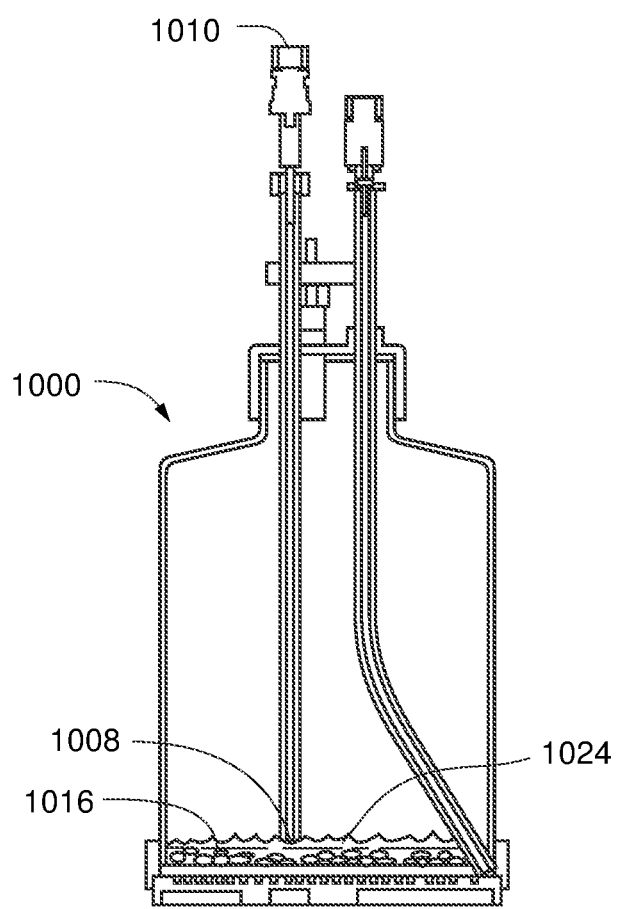
FIG. 22C shows cell culture and cell recovery device 1000 prepared to recover cells in a reduced volume of medium.

FIG. 22C shows further steps to recover cells in a reduced volume of medium from cell culture and cell recovery device 1000. Medium is removed by way of medium removal opening 1008 in medium removal conduit 1010 while not withdrawing cells 1016. After this step, remaining medium is shown as cell recovery medium 1024. The less cell recovery medium that remains, the less complicated the process of separating cells from medium will become, which is inherent to state of the art methods for Adoptive Cell Therapy and currently relies on a great deal of centrifugation. However, it is critical that one take care not to lose a significant amount of cells while reducing the medium volume. Preferably, fewer than 10% of cells are lost and more preferably virtually no cells are lost. For further guidance, we describe an example of our use of this aspect of the present invention. In a gas permeable device similar to that shown in FIG. 22A with a growth surface comprised of gas permeable silicone with a growth surface area of 100 cm$^2$, a culture medium volume of 2000 ml and residing at a height at the point of medium volume reduction of 20 cm, thereby constituting a medium volume to growth surface area of 200 (ml/cm$^2$), and a cultured cell population of about 1 billion cells residing on the growth surface at the point of medium reduction, we have demonstrated the ability to avoid visible loss of cells while simultaneously obtaining a 100 fold reduction in medium volume and establishing a set of conditions at the point of cell recovery that were characterized by cell recovery medium height at a mere 0.2 cm (as determined when the growth surface was in a horizontal position) and a cell recovery medium volume to growth surface area ratio at a mere 0.2 ml/cm$^2$. We then mixed the medium, in this case by swirling the medium in the device, which readily lifted the cells from the growth surface and which distributed them into the cell recovery medium. We then removed the cells by way of a cell removal opening in a cell removal conduit. The cell removal opening was located along the edge of the device and we tilted the device to allow medium to collect at the location of the cell removal opening. Upon collection of cells and cell recovery medium, we examined the cell concentration in the cell recovery medium and it was striking, at about 50 million cells per ml. Thus, we were able to concentrate the cells from an initial cell density of about 0.5 million cells per ml by a factor of 100 without any of the centrifugation equipment used in state of the art methods of static cell culture in Adoptive Cell Therapy, leaving a mere fraction of the culture to be subjected to further processing for cell recovery. In essence, we were able to reduce the volume of medium that needed to be subjected to centrifugation from 2000 ml to just 20 ml and the entire process took less than about 1 minute.

The location of the medium removal opening of the medium removal conduit is preferably located at a distance of 0.2 cm or more from the growth surface when the growth surface resides in a horizontal position. For example, between 0.2 cm and 2.0 cm from the growth surface when the growth surface resides in a horizontal position allows significant volume reduction for many of the cell culture methods of the present invention. The upper limit of the distance between the medium removal opening and the growth surface when the growth surface resides in a horizontal position is preferably a distance that takes into account the typical height of medium at the point where medium is to be decreased for cell recovery. For example, if one seeks to reduce the volume of medium that needs to be centrifuged by 50% relative to state of the art methods of static cell culture, the medium removal opening of the medium removal conduit would be located at 50% of the medium height (assuming the device was designed such that the medium resided entirely over the growth surface). Since use of laboratory space is at a premium, device height should be about the height of medium expected to reside within it. Therefore, to provide the option of getting at least a two-fold reduction in medium volume processing relative to state of the art methods, a good rule of thumb is to design the device with a height that is at or just beyond typical medium height during use and locate medium removal opening of the medium removal conduit at any location from about 0.2 cm from the growth surface (when the growth surface resides in a horizontal position) to about the halfway point from the top of the device to the growth surface as measured from the inside of the device. For example, if the distance from the upper confine of growth medium in the device to the growth surface represents the potential height of medium in the device, the medium removal opening would preferably be located 0.2 cm or more above the growth surface when the growth surface resides in a horizontal position and 50% or less of the potential medium height. In the event it is uncertain where the medium height will reside, more than one medium removal conduit could be present in the device.

Figure 22D:
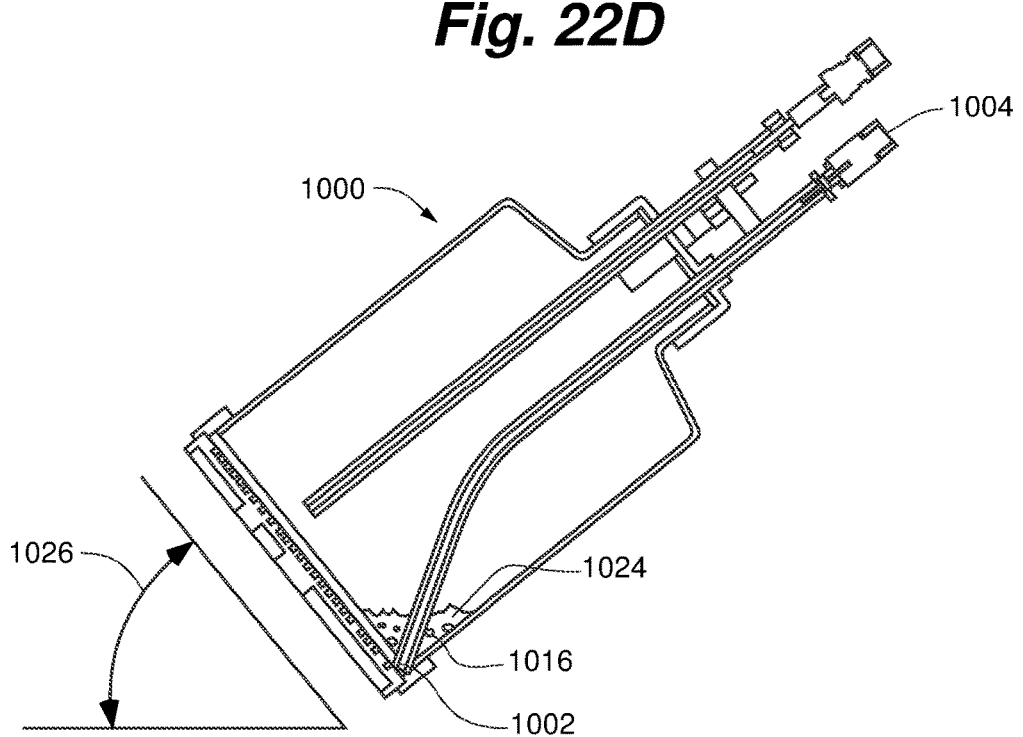
FIG. 22D shows the process of reorienting cell culture and cell recovery device 1000 into a position at an angle 1026 that deviates from the original horizontal cell culture position in order to relocate cell recovery medium 1024.

The cell removal opening of the cell removal conduit is preferably located along the lower edge of the device and can collect cell recovery medium without reorienting the device. However, the device can be reoriented if desired. FIG. 22D shows the process of reorienting cell culture and cell recovery device 1000 into a position at an angle 1026 that deviates from the original horizontal cell culture position in order to relocate cell recovery medium 1024, having cells 1016 distributed within it, relative to cell removal opening 1002 of cell removal conduit 1004, whereby cell recovery medium 1024 can subsequently be withdrawn.

However, the cell removal opening of the cell removal conduit need not be located along the lower edge of the device. Once the step of mixing the cells in the cell recovery medium is complete, the cell recovery medium can be removed from any location in the device by simply rotating the device until the cell recovery medium is located at the cell removal opening, and then withdrawing the cell recovery medium by way of the cell removal conduit. Skilled artisans should recognize that the conduits need not be as shown, but can be any configuration. The key design feature is the ability to place the medium removal opening in the preferred locations relative the growth surface as previously described. Thus, the conduits can be as simple as locating a septum in the side of the device or as complex as telescoping tubes. Also skilled artisans should be aware that the method of cell culture and cell recovery need not rely on closed system configurations, but can be practiced by simple means in open system configuration also. For example, we have conducted the method and repeated the steps described above with an open system device of the type described in Wilson '717 with use of a pipette as the medium removal conduit and as cell removal conduit while achieving the concentrations described above.

To capture the advantages of increased cell culture medium volume to growth surface area ratios described in various embodiments of the present invention, the internal height of the cell culture and cell recovery device should preferably be at least more than 2.0 cm in any particular application. Also, to facilitate cell culture and cell recovery, the cell culture and cell recovery device is preferably constructed with biocompatible materials, clear to allow visual assessment, and rigid to allow easy handling.

The discovery of a method for removing medium from the cell culture and cell recovery device of the present invention without removing cells creates additional advantages relative to state of the art static cell culture methods for Adoptive Cell Therapy and are related to the medium exchange process. Although the present disclosure describes novel methods that avoid removal and replacement of medium in order to replenish medium, there may be circumstances where an artisan may wish to perform that process. State of the art methods lead to cell removal when medium is removed and replaced and thus, the common practice is to remove medium, distribute it to one or more new devices, and add medium to all the devices. Thus, more and more devices are present whenever feeding occurs. This need not occur with our novel methods, as the cell recovery methods of our present invention leaves cells in the device when medium is removed by use of a conduit that can be as simple as a pipette. There is no need for the use of any screens, filters, or centrifugation of the device to reduce the medium volume without cell loss. Medium can simply be removed and added to the same device until the cell population is at a maximum surface density.

In the case of medium removal and replacement, having already described how one can remove medium to a height of merely 0.2 cm without cell loss, it is easy to see now to perform medium exchange by simply removing medium to the desired height and/or volume by way of the medium removal opening of the medium removal conduit without cell removal, and then adding medium to any volume or height desired.

Thus, equipped with this disclosure, a skilled artisan should seek to create a preferred embodiment of a static gas permeable cell culture and cell recovery device comprising:

a. a growth surface comprised of gas permeable material, and
b. the growth surface residing in a horizontal position when the device is in operation, and
c. a medium removal conduit including a medium removal opening, and
d. a cell removal conduit including a cell removal opening, and
e. an internal volume, and
f. an upper confine bounding the uppermost location of the internal volume g. the distance from the upper confine to the growth surface being the potential medium height and the distance from the upper confine to the growth surface being beyond 2.0 cm, and
h. the distance the medium removal conduit resides above the growth surface at least 0.2 cm above the growth surface when the growth surface resides in a horizontal position, and no more than 50% beyond the potential medium height.

The device should preferably include relevant aspects of devices described in Wilson '717. Also, equipped with this knowledge, manufacturers of gas permeable devices, including those described in Wilson '717, could facilitate more efficient methods of cell culture by providing users with a cell culture and cell recovery device including a growth surface comprised of gas permeable material, a medium removal conduit, a medium removal opening, a cell removal conduit, a cell removal opening, and providing instructions and/or disseminating information for:

a. adding cells and medium into the device, and
b. the cells being of a mammalian and of a non-adherent cell type, and
c. placing the cell culture and cell recovery device in an atmosphere suitable for cell culture and at a temperature suitable for cell culture and with the growth surface being oriented in a horizontal position and the cells residing upon the growth surface, and
d. allowing the cells to gravitate to said growth surface, and
e. the ratio of the number of the cells having gravitated to the growth surface to the volume of the medium being an initial static culture cell density, and
f. the ratio of the number of the cells having gravitated to the growth surface to the surface area of the growth surface being an initial static culture surface density, and
g. the ratio of the medium volume to the surface area of the growth surface being an initial static culture medium volume to growth surface area ratio, and
h. the distance from the lowermost medium location to the uppermost medium location being an initial static culture medium height, and
i. allowing a period of time for cells to reside in a state of static culture and further including steps for recovering cells from the cell culture and cell recovery device comprising:
j. a pre cell recovery step comprising removing a portion of medium by way of the medium removal opening in a cell removal conduit and not withdrawing cells, the remaining volume of medium in the device being a cell recovery medium volume, and
k. the distance from the uppermost location of the cell recovery medium to the lowermost location of the cell recovery medium when the growth surface resides in the horizontal position being a cell recovery medium height, and
l. the ratio of the volume of the cell recovery medium to the surface area of the growth surface being a cell recovery medium volume to growth surface area ratio, and
m. the ratio of the cell recovery medium volume to the medium volume being the medium reduction percentage, and a cell recovery step comprising:
n. mixing the cells into the cell recovery medium, and
o. the ratio of the number of cells in the recovery medium to the volume of the cell recovery medium being a recovered cell density, and p. removing the cells and the cell recovery medium from the cell culture and cell recovery device by way of said cell removal opening in a cell removal conduit.

Preferably, the cell recovery medium volume to growth surface area ratio is at least 0.2 ml/cm$^2$ and the medium reduction percentage being at least 50%. Skilled artisans are advised that this method is capable of utilizing any of the embodiments of the present invention including the desired initial static culture cell density, initial static culture surface density, initial static culture medium volume to growth surface area ratio, and/or initial static culture medium height that provide advantages described herein. Also, skilled artisans are encouraged to recognize that the method includes use for islets.

Example 14: Novel Methods of Using a Static Gas Permeable Culture Device for Superior Production of CAR T Cells Experiments were conducted in experimental devices that included growth surfaces with surface areas comprised of gas permeable material and varying capacity for medium height. The growth surface was comprised of silicone with a 100 cm$^2$ surface area and held in a substantially horizontal position with a growth surface support as described more thoroughly in Wilson '717.

Three conditions for expansion of transduced antigen specific T cells (CAR T cells) were evaluated. Evaluation A included CAR T cells in the presence of K652 APC cells and included medium height at 10 cm. Evaluation B included CAR T cells without the presence of K652 APC cells and included medium height at 10 cm. Evaluation C cultured CAR T cells in accordance with state of the art methods.

FIG. 23A shows the conditions of Evaluation A at the onset of culture and as the culture progressed. Of note, the ratio of APC to CAR T cells at the onset of culture was 2:1 and medium resided at a height of 10 cm. FIG. 23B shows the conditions of Evaluation B at the onset of culture and as the culture progressed. Of note, APC were not present at the onset of culture and medium resided at a height of 10 cm. FIG. 23C shows the conditions of Evaluation C at the onset of culture and as the culture progressed. Of note, the ratio of APC to CAR T cells at the onset of culture was 2:1 and medium resided at a height of 2 cm.

Unlike state of the art cultures in the field of Adoptive Cell Therapy, cytokine stimulation is undertaken during medium exchange by adding cytokine (such as IL2) to the fresh medium. Thus, cytokine stimulation is simultaneous with medium exchange. However, as disclosed in various embodiments of the present invention, feeding frequency is greatly reduced and even eliminated. Thus, we also used Condition A and Condition B to evaluate the capacity to add cytokine in the absence of medium exchange. In lieu of medium exchange we simply added a bolus of IL2 at the same frequency and at a quantity that brought the medium the same quantity per ml of state of the art methods and did not subject the medium to forced mixing of any sort to distribute the IL2 within the medium.

Figure 23D:
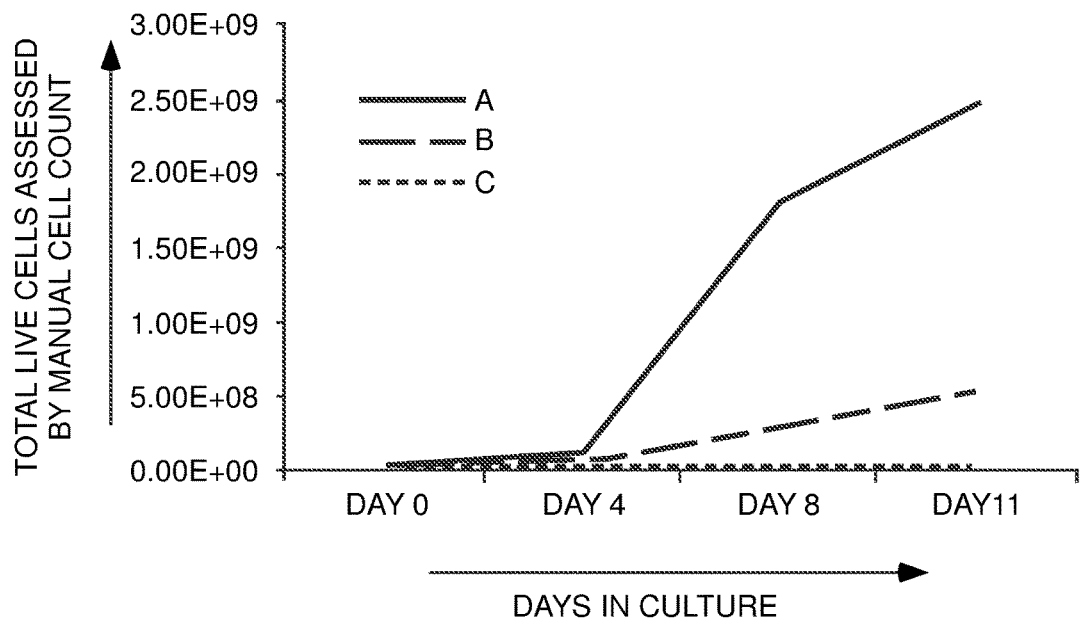
FIG. 23D shows the total live cells in culture at various time points in the culture.
Figures 1, 23E:
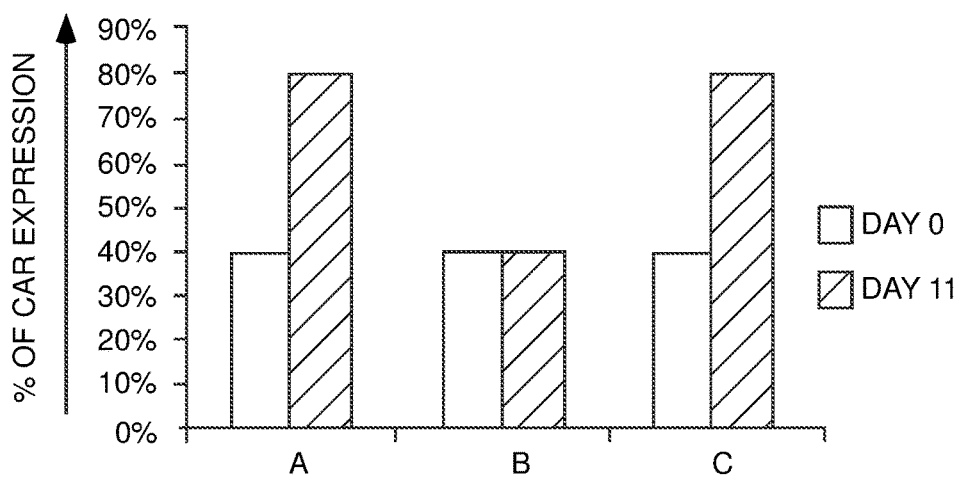
FIGS. 23E1-E3 show the percentage of CAR T cell expression at the onset of culture and at the completion of culture.
Figures 2, 23E:
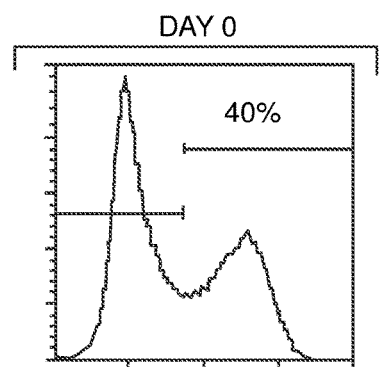
FIG. 2 shows a table that illustrates the discrepancy between the potential expansion and observed fold expansion of antigen-specific T-cells in Example 1.
Figures 3, 23E:
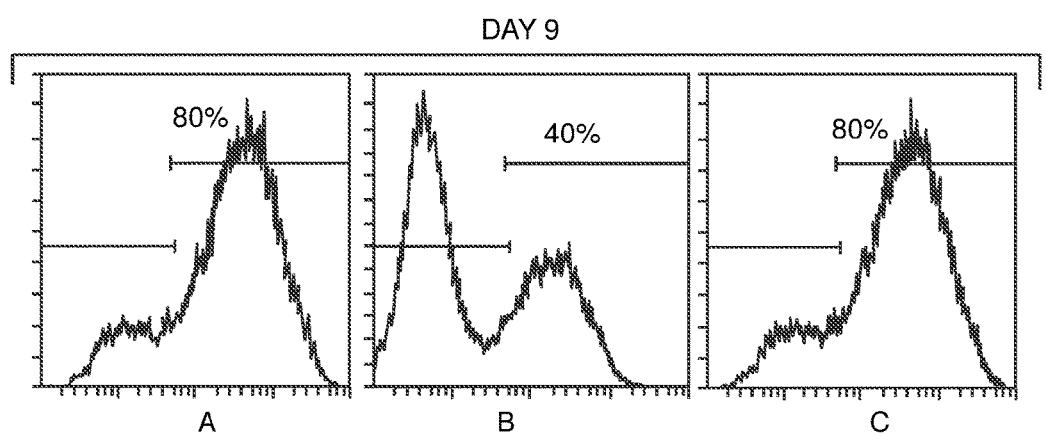
Figure 23F:
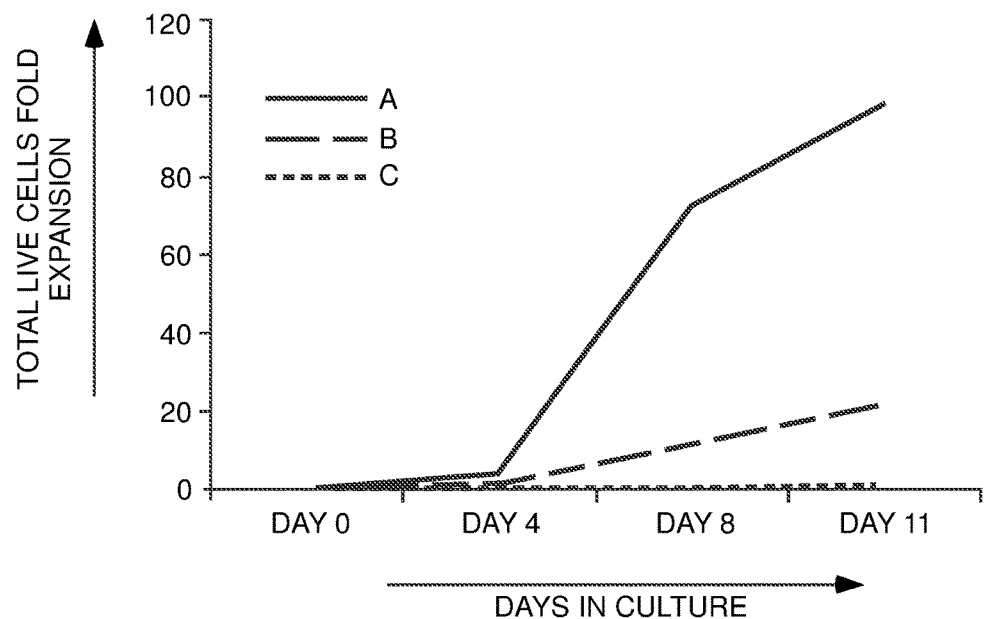
FIG. 23F shows the total fold expansion of CAR T cells during culture.

FIG. 23D shows the total live cells in culture at various time points in the culture. As can be seen, the number of total live cells of Condition A were far superior to either of the alternative conditions. FIG. 23E1-E3 show the percentage of CAR T cell expression at the onset of culture and at the completion of culture. Histogram A represents Condition A, histogram B represents Condition B, and histogram C represents Conditions C. Condition B demonstrates the disadvantage of not providing APC in the culture at culture onset. When APC's were provided at the onset of culture, CAR expression improved from an initial state of about 40% to a state of about 80% by the end of culture. FIG. 23F shows the total fold expansion of CAR T cells during culture. It is clear that Condition A was able to generate a tremendously greater fold expansion than state of the art methods shown in Condition C.

Figure 23G:
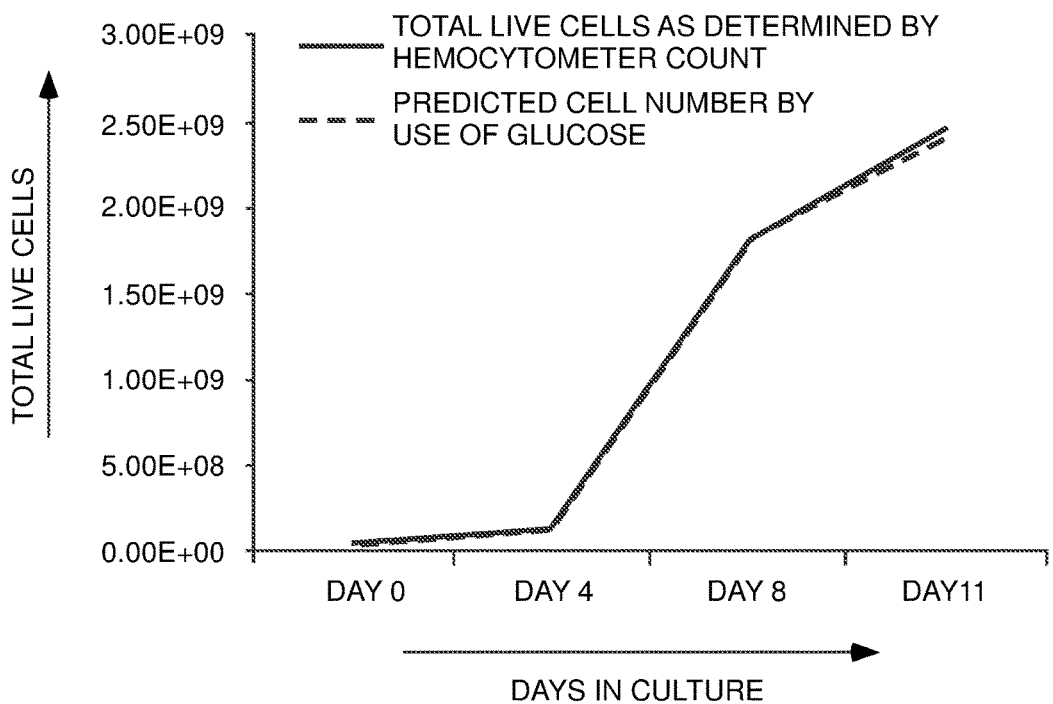
FIG. 23G demonstrates the prediction of the live cell population in Evaluation A was representative of cell population as determined by manual counts.

Also of note, as shown in FIG. 23G, prediction of the live cell population in Evaluation A was representative of cell population as determined by manual counts. Furthermore, the devices used for Evaluation A and Evaluation B were able to have medium withdrawn at the end of culture, using the methods previously disclosed, from a state of 1000 ml to a state of 20 ml without cell loss.

Another important finding was related to the presence of APC in culture. Clearly, the T cells recovered from Condition A have a greater capacity to kill tumor cells that express the relevant antigen (PSCA) due to a more enhanced T cell product, which at the end of the culture has a greater percentage of CAR expressing T cells (CAR-PSCA) in the population relative to its state at the onset of culture. By comparison, Condition B, due to its lack of APCs at the onset of culture, is unable to increase the percentage of CAR expressing T cells (CAR-PSCA) in the cell population at all over the culture period.

Figures 23H, 24A, 24B:
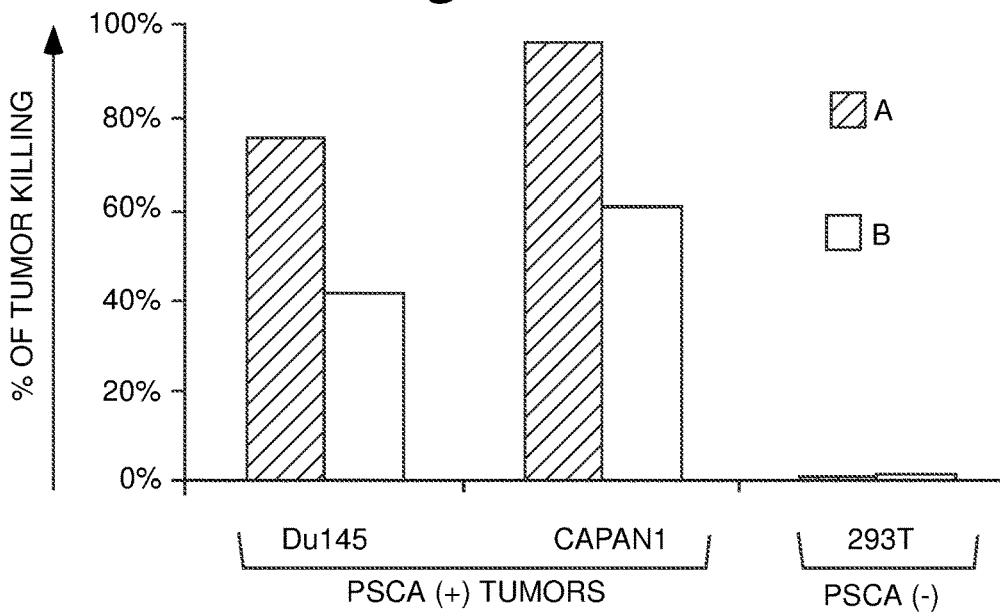
FIG. 23H shows the capacity of cells obtained from Condition A and Condition B to kill tumor cells expressing PSCA.
FIG. 24A is a side by side comparison of the population expansion of CAR T cells specific to PSCA.
FIG. 24B is a side by side comparison of the population expansion of CAR T cells specific to Muc1.

FIG. 23H shows the capacity of cell obtained from Condition A and Condition B to kill tumor cells expressing PSCA, and to avoid killing cells that do not express the PSCA antigen. The ratio of effector cells to PSCA antigen expressing cells (Du145 and Capan1) or non-PSCA antigen expressing cells (293T) was 40:1. Effector cells (i.e. CAR T cells) were obtained from the cultures of Condition A and of Condition B at day 11 of culture.

FIGS. 24A, 24B, 24C, and 24D summarize side by side comparisons of the population expansion of CAR T cells specific to PSCA and Muc1 using the initial culture conditions described for Condition A (the exception being the antigen expression of the APC was PSCA and Muc1 respectively). It can be seen that the novel initial conditions of the present invention were able to produce a far greater number of CAR T cells in a shorter period of time than state of the art conditions in conventional culture ware. Skilled artisans will recognize the advantages are not limited to CAR T cells recognizing PSCA or Muc1 antigens, but are applicable to CAR T cells recognizing any antigen.

The capacity to produce more cells in a shorter time period, add cytokine without need of medium exchange or forced mixing of the medium, eliminate the need to feed the culture with fresh medium, avoid the need to count cells manually, and reduce the amount of medium the cells reside in at the time of cell recovery to just 2% of the volume present at the end of culture demonstrated the power of the present invention to overcome many of the problems inherent to state of the art methods for the production cells for Adoptive Cell Therapy.

Example 15: The Methods of Present Invention are Scalable in Direct Proportion to the Surface Area of the Growth Surface We undertook experiments to assess scalability of the culture processes described herein and in the parent case. The ability to move from a small growth area to a large growth area without need of re-establishing protocols to optimize the culture process is a powerful advantage. To determine if that were the case, we compared outcomes of K562 cultures initiated on growth surfaces comprised of gas permeable silicone, with surface areas of 10 cm$^2$, 100 cm$^2$, and 640 cm$^2$. Initial conditions included a surface density of 0.125E+06 cells/cm$^2$ and a medium height of 10 cm. No medium replenishment was undertaken after the onset of culture.

Figure 24C:
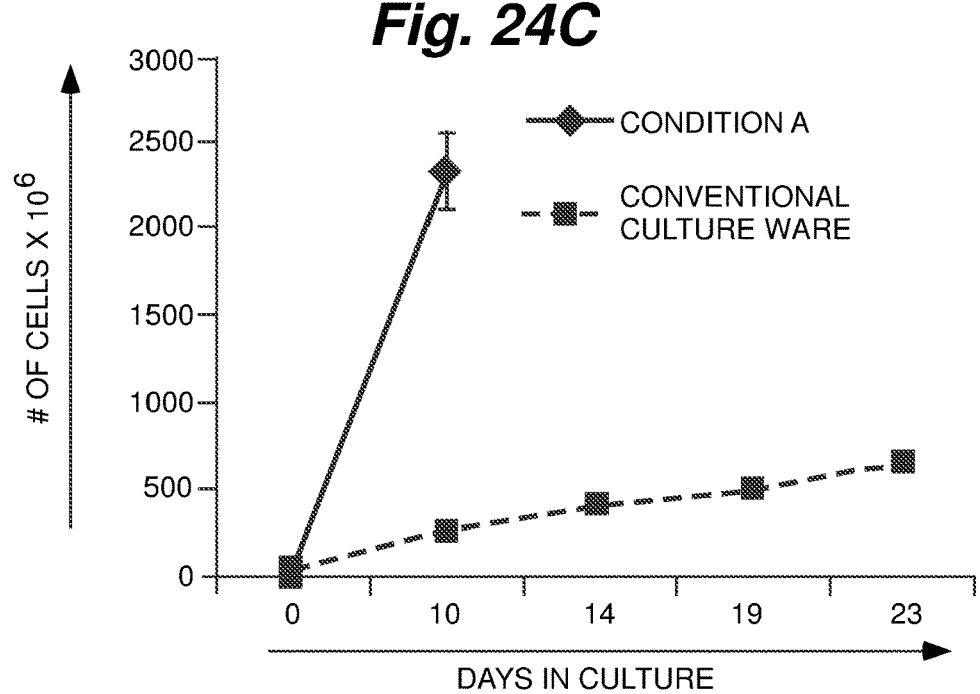
FIG. 24C is a graph of population expansion of CART cells.
Figure 24D:
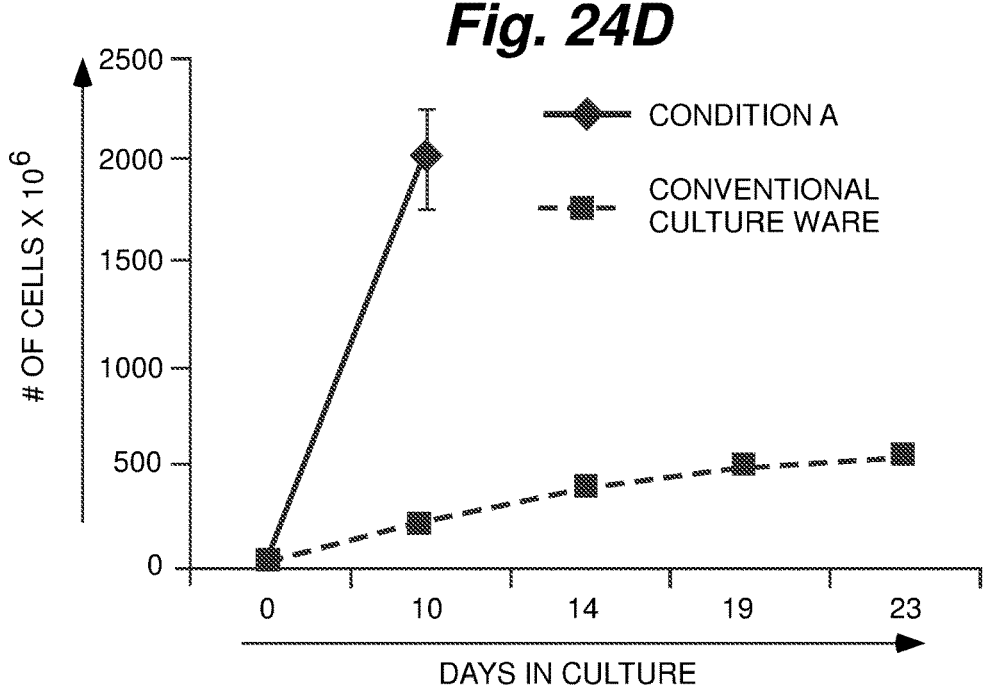
FIG. 24D is a graph of population expansion of Muc1 cells.
Figure 24E:
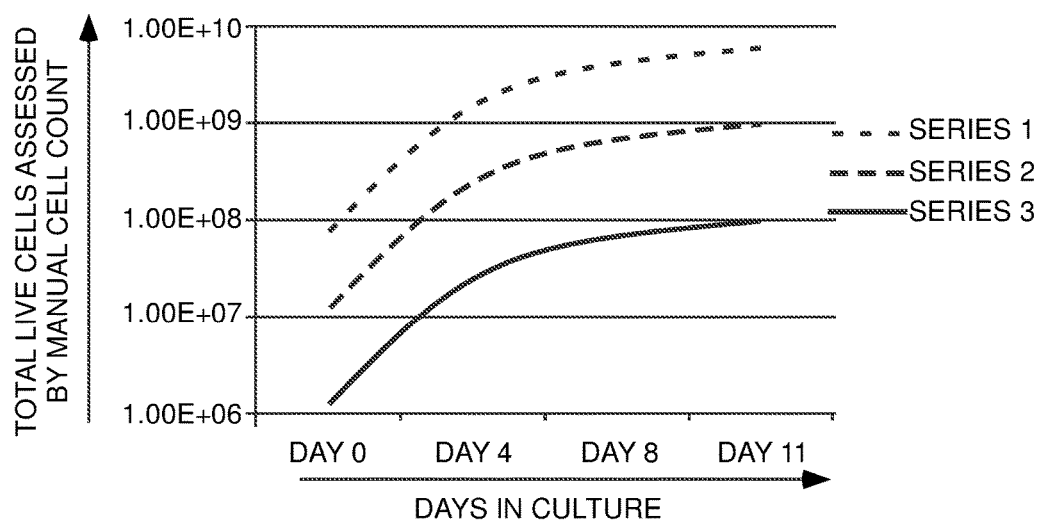
FIG. 24E shows the population growth curves of three gas permeable culture devices with differing growth areas.
Figure 24F:
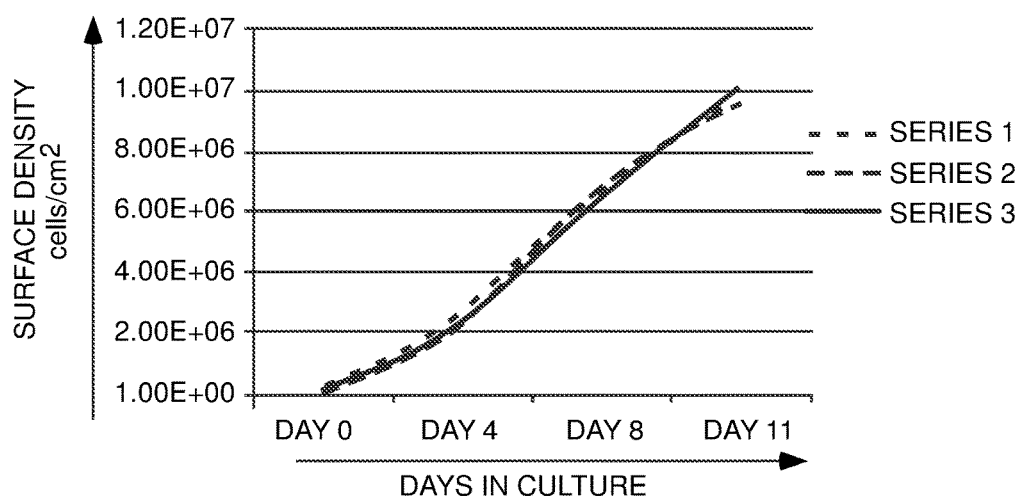
FIG. 24F shows the population growth of FIG. 24E curves after being normalized to surface density.

FIG. 24E shows the population growth curves of three gas permeable culture devices with differing growth areas. Series 1 represents the live cell expansion of culture in the 640 cm$^2$ device, series 2 the 100 cm$^2$ device, and series 3 the 10 cm$^2$ device. FIG. 24F shows the population growth curves of FIG. 24E curves normalized to surface density and clearly demonstrates linear scalability.

Skilled artisans are encouraged to review Wilson '176 in the event that they seek to increase the growth surface area by scaling the culture in the vertical direction and will recognize that many of the embodiments of the present invention can be undertaken using devices described in Wilson '176.

General Description of Preferred Embodiments:

For the purposes of this disclosure, growth surface is the area in a device upon which cells reside and is comprised of gas permeable material. Gas permeable material can be any materials know to skilled artisans in the field of cell culture and are preferably liquid impermeable and non-porous. The devices and culture methods of the present invention can function in the absence of gas being forced past the growth surface that is comprised of gas permeable material. These methods pertain to static cell culture.

Preferred Cell Types:

In embodiments of the present invention, if the culture comprises a single cell type, the cells are preferably antigen presenting cells, and more preferably LCL or K562. If the culture comprises a co-culture, preferably it includes effector cells (i.e. desired or target cells) in combination with APC or feeder cells and may or may not include beads. Beads may also be a substitute for APC or feeder cells. If APC's are present, preferably they are professional antigen presenting cells, and more preferably of the type K562 or LCL, and even more preferably are irradiated. If present, unless they are islets, effector cells are preferably derived from peripheral blood or marrow, and more preferably are T cells, NK, Treg, TIL, or MIL. If effector cells are T cells, preferably they are naturally occurring antigen specific T cells or transduced antigen specific T cells.

Preferred Surface Density:

In embodiments of the present invention, cells reside upon a growth surface comprised of gas permeable material and at a preferred surface density less than 0.5E+06. Skilled artisans will recognize that the disclosure allows an analogue reduction in surface density from less than 0.5E+06 in order to increase rate population expansion relative to state of the art methods in the field of Adoptive Cell Therapy, with more and more reduction being preferred. Thus, for example, we have demonstrated the rate of population expansion with surface density of 0.25E+06, 0.125E+06, and 0.0625E+06 exceeds that of state of the art methods. Thus, skilled artisans are encouraged to recognize that surface density need not be limited to just the stated values of our examples, the possibilities are not discrete values, but instead are analogue. For example, those of ordinary skill in the art are advised that initiating culture at a surface density of 0.49E+06 would allow improved "fold expansion" of the population relative to initiating culture at surface density of 0.5E+06 even though we have not provided an example with that particular surface density. Skilled artisans are thus advised to take the analogue interpretation of surface densities presented in the examples of the present invention and in the parent case, and are not limited to the discrete values presented herein.

Preferred Cell Density:

In embodiments of the present invention, cells reside upon a growth surface comprised of gas permeable material and at a preferred cell to medium density of less than 0.5E+06. Skilled artisans will recognize that the disclosure allows an analogue reduction in cell to medium density from less than 0.5E+06 in order to decrease the frequency of medium replenishment relative to state of the art methods in the field of Adoptive Cell Therapy, with more and more reduction being preferred. Thus, for example, we have demonstrated how to reduce the frequency of medium replenishment be decreasing the cell to medium density from the 0.5E+06 cell/ml lower limit of state of the art methods, while simultaneously being able to maintain a cell population that can expand at a rate that exceeds that of state of the art methods. Skilled artisans are encouraged to recognize that surface density need not be limited to just the stated values of our examples, the possibilities are not discrete values, but instead are analogue. Preferably, skilled artisans should seek to reduce cell to medium density below 0.5E+06 to any particular value they see fit given the attributes they wish to obtain. Therefore, although we describe advantages of reducing cell to medium density with discrete cell to medium density identification in various examples here and in the present case, the present invention is not limited to the discrete numbers presented herein.

Increased Medium Volume to Growth Surface Area Ratio:

In embodiments of the present invention, cells reside upon a growth surface comprised of gas permeable material and advantages accrue by increasing the ratio of medium volume to the surface area of the growth surface. Skilled artisans will recognize that the disclosure allows an analogue increase in the ratio of medium volume to the surface area of the growth surface order to provide numerous advantages when combined with other elements of the present invention such as reduced surface density. Therefore, although we describe these related advantages by use of examples that have discrete values here and in the parent case, the present invention is not limited to the discrete numbers presented herein, and those of ordinary skill in the art are encouraged to recognize the values, and combinations of values, presented are guiding them to obtain the described advantages by analogue interpretation of the values. Thus, the present invention is not limited to the discrete numbers presented herein.

Increased Medium Height:

In embodiments of the present invention, cells reside upon a growth surface comprised of gas permeable material and advantages accrue by increasing height of medium relative to state of the art methods. Skilled artisans will recognize that the disclosure allows an analogue increase in the height of medium in order to provide numerous advantages when combined with other elements of the present invention such as reduced surface density. Therefore, although we describe these related advantages by use of examples that have discrete values here and in the parent case, the present invention is not limited to the discrete numbers presented herein, and those of ordinary skill in the art are encouraged to recognize the values, and combinations of values, presented are guiding them to obtain the described advantages by analogue interpretation of the values. Thus, the present invention is not limited to the discrete numbers presented herein.

Surrogate Measures of the Rate of Solute Change in Medium in Lieu of Counting Cells:

In embodiments of the present invention, cells reside upon a growth surface comprised of gas permeable material and advantages accrue by the ability to determine how many cells are in culture without having to count cells. Skilled artisans will recognize that the disclosure shows examples of how the decay in glucose concentration provides a measure of cell number in culture. Skilled artisans will also recognize that glucose is but one measurable substrate within medium that is utilized by cells, and that one of ordinary skill in the art, given the disclosure of this invention, could rely on the concentration depletion and/or increase of other substrates in the medium to indicate cell number, such as lactate. Thus, the inventive aspect of this embodiment of the invention is the finding that measure of substrates in static cultures that are initiated with any of the novel surface densities, cell densities, medium heights, and/or medium volume to growth area conditions is a good way to determine the progress of expansion of a population of cells. Thus, the present invention is not limited to a glucose substrate. Thus, the present invention is not limited to the discrete numbers presented herein.

Removal of Medium without Cell Loss:

In embodiments of the present invention, cells reside upon a growth surface comprised of gas permeable material in various advantageous surface densities and can reside under an increased height of medium (and/or an increased medium volume to growth surface area ratio) relative to state of the art methods. Advantages accrue by subsequently decreasing medium height (and/or a decreased medium volume to growth surface area ratio) absent cell loss relative to state of the art methods. Skilled artisans will recognize that the disclosure allows an improved method of medium exchange (in which more devices need not be added to the process) and/or an improved method of cell recovery (in which a smaller volume of medium must be processed to recover cells). Although we describe these related advantages by use of examples that have discrete values, the present invention is not limited to the discrete numbers presented herein, and those of ordinary skill in the art are encouraged to recognize the values, and combinations of values, presented are guiding them to obtain the described advantages by analogue interpretation of the values. For example, medium can reside at any height, preferably beyond 2.0 cm (such as 2.1 cm, 2.5 cm, 6.08 cm, 10.0 cm and on). The medium removal opening of the medium removal conduit, preferably at 0.2 cm or more above the growth surface, can therefore preferably reside at any height of 0.2 cm and beyond so long as it resides below the medium height at the time of medium removal without cell loss, thereby diminishing cell separation from medium and/or not forcing users to move cells to additional devices during medium exchange. Thus, the present invention is not limited to the discrete numbers presented herein.

Gas Permeable Culture Devices:

In embodiments of the present invention, we describe discoveries including the capacity for cultures to be initiated at surface densities below the limits of conventional wisdom, minimal manipulation to provide cytokines, medium provision strategies that increase the growth rate of a population of cells relative to state of the art methods and reduce production duration novel cell culture devices, including improvement to methods of Wilson '717 and Wilson '176. Furthermore, device manufacturers and suppliers should recognize that the provision of gas permeable devices, including those described in Wilson '717 and Wilson '176, should include dissemination of novel methods of the present invention and/or of the parent case to the users of such devices by way of instructions, protocols, and the like no matter the form (paper, electronic, website, etc.). Thus, the scope of the present invention includes the provision of instructions and/or dissemination of the methods of the present invention by manufacturers and/or suppliers of gas permeable devices.

The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their equivalents.

Each of the applications, patents, and papers cited in this application and as well as in each document or reference cited in each of the applications, patents, and papers (including during the prosecution of each issued patent; "application cited documents"), pending U.S. Publication Nos. 2005/0106717 A1 and 2008/0227176 A1, and each of the PCT and foreign applications or patents corresponding to and/or claiming priority from any of these applications and patents, and each of the documents cited or referenced in each of the application cited documents, are hereby expressly incorporated herein.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

Those skilled in the art will recognize that numerous modifications can be made to this disclosure without departing from the spirit of the inventions described herein. Therefore, it is not intended to limit the breadth of the invention to embodiments and examples described. Rather, the scope of the invention is to be interpreted by the appended claims and their equivalents.

What is claimed is:

1. A static culture method for expanding a population of cells with a gas permeable cell culture device having
    a growth surface comprised of liquid impermeable gas permeable material, at least a portion of said gas permeable material in contact with an ambient gas,
the method comprising:
    adding a population of desired cells and a population of antigen presenting and/or feeder cells and a medium into the gas permeable cell culture device, a ratio of the volume of said medium to a surface area of said growth surface being 2.5 ml/cm$^2$ to 15 ml/cm$^2$,
    commencing a static cell culture with the ambient gas suitable for the static cell culture making contact with said gas permeable material and in an orientation wherein said desired and antigen presenting and/or feeder cells reside upon at least a portion of said gas permeable material, adding fresh medium after 4 days from the time the static cell culture commenced, terminating the static cell culture beyond 4 days from the time the static cell culture commenced, and when the size of the population of desired cells exceeds the size of the population of antigen presenting and/or feeder cells.

2. The method of claim 1 wherein the static cell culture is not terminated until some point in time beyond 5 days.

3. The method of claim 1 wherein the static cell culture is not terminated until some point in time beyond 6 days.

4. The method of claim 1 wherein the static cell culture is not terminated until some point in time beyond 7 days.

5. The method of claim 1 wherein the static cell culture is not terminated until some point in time beyond 8 days.

6. The method of claim 1 wherein the static cell culture is not terminated until some point in time beyond 9 days.

7. The method of claim 1 wherein the static cell culture is not terminated until some point in time beyond 10 days.

8. The method of claim 1 wherein the static cell culture is not terminated until some point in time beyond 11 days.

9. The method of claim 1 wherein the static cell culture is not terminated until some point in time beyond 12 days.

10. A static culture method for expanding a population of cells with a gas permeable cell culture device having a growth surface comprised of a liquid impermeable gas permeable material, at least a portion of said gas permeable material in contact with an ambient gas, the method comprising:

adding a population of desired cells and a population of antigen presenting and/or feeder cells and a medium into the gas permeable cell culture device, the ratio of the volume of said medium to a surface area of said growth surface being at least 5 ml/cm$^2$ to 15 ml/cm$^2$, commencing a static cell culture with the ambient gas suitable for a cell culture making contact with said gas permeable material and in an orientation wherein said desired and antigen presenting and/or feeder cells reside upon at least a portion of said gas permeable material, adding fresh medium after 8 days from the time the static cell culture commenced, terminating the static cell culture after 8 days from the time the static cell culture commenced, and when the size of the population of desired cells exceeds the size of the population of antigen presenting and/or feeder cells.

11. The method of claim 10 wherein the static cell culture is not terminated until some point in time beyond 9 days.

12. The method of claim 10 wherein the static cell culture is not terminated until some point in time beyond 10 days.

13. The method of claim 10 wherein the static cell culture is not terminated until some point in time beyond 11 days.

14. The method of claim 10 wherein the static cell culture is not terminated until some point in time beyond 12 days.

15. The method of claim 10 wherein the static cell culture is not terminated until some point in time beyond 13 days.

16. A static culture method for expanding a population of cells with a gas permeable cell culture device having a growth surface comprised of a liquid impermeable gas permeable material, at least a portion of said gas permeable material in contact with an ambient gas, the method comprising:

adding a population of desired cells and a population of antigen presenting and/or feeder cells and a medium into the gas permeable cell culture device, a ratio of the volume of said medium to a surface area of said growth surface being at least 10 ml/cm$^2$ to 15 ml/cm$^2$, commencing a static cell culture with ambient gas suitable for the static cell culture making contact with said gas permeable material and in an orientation wherein said desired and antigen presenting and/or feeder cells reside upon at least a portion of said gas permeable material, adding fresh medium after 10 days from the time the static cell culture commenced, terminating the static cell culture after 10 days from the time the static cell culture commenced, and when the size of the population of desired cells exceeds the size of the population of antigen presenting and/or feeder cells.

17. The method of claim 16 wherein the static cell culture is not terminated until some point in time beyond 11 days.

18. The method of claim 16 wherein the static cell culture is not terminated until some point in time beyond 12 days.

19. The method of claim 16 wherein the static cell culture is not terminated until some point in time beyond 13 days.

20. The method of claim 16 wherein the static cell culture is not terminated until some point in time beyond 14 days.

* * * * *